US009918682B2

(12) United States Patent
Nakada et al.

(10) Patent No.: US 9,918,682 B2
(45) Date of Patent: Mar. 20, 2018

(54) CATHETER TIP-END ROTATION ANGLE MEASUREMENT APPARATUS, CATHETER TIP-END ROTATION ANGLE MEASUREMENT METHOD, AND CATHETER TIP-END ROTATION ANGLE MEASUREMENT PROGRAM

(71) Applicant: Panasonic Corporation, Osaka (JP)

(72) Inventors: Toru Nakada, Kyoto (JP); Kazuki Kozuka, Fukui (JP); Taichi Sato, Kyoto (JP)

(73) Assignee: PANASONIC CORPORATION, Osaka (JP)

( * ) Notice: Subject to any disclaimer, the term of this patent is extended or adjusted under 35 U.S.C. 154(b) by 945 days.

(21) Appl. No.: 14/197,802

(22) Filed: Mar. 5, 2014

(65) Prior Publication Data

US 2014/0187921 A1 Jul. 3, 2014

Related U.S. Application Data

(63) Continuation of application No. PCT/JP2013/003485, filed on Jun. 3, 2013.

(30) Foreign Application Priority Data

Jun. 7, 2012 (JP) .................................. 2012-129552

(51) Int. Cl.
*A61B 6/12* (2006.01)
*A61B 6/00* (2006.01)
(Continued)

(52) U.S. Cl.
CPC ................ *A61B 6/12* (2013.01); *A61B 6/461* (2013.01); *G09B 23/285* (2013.01); *A61M 25/0105* (2013.01)

(58) Field of Classification Search
None
See application file for complete search history.

(56) References Cited

U.S. PATENT DOCUMENTS 8,849,375 B2 * 9/2014 Baumgart ................ A61B 8/12
600/424
2008/0146942 A1 * 6/2008 Dala-Krishna .......... A61B 6/12
600/466
(Continued)

FOREIGN PATENT DOCUMENTS

JP 7-246183 9/1995
JP 9-225023 9/1997
(Continued)

OTHER PUBLICATIONS

International Preliminary Report on Patentability and Written Opinion of the International Searching Authority dated Dec. 18, 2014 in International (PCT) Application No. PCT/JP2013/003485.
(Continued)

*Primary Examiner* — Katherine Fernandez
(74) *Attorney, Agent, or Firm* — Wenderoth, Lind & Ponack, L.L.P.

(57) ABSTRACT

A catheter tip-end rotation angle calculation apparatus includes a movement restriction unit, of a tube shape, that is configured to be penetrated from a first hole to a second hole of a catheter on tip end and opposite sides, and restricts movement of the catheter to an insertion direction by causing the catheter to pass through from the first hole to the second hole, first and second rotation angle measurement units that measure first and second rotation angles of the catheter at the first and second holes, a catheter insertion length measurement unit that measures a catheter insertion length, and a catheter tip-end rotation angle calculation unit that calculates a rotation angle of the catheter tip end by using an angle difference between the first and second rotation angles, the catheter insertion length, and a distance between the first and second holes.

17 Claims, 34 Drawing Sheets

(51) Int. Cl.
*G09B 23/28* (2006.01)
*A61M 25/01* (2006.01)

(56) References Cited

U.S. PATENT DOCUMENTS

2008/0204012 A1    8/2008  Krueger et al.
2012/0035467 A1    2/2012  Lichtenstein

FOREIGN PATENT DOCUMENTS

| | | |
|---|---|---|
| JP | 2000-10467 | 1/2000 |
| JP | 2007-306993 | 11/2007 |
| JP | 2009-507543 | 2/2009 |
| JP | 2009-522016 | 6/2009 |
| JP | 2009-162920 | 7/2009 |
| JP | 2012-35080 | 2/2012 |
| WO | 2007/111737 | 10/2007 |

OTHER PUBLICATIONS

International Search Report dated Jul. 2, 2013 in International (PCT) Application No. PCT/JP2013/003485.
Koichi Ogawa et al., "Fundamental Robotics", 1998, p. 98, Tokyo Denki University Press along with English translation.

* cited by examiner

CATHETER TIP-END ROTATION ANGLE MEASUREMENT APPARATUS, CATHETER TIP-END ROTATION ANGLE MEASUREMENT METHOD, AND CATHETER TIP-END ROTATION ANGLE MEASUREMENT PROGRAM

CROSS-REFERENCE TO RELATED APPLICATIONS

This is a continuation application of International Application No. PCT/JP2013/003485, with an international filing date of Jun. 3, 2013, which claims priority from Japanese Patent Application No. 2012-129552 filed on Jun. 7, 2012, the entire disclosure of which, including specification, claims, drawings, and summary, is incorporated herein by reference in its entirety.

TECHNICAL FIELD

The technical field relates to a catheter tip-end rotation angle measurement apparatus, a catheter tip-end rotation angle measurement method, and a catheter tip-end rotation angle measurement program for measuring the rotation angle of a tip end of a catheter.

BACKGROUND ART

In recent years, diagnosis or treatment of a lesion or a stenosis is performed by inserting a catheter into a blood vessel or the like of a patient (for example, PCI (Percutaneous Coronary Intervention) or TAE (Transcatheter Arterial Embolization)).

During the diagnosis or treatment, a surgeon manipulates the catheter while monitoring an X-ray fluoroscopic image of a tip end of the catheter. At this time, the surgeon needs to accurately grasp the direction of the tip end of the catheter in order to align, at a branching portion of the blood vessel, the direction of the tip end of the catheter with the branching direction of a target blood vessel.

As a conventional technique for detecting the direction of a catheter, a method of detecting the rotation angle of the catheter at the hand of the surgeon is disclosed (see Patent Literature 1). Also, a method of mounting a rotation detection sensor at a tip end portion of an electronic endoscope, and automatically correcting a display image on a monitor obtained with a twist in the electronic endoscope is disclosed (see Patent Literature 2).

CITATION LIST

Patent Literatures

[Patent Literature 1] JP 2009-162920 A
[Patent Literature 2] JP 7-246183 A
[Patent Literature 3] JP 2009-522016 W However, with the method of Patent Literature 1, in the case where the rotation angle at the hand of the surgeon and the rotation angle of the tip end of the catheter do not coincide, the rotation angle at the tip end of the catheter cannot be accurately grasped. Also, with the method of Patent Literature 2, a rotation detection sensor has to be mounted at the tip end of the catheter.

Accordingly, one non-limiting and exemplary embodiment provides a catheter tip-end rotation angle measurement apparatus, a catheter tip-end rotation angle measurement method, and a catheter tip-end rotation angle measurement program for more accurately measuring the rotation angle of a tip end of a catheter

SUMMARY OF THE INVENTION

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: A catheter tip-end rotation angle measurement apparatus for measuring a rotation angle of a tip end of a catheter inserted into a body lumen, the apparatus comprising:

a movement restriction unit, of a tube shape that is penetrated from a first hole to a second hole, that restricts movement of the catheter to an insertion direction by causing the catheter to pass through from the first hole to the second hole;

a first rotation angle measurement unit that measures a first rotation angle that is a rotation angle of the catheter at the first hole;

a second rotation angle measurement unit that measures a second rotation angle that is a rotation angle of the catheter at the second hole;

a catheter insertion length measurement unit that measures a catheter insertion length that is a length from the first hole or the second hole to a tip end portion of the catheter; and a catheter tip-end rotation angle calculation unit that calculates the rotation angle of the tip end of the catheter by using an angle difference between the first rotation angle measured by the first rotation angle measurement unit and the second rotation angle measured by the second rotation angle measurement unit, the catheter insertion length measured by the catheter insertion length measurement unit, and a distance between the first hole and the second hole.

These general and specific aspects may be implemented using a system, a method, an integrated electronics circuit, a computer program, and a storage medium, and any combination of systems, methods, integrated electronics circuits, computer programs, and storage mediums.

According to the aspect of the present invention, the rotation angle of the tip end of the catheter may be more accurately measured.

BRIEF DESCRIPTION OF THE DRAWINGS

These and other aspects and features of the present disclosure will become clear from the following description taken in conjunction with the embodiments thereof with reference to the accompanying drawings, in which.

DETAILED DESCRIPTION

Figure 1:
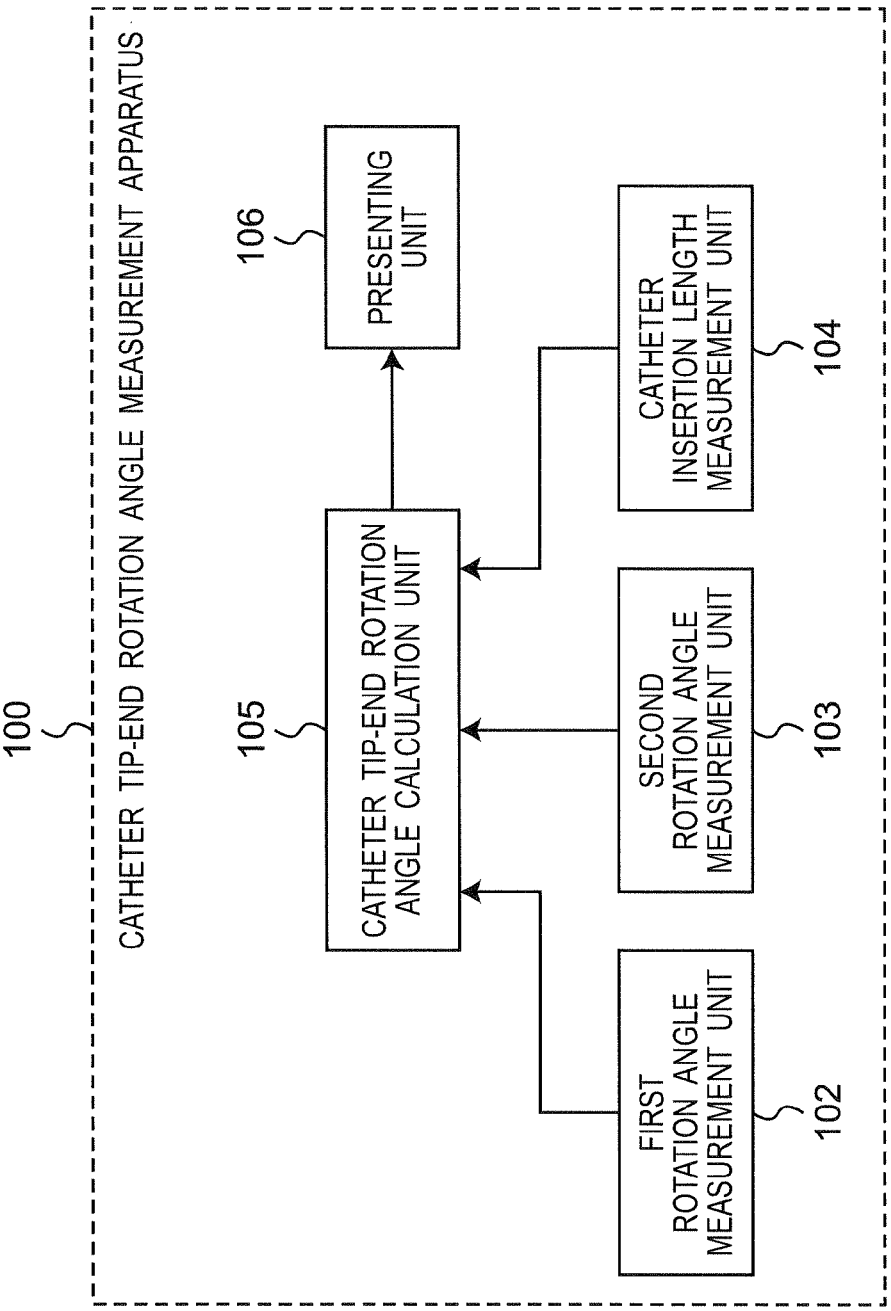
FIG. 1 is a block diagram showing a functional configuration of a catheter tip-end rotation angle measurement apparatus according to a first embodiment.

Findings which the Present Disclosure is Based on

There are various types of catheters or guide wires to be inserted before catheters so that insertion to a portion to be diagnosed or treated may be carried out smoothly, and there are various modes or functions according to the usage. For example, there is a catheter called Judkins for the right coronary artery or the left coronary artery, and the tip end is bent in accordance with the anatomical location to achieve a shape that can be easily inserted to the portion to be diagnosed or treated.

Also, a surgeon performs a manipulation of aligning, at a branching portion of a blood vessel or the like, the tip end of a catheter or the tip end of a guide wire with a branching direction of a target blood vessel or the like to insert the catheter or the guide wire into the target blood vessel or the like. At this time, in order to align the tip end of the catheter or the like with the branching direction of the target blood vessel or the like, the surgeon has to accurately grasp the direction of the tip end of the catheter or the like.

However, with a conventional method of displaying an X-ray fluoroscopic image of a catheter which has been radiographed from one direction on a monitor, the X-ray fluoroscopic image will be a two-dimensional image, and there is a disadvantage that the direction, especially the depth direction, of the tip end of the catheter or the like is hard to grasp. That is, it is difficult for a surgeon to grasp which of a direction toward the monitor and a direction away from the monitor the tip end of the catheter or the like is facing, and this may interfere with smooth manipulation of the catheter or the like.

On the other hand, there is a method of radiographing a catheter or the like from two directions using an X-ray fluoroscopic device called a biplane type including two sets of X-ray generators and X-ray detectors. However, according to the radiographing by the biplane type, image-capturing is normally performed with an angle difference of 90 degrees, and thus, it is a great burden to the surgeon to instantly and intuitively grasp the stereoscopic shape of the tip end of the catheter while alternately observing the two captured X-ray fluoroscopic images with an angle difference of 90 degrees and taking into account the capturing angle of each X-ray generator and X-ray detector.

Accordingly, as conventional methods of detecting the direction of the tip end of a catheter, the methods of Patent Literatures 1 and 2 are proposed.

Patent Literature 1 discloses a method of measuring, by a device that simulates three-dimensional motion of a catheter, a rotation angle of the catheter at the hand of a surgeon by using a rotary encoder or the like. However, in the case where the surgeon moves the catheter in an insertion direction or in a rotation direction with the insertion direction as the axis in a state where the catheter is in contact with the inner wall or a branching portion of a blood vessel, the catheter may be twisted. If twisting occurs, the rotation angle of the catheter at the hand of the surgeon and the rotation angle of the tip end of the catheter will not coincide. Thus, with the method of Patent Literature 1, the direction of the tip end of the catheter cannot be accurately detected in the case where the catheter is twisted.

Also, Patent Literature 2 discloses a method of mounting a rotation detection sensor at a tip end portion of an electronic endoscope of an electronic endoscope system, and correcting rotation of the axis for an imaged is played on a monitor caused by twisting of the electronic endoscope. However, since the rotation detection sensor is mounted to the tip end of a catheter to be inserted into a blood vessel whose diameter is several millimeters, there is a risk that the blood vessel is damaged by the rotation detection sensor coming into contact with the blood vessel during manipulation of the catheter.

In order to solve the conventional problems, one non-limiting and exemplary embodiment provides an apparatus for measuring the rotation angle of the tip end of a catheter that may be twisted, without mounting a rotation detection sensor to the tip end of the catheter.

Before the description of the present invention proceeds, it is to be noted that like parts are designated by like reference numerals throughout the accompanying drawings.

Before the description of the various embodiments proceeds, various approaches made by the inventors to accomplish the embodiments are explained.

Examples of the disclosed technique are as follows.

1st aspect: A catheter tip-end rotation angle measurement apparatus for measuring a rotation angle of a tip end of a catheter inserted into a body lumen, the apparatus comprising:

a movement restriction unit, of a tube shape that is penetrated from a first hole to a second hole, that restricts movement of the catheter to an insertion direction by causing the catheter to pass through from the first hole to the second hole;

a first rotation angle measurement unit that measures a first rotation angle that is a rotation angle of the catheter at the first hole;

a second rotation angle measurement unit that measures a second rotation angle that is a rotation angle of the catheter at the second hole;

a catheter insertion length measurement unit that measures a catheter insertion length that is a length from the first hole or the second hole to a tip end portion of the catheter; and a catheter tip-end rotation angle calculation unit that calculates the rotation angle of the tip end of the catheter by using an angle difference between the first rotation angle measured by the first rotation angle measurement unit and the second rotation angle measured by the second rotation angle measurement unit, the catheter insertion length measured by the catheter insertion length measurement unit, and a distance between the first hole and the second hole.

According to this configuration, the rotation angle of the tip end of the catheter may be measured without mounting a rotation detection sensor or the like to the tip end of the catheter. Thus, since there is no need to mount the rotation detection sensor or the like to the tip end of the catheter, the possibility of damaging a blood vessel during a catheter manipulation, which is a subtle, delicate manipulation, may be reduced.

For example, the catheter tip-end rotation angle measurement apparatus further comprises:

a presenting unit that presents the rotation angle of the tip end of the catheter calculated by the catheter tip-end rotation angle calculation unit to a user.

According to this configuration, the rotation angle of the tip end of the catheter which has been measured may be presented to a user. Thus, a surgeon may accurately grasp the direction of the tip end of the catheter based on the rotation angle of the tip end of the catheter which has been measured. A surgeon is thereby enabled to easily align, at a branching portion of a blood vessel, the tip end of the catheter with the branching direction of the target blood vessel or the like, and smooth catheter manipulation is enabled. Also, since smooth catheter manipulation may reduce the surgery time, the radiation time of X-rays radiated on a patient may be reduced. Thus, the dose of radiation to the patient by X-ray radiation may be lowered.

For example, in the catheter tip-end rotation angle measurement apparatus, the catheter tip-end rotation angle calculation unit calculates θ that is the rotation angle of the tip end of the catheter by $\theta = \theta_1 - (\theta_1 - \theta_2) \cdot L/L_{12}$, where the first rotation angle measured by the first rotation angle measurement unit is given as $\theta_1$, the second rotation angle measured by the second rotation angle measurement unit is given as $\theta_2$, the catheter insertion length measured with respect to the first hole is given as L, and the distance between the first hole and the second hole is given as $L_{12}$.

According to this configuration, in a case where the catheter is uniformly twisted, the catheter tip-end rotation angle calculation unit may measure the rotation angle of the tip end of the catheter by using the fact that the relationship of a difference $(\theta - \theta_1)$ between the first rotation angle and the rotation angle of the tip end of the catheter and an angle difference $(\theta_1 - \theta_2)$ between the first rotation angle and the second rotation angle is proportional to the relationship of the catheter insertion length (L) and the distance $(L_{12})$ between the first hole and the second hole.

For example, the catheter tip-end rotation angle measurement apparatus further comprises:

a first image acquisition unit that acquires an X-ray image captured by an X-ray image capturing device that image-captures a region including the tip end portion of the catheter inserted into the body lumen;

a catheter tip-end portion extraction unit that extracts the tip end portion of the catheter from the X-ray image acquired by the first image acquisition unit; and a motion detection unit that detects motion of the tip end portion of the catheter extracted by the catheter tip-end portion extraction unit, wherein the catheter tip-end rotation angle calculation unit calculates the rotation angle of the tip end of the catheter in a case where the motion detection unit detects motion, and does not calculate the rotation angle of the tip end of the catheter in a case where the motion detection unit does not detect motion.

According to this configuration, when motion of the tip end of the catheter is detected, the rotation angle of the tip end of the catheter is measured. Thus, a surgeon may grasp the rotation angle of the tip end of the catheter in real time according to his/her catheter manipulation.

For example, the catheter tip-end rotation angle measurement apparatus further comprises:

an image-capturing parameter information acquisition unit that acquires image-capturing parameter information that is information about an image-capturing condition and an orientation of each X-ray image capturing device at a time of image-capturing;

a second image acquisition unit that acquires a plurality of X-ray images including the tip end portion of the catheter captured by a plurality of X-ray image capturing devices provided at different positions;

a catheter rotation axis determination unit that extracts a part of the catheter that is straight in each X-ray image based on the plurality of X-ray images acquired by the second image acquisition unit, reconstructs a three-dimensional shape of the catheter by using the extracted part of the catheter that is straight and the image-capturing parameter information at a time of image-capturing of the each X-ray image acquired by the image-capturing parameter information acquisition unit, and determines a catheter rotation axis that is a rotation axis with respect to the insertion direction of the catheter based on the reconstructed three-dimensional shape of the catheter;

a catheter shape storage unit that stores, for a plurality of types of catheters, shapes of tip ends of the catheters for each rotation angle of the tip ends of the catheters; and a catheter tip-end rotation angle correction unit, wherein the catheter tip-end rotation angle correction unit includes:

an acquisition unit that acquires a first X-ray image from the plurality of X-ray images from the second image acquisition unit, the rotation angle at the tip end of the catheter and the second rotation angle from the catheter tip-end rotation angle calculation unit, the catheter rotation axis from the catheter rotation axis determination unit, and image-capturing parameter information at a time of capturing the first X-ray image from the image-capturing parameter information acquisition unit;

a calibration image generation unit that acquires from the catheter shape storage unit, for respective rotation angles from the rotation angle of the tip end of the catheter to the second rotation angle acquired by the acquisition unit, a plurality of shapes of the tip end of the catheter, and generates a plurality of calibration images where the acquired shapes of the tip end of the catheter and the rotation angles are associated;

a comparison unit that compares the first X-ray image acquired from the acquisition unit and the plurality of calibration images generated by the calibration image generation unit, and determines a calibration image with a highest degree of similarity to the first X-ray image; and a rotation angle determination unit that determines the rotation angle corresponding to the calibration image determined by the comparison unit, as the rotation angle of the tip end of the catheter, and wherein the presenting unit presents the rotation angle of the tip end of the catheter determined by the rotation angle determination unit to a user.

According to this configuration, the rotation angle of the tip end of the catheter may be accurately measured even in a case where a part of the catheter is twisted.

In the following, embodiments of the present disclosure will be described with reference to the drawings. Additionally, each of the embodiments described below describes a specific example of the present disclosure. The numerical values, structural elements, connection modes of the structural elements, steps, order of the steps, and the like described in the embodiments below are examples, and are not intended to restrict the present disclosure. The present disclosure is restricted only by the scope of the claims. Accordingly, among the structural elements in the embodiments below, the structural elements not described in independent claims representing the broadest concepts of the present disclosure are not necessarily required to achieve the object of the present disclosure, but are described as elements configuring more specific modes.

First Embodiment

FIG. 1 shows a functional configuration of a catheter tip-end rotation angle measurement apparatus 100 according to a first embodiment.

As shown in FIG. 1, the catheter tip-end rotation angle measurement apparatus 100 includes a first rotation angle measurement unit 102, a second rotation angle measurement unit 103, a catheter insertion length measurement unit 104, and a catheter tip-end rotation angle calculation unit 105. Also, a movement restriction unit 101, not shown, is included. In the following, each structural element of the catheter tip-end rotation angle measurement apparatus 100 will be described.

<Configuration>

<Movement Restriction Unit 101>

The movement restriction unit 101 has a tube shape which is penetrated from a first hole 1010 to a second hole 1011, and the movement of a catheter 10 is restricted to the insertion direction by causing the catheter 10 to pass through from the first hole 1010 to the second hole 1011.

Figure 2:
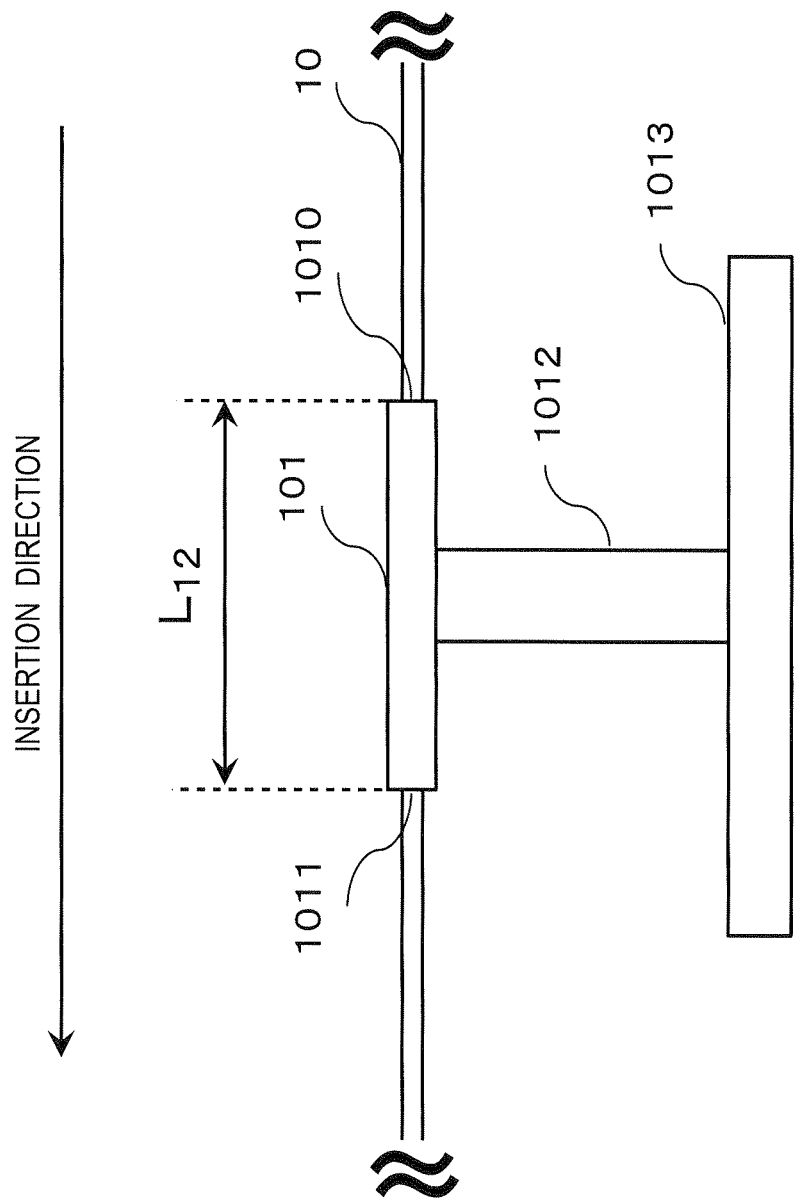
FIG. 2 is a view showing a configuration of a movement restriction unit according to the first embodiment.

FIG. 2 shows a schematic example of the movement restriction unit 101. The movement restriction unit 101 has a tube shape which is penetrated from the first hole 1010 to the second hole 1011. Also, when seen from the insertion direction, the first hole 1010 is at the back end of the movement restriction unit 101, and when seen from the insertion direction, the second hole 1011 is at the front end of the movement restriction unit 101. That is, the first hole 1010 is a hole on the side of a surgeon, and the second hole 1011 is a hole on the side of a patient.

By causing the catheter 10 to pass through from the first hole 1010 to the second hole 1011, the movement of the catheter 10 is restricted to the insertion direction. The insertion direction here includes, in addition to the axial direction of the catheter 10, rotation around the axial direction. That is, to restrict the movement of the catheter 10 to the insertion direction means that the catheter 10 cannot move in a radial direction that is orthogonal to the axial direction of the catheter 10.

The sizes of the first hole 1010 and the second hole 1011 are large enough to allow the catheter 10 to pass, and are greater than the diameter of the catheter 10 by a predetermined amount. The first hole 1010 and the second hole 1011 have approximately the same diameters as that of the catheter 10, and when the catheter 10 is inserted, there is almost no gap in the radial direction that is orthogonal to the axial direction of the catheter 10. The sizes of the first hole 1010 and the second hole 1011 are greater than the diameter of the catheter 10 by about 1 to 3 mm, for example. Moreover, the possible sizes of the first hole 1010 and the second hole 1011 may be different depending on the diameter or the type of the catheter 10. That is, if the catheter 10 is greater than a normal catheter, the first hole 1010 and the second hole 1011 may be greater than the diameter of the catheter 10 by about 3 mm, and if the catheter 10 is smaller than the normal catheter, the first hole 1010 and the second hole 1011 may be greater than the diameter of the catheter 10 by about 1 mm.

Furthermore, the frictional resistance of the inner surface of the tube is desirably small. Then, catheter manipulation may be performed smoothly, and twisting of the catheter 10 inside the movement restriction unit 101 may be prevented.

The distance $L_{12}$ from the first hole 1010 to the second hole 1011 is the same as the length of the movement restriction unit 101. Also, as will be described below, measurement of the rotation angle of the tip end of the catheter 10 may be performed more accurately as the length of the movement restriction unit 101 is longer. However, if the length of the movement restriction unit 101 is long, there is a disadvantage that catheter manipulation becomes difficult. Here, for example, the length of the movement restriction unit 101 is about 10 cm.

Moreover, the movement restriction unit 101 may be fixed to a pedestal 1013 by a leg 1012. When the movement restriction unit 101 is fixed to the pedestal 1013, the first rotation angle and the second rotation angle described below may be measured with high accuracy.

<First Rotation Angle Measurement Unit 102>

The first rotation angle measurement unit 102 measures a first rotation angle $\theta_1$, which is the rotation angle of the catheter 10 at the first hole 1010.

The measurement position of the first rotation angle measurement unit 102 is a predetermined range including the position of the first hole 1010. The measurement position of the first rotation angle measurement unit 102 is more desirable as it is closer to the first hole 1010, and is within the range of 3 mm from the first hole, for example.

Figure 3:
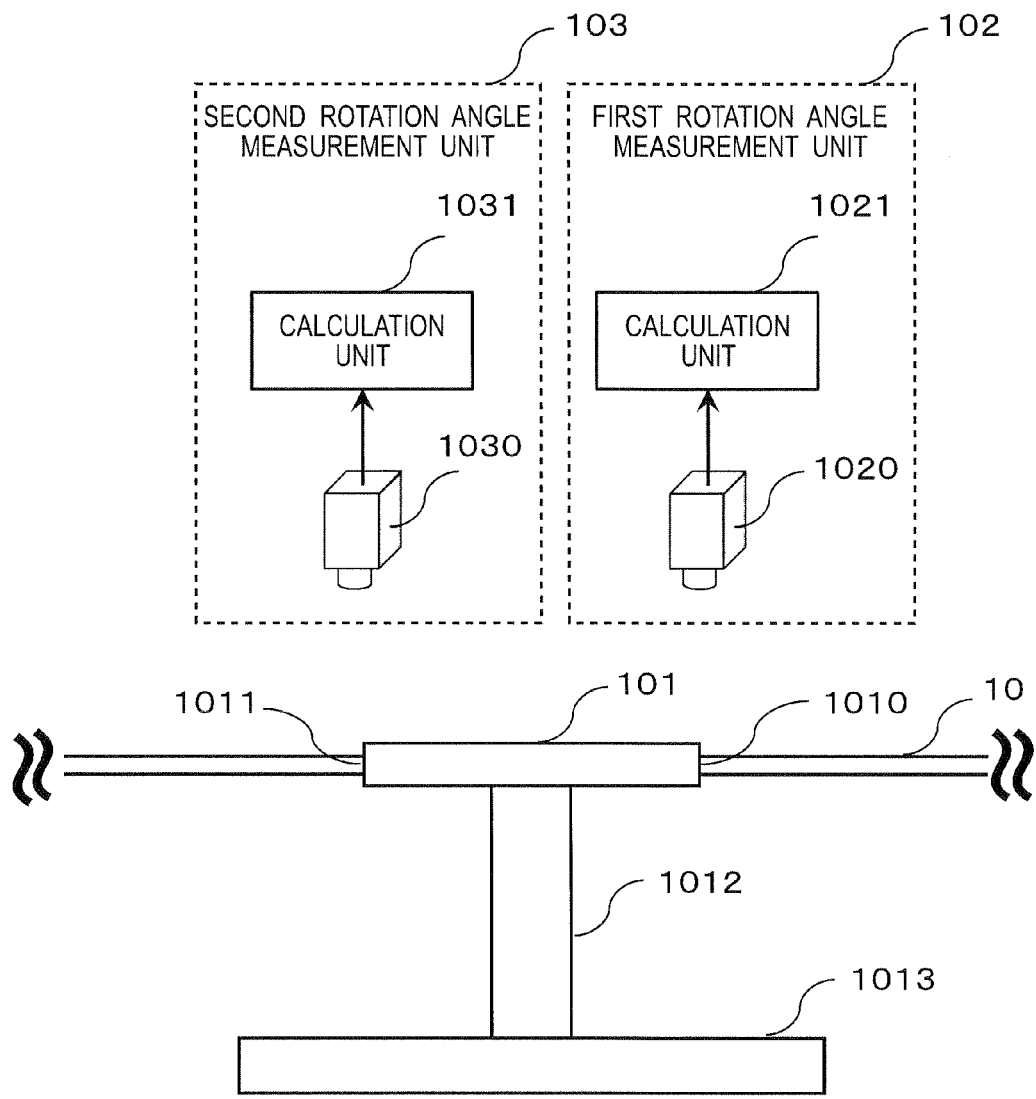
FIG. 3 is a view showing examples of a first rotation angle measurement unit and a second rotation angle measurement unit according to the first embodiment.
Figure 4:
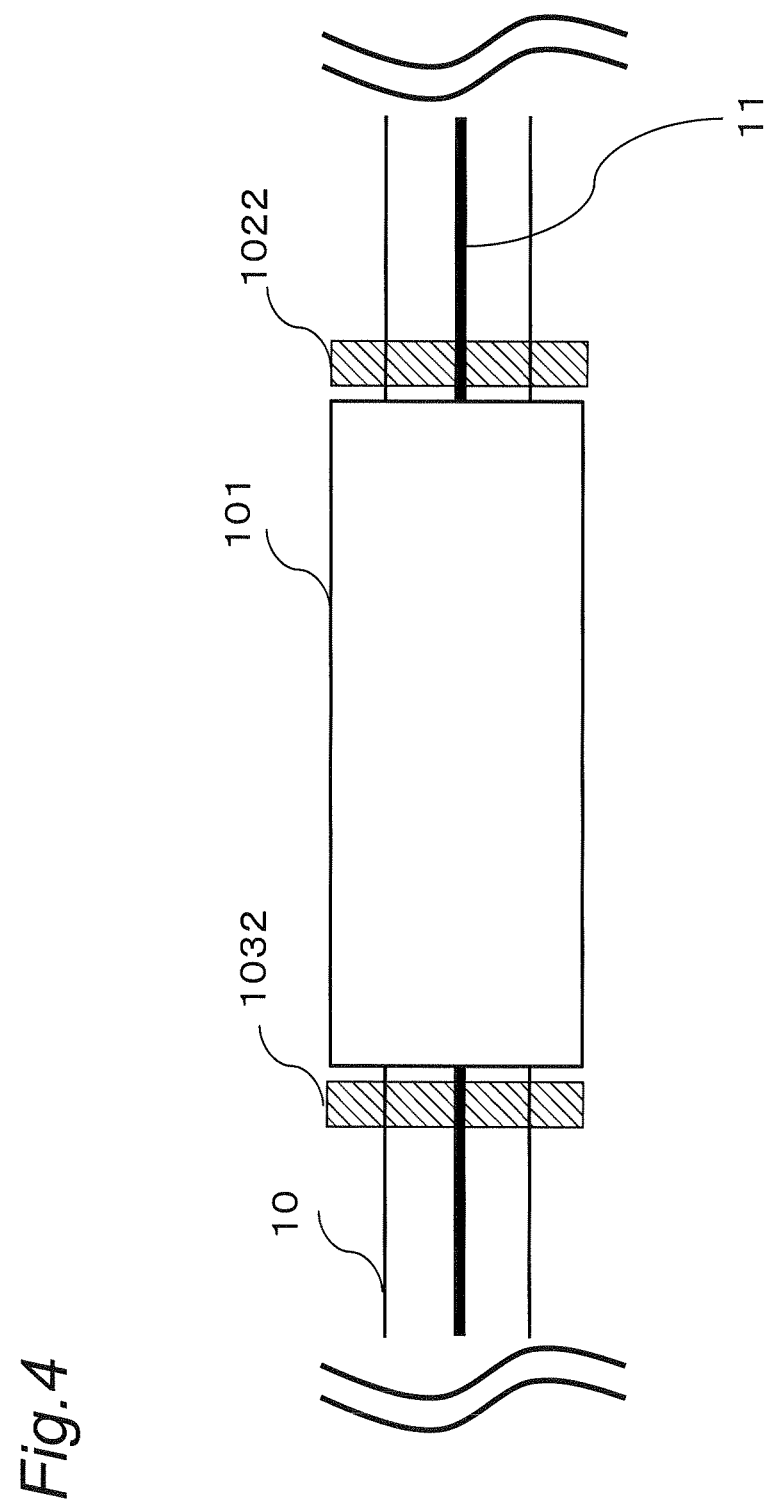
FIG. 4 is a view showing regions to be measured by the first rotation angle measurement unit and the second rotation angle measurement unit according to the first embodiment.

FIG. 3 shows a schematic example of the first rotation angle measurement unit 102. The first rotation angle measurement unit 102 is configured by an image-capturing unit 1020, and a calculation unit 1021. FIG. 4 shows the movement restriction unit 101 seen from above. A line 11 that is parallel to the center axis of the catheter 10 is drawn on the surface of the catheter 10 in advance. The image-capturing unit 1020 image-captures a range 1022. The calculation unit 1021 extracts the position of the line 11 from an image captured by the image-capturing unit 1020, and acquires the rotation angle in the range 1022 by the displacement of the line 11 with respect to the center of the catheter 10. In the following, a concrete method of the first rotation angle measurement unit 102 to measure the first rotation angle will be described.

The image-capturing unit 1020 is a camera, for example, and the calculation unit 1021 is a CPU of a PC, for example. The image-capturing unit 1020 starts image-capturing upon reception of input of detection start from a surgeon. The image-capturing unit 1020 keeps image-capturing the catheter 10 at specific intervals.

Figure 5:
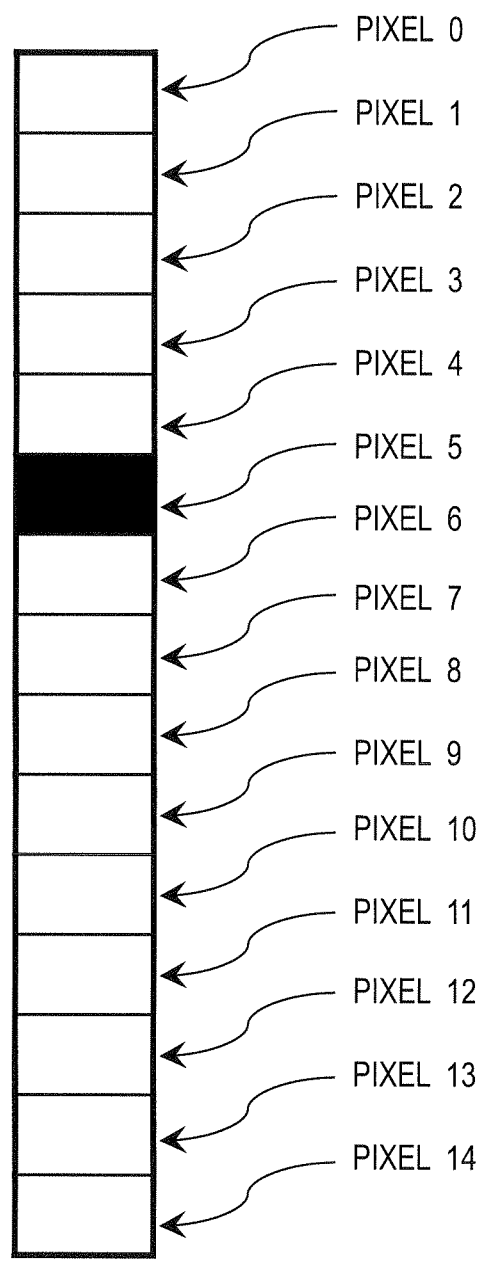
FIG. 5 is a view showing correspondence between a line sensor and pixels.

The calculation unit 1021 extracts the position of the line 11 in each of a plurality of images which have been captured. With respect to the extraction, in the case where the catheter 10 is white and the line 11 is black, for example, the position of the black is extracted. FIG. 5 shows an image that is captured, for a case where the image-capturing unit 1020 is a line sensor including 15 pixels. Here, for the sake of simplicity, description is given assuming that the image-capturing unit 1020 is arranged such that the entire width (direction perpendicular to the axial direction) of the catheter 10 is captured in 15 pixels. As shown in FIG. 5, numbers (n=0, 1, 2, ..., 14) are sequentially assigned to the pixels from above. In the case of FIG. 5, the calculation unit 1021 performs a process of acquiring "5" which is the number of pixel 5. More specifically, the calculation unit 1021 determines whether the brightness of each pixel is equal to or less than a threshold. For example, the brightness of a pixel takes a value between 0 and 255, and 50 is given as the threshold by taking 0 to be the darkest and 255 to be the brightest. The number of the pixel whose brightness is equal to or less than the threshold is taken as the position of the line 11.

Figure 6:
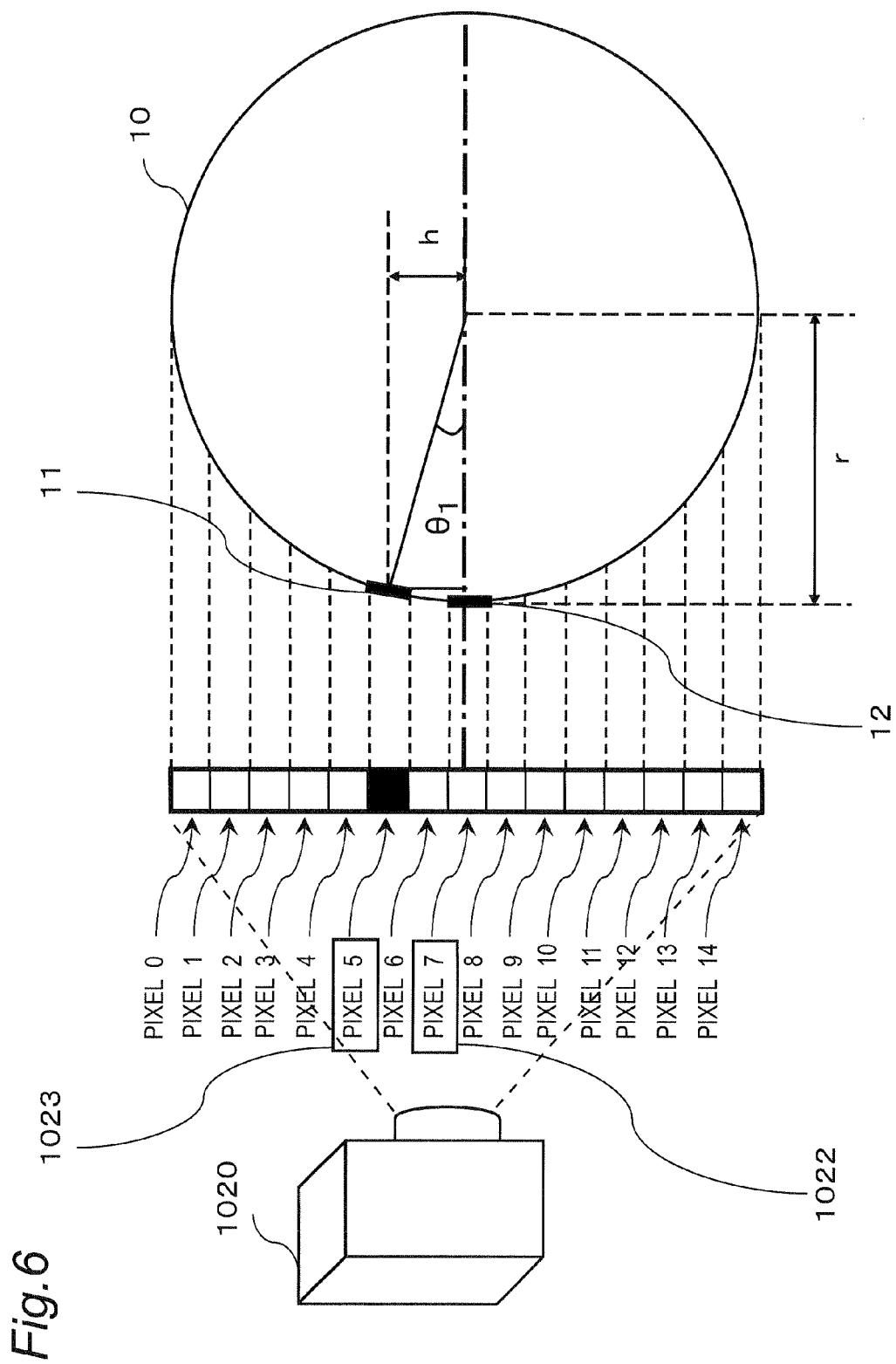
FIG. 6 is an explanatory view showing a relationship between a cross section of a catheter, an image-capturing unit, and pixels.

Next, the calculation unit 1021 measures the rotation angle at the range 1022 from the position of the line 11 which has been extracted. FIG. 6 shows a relationship of the position of the line 11 and the rotation angle of the catheter. The circle shown on the right in FIG. 6 is a cross section of the catheter 10. The image-capturing unit 1020 is shown on the left side in FIG. 6. The image-capturing unit 1020 includes elements for image-capturing pixels 0 to 14, and these are shown in the middle in FIG. 6 in an enlarged manner. Also, the boundaries of ranges image-captured by respective pixels are shown by dotted lines. Pixel 7 is the pixel image-capturing the center of the range (in this case, from pixel 0 to pixel 14) of the catheter in an image captured by the image-capturing unit 1020. In the following, pixel 7 will be referred to as a center pixel 1022. The surface portion of the catheter 10 image-captured in the center pixel 1022 is given as a center position 12. A radius r is the length of the radius of the catheter 10 in an image captured by the image-capturing unit 1020. In FIG. 6, the radius r is equal to the length from the center pixel 1022 to pixel 14 where an edge of the catheter 10 is image-captured, and is 14−7=7, i.e. seven pixels. Pixel 5 is the position of the line 11 drawn on the surface of the catheter 10. In the following, pixel 5 will be referred to as a line position pixel 1023. A distance h is the distance, based on pixels, from the line position pixel 1023 to the center pixel 1022, and is, in this case, 7−5=2. An angle $\theta_1$ is a rotation angle of the line 11 with respect to the center position 12, that is, the first rotation angle, which is the rotation angle of the catheter 10 at the first hole 1010.

The angle $\theta_1$ is expressed by a relational expression of Equation (1) based on the definition of the trigonometric function.

$$\sin \theta_1 = h/r \qquad \text{Equation (1)}$$

Accordingly, the angle $\theta_1$ is Equation (2) from Equation (1).

$$\theta_1 = \arcsin(h/r) \qquad \text{Equation (2)}$$

Here, the function arcsin is an inverse function of sin function. Accordingly, in the case in FIG. 6, $\theta_1 = \arcsin(\frac{2}{7})$ is true, and the first rotation angle $\theta_1$, which is the rotation angle of the catheter 10 at the first hole 1010, may thus be measured.

Figure 7:
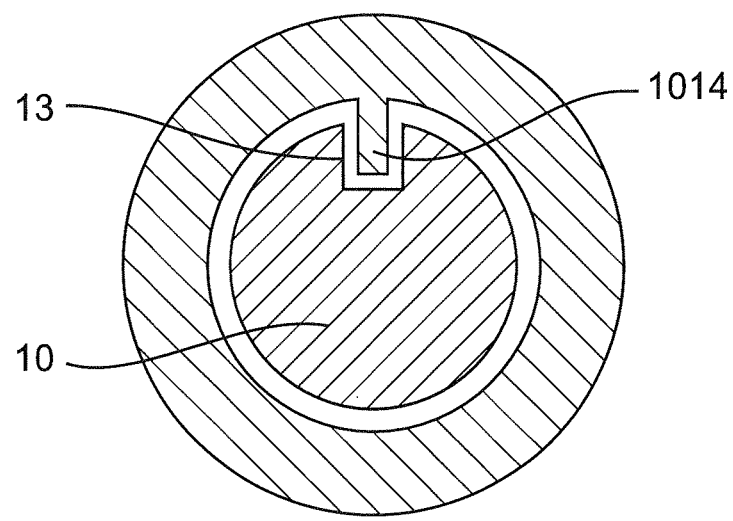
FIG. 7 is a cross-sectional view showing a relationship between a rotary encoder and the catheter.

Additionally, the first rotation angle measurement unit 102 does not have to be configured by the image-capturing unit 1020 and the calculation unit 1021, and it may also be configured by a rotary encoder or the like. FIG. 7 shows a configuration view of the first rotational angle measurement unit 102 for a case of measuring the rotation angle of the catheter 10 by using a rotary encoder. FIG. 7 shows a state seen from the insertion direction of the catheter 10. When a groove portion 13 provided to the catheter 10 in advance and a protrusion portion 1014 provided to the inside of the movement restriction unit 101 in advance are meshed with each other, rotation of the catheter 10 and rotation of the rotary encoder are synchronized, and the rotation angle of the catheter 10 may be measured. As the rotary encoder in this case, an absolute value encoder or the like (Koichi OGAWA et al., Fundamental Robotics, 1998, p. 98, Tokyo Denki University Press) may be used.

<Second Rotation Angle Measurement Unit 103>

The second rotation angle measurement unit 103 measures a second rotation angle $\theta_2$, which is the rotation angle of the catheter 10 at the second hole 1011.

The second rotation angle measurement unit 103 may be realized by the same configuration as the first rotation angle measurement unit 102. FIG. 3 shows a schematic example of the second rotation angle measurement unit 103. The second rotation angle measurement unit 103 is configured by an image-capturing unit 1030, and a calculation unit 1031. Also, the concrete method of the second rotation angle measurement unit 103 to measure the second rotation angle $\theta_2$ by using the image-capturing unit 1030 and the calculation unit 1031 is the same as the method of the first rotation angle measurement unit 102 to measure the first rotation angle $\theta_1$.

Additionally, the second rotation angle measurement unit 103 does not have to be configured by the image-capturing unit 1030 and the calculation unit 1031, and it may also be configured from a rotary encoder or the like. Also, the concrete method of the second rotation angle measurement unit 103 to measure the second rotation angle $\theta_2$ by using the rotary encoder is the same as the method of the first rotation angle measurement unit 102 to measure the first rotation angle $\theta_1$.

<Catheter Insertion Length Measurement Unit 104>

The catheter insertion length measurement unit 104 measures a catheter insertion length L, which is the length from the first hole 1010 or the second hole 1011 to a tip end portion of the catheter 10.

Figure 8:
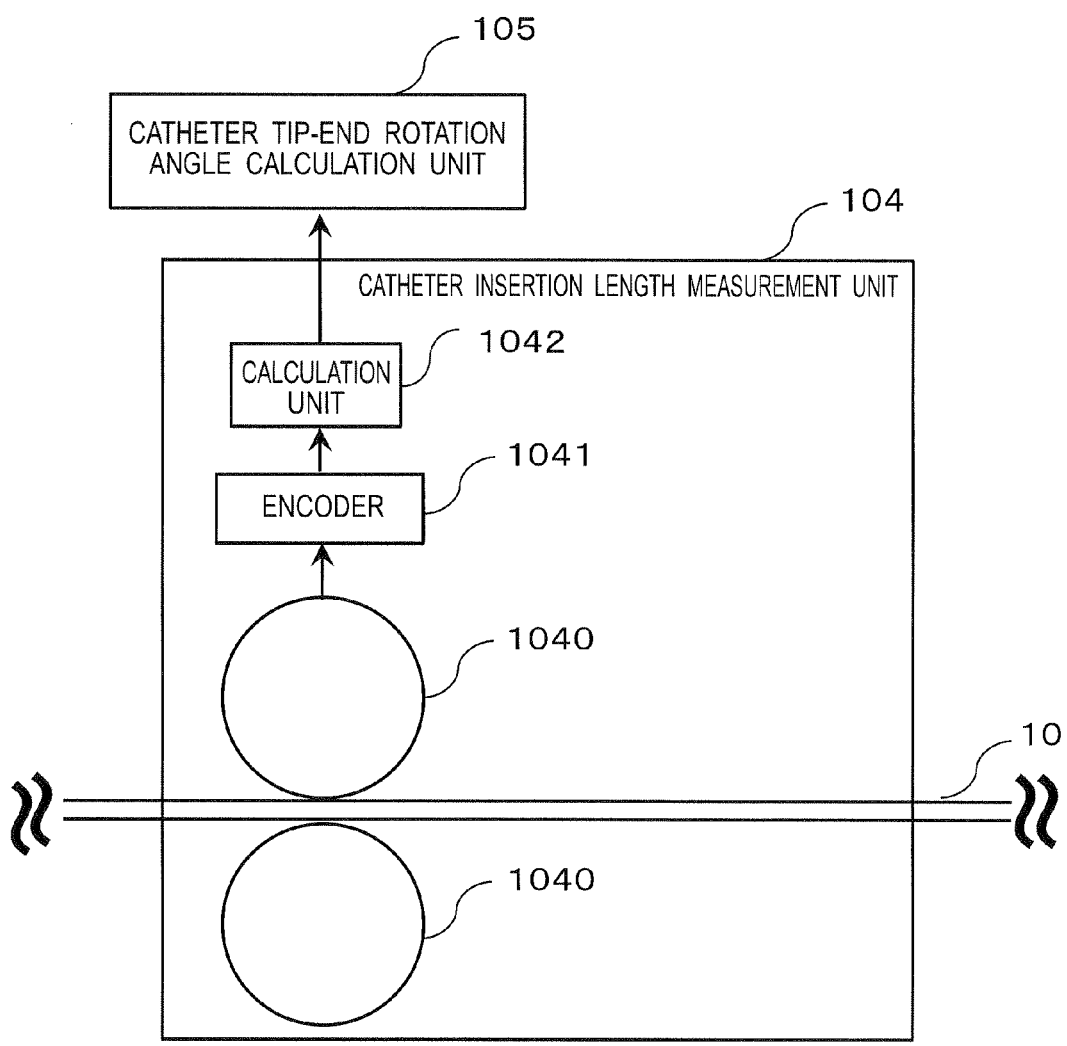
FIG. 8 is an explanatory view showing a configuration of a catheter insertion length measurement unit according to the first embodiment.

FIG. 8 shows a schematic example of the catheter insertion length measurement unit 104. FIG. 8 shows a case where the length from the first hole 1010 to a tip end portion 15 of the catheter 10 is given as the catheter insertion length L. The catheter insertion length measurement unit 104 is configured by rollers 1040 that move in conjunction with the forward/backward movement of the catheter 10 by pressing the catheter 10, an encoder 1041 for measuring the amount of rotation of the rollers 1040, and a calculation unit 1042 for calculating the insertion length from the amount of change in the value of the rotation angle from the encoder 1041, for example.

Before the manipulation of the catheter 10 is started, the calculation unit 1042 sets an initial value "0". When the manipulation of the catheter 10 is to be started, the catheter 10 is passed between the rollers 1040, and the calculation unit 1042 starts calculation of the insertion length of the catheter 10 at this time, and keeps calculating until the manipulation of the catheter 10 is ended. Accordingly, the catheter insertion length measurement unit 104 may keep measuring the insertion length L of the catheter 10 in real time during the manipulation of the catheter 10.

Figure 9:
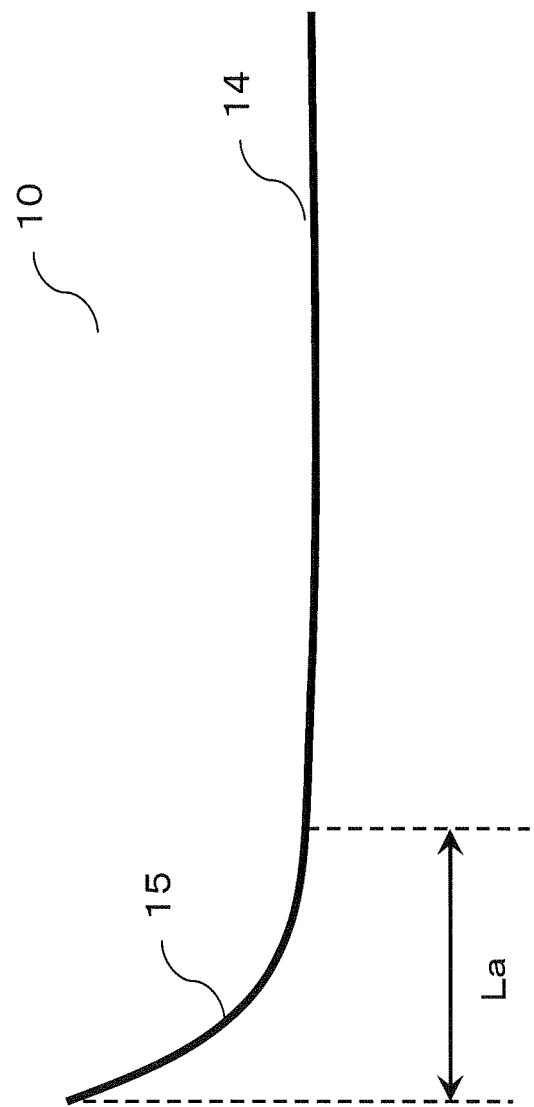
FIG. 9 is an overall view of a catheter having a bent portion.

Furthermore, as shown in FIG. 9, a bent portion 15 is provided to the tip end of the catheter 10. The bent portion 15 (hereinafter referred to also as "the tip end portion 15 of the catheter") is of a material different from that of other portions of the catheter 10, and is easily bent. The catheter insertion length measurement unit 104 measures the distance from the first hole 1010 to the bent portion 15 as the catheter insertion length L. That is, the length of the catheter not including the tip end portion 15 corresponds to the catheter insertion length L. By not including the tip end portion 15 of the catheter in the catheter insertion length L, the rotation angle $\theta$ of the tip end of the catheter 10 may be more accurately calculated.

Additionally, the catheter insertion length measurement unit 104 does not necessarily have to take the length not including the tip end portion 15 of the catheter as the catheter insertion length L, and a length including the tip end portion 15 of the catheter may also be measured as the catheter insertion length L.

Moreover, the catheter insertion length measurement unit 104 may be configured to image-capture a scale regarding an insertion position described on the surface of the catheter 10 by image-capturing means such as a camera, and to calculate the insertion length based on the value on the scale.

Additionally, the catheter insertion length measurement unit 104 does not have to be provided separately from the movement restriction unit 101, and the catheter insertion length measurement unit 104 may be provided to the movement restriction unit 101.

Moreover, the catheter insertion length measurement unit 104 may take the length from the second hole 1011 to the tip end portion of the catheter 10 as the catheter insertion length L.

<Catheter Tip-End Rotation Angle Calculation Unit 105>

The catheter tip-end rotation angle calculation unit 105 calculates the rotation angle $\theta$ of the tip end of the catheter by using the angle difference $(\theta_1-\theta_2)$ between the first rotation angle $\theta_1$ measured by the first rotation angle measurement unit 102 and the second rotation angle $\theta_2$ measured by the second rotation angle measurement unit 103, the catheter insertion length L measured by the catheter insertion length measurement unit 104, and the distance $L_{12}$ between the first hole 1010 and the second hole 1011.

The catheter tip-end rotation angle calculation unit 105 acquires the first rotation angle $\theta_1$, the second rotation angle $\theta_2$, and the catheter insertion length L from the first rotation angle measurement unit 102, the second rotation angle measurement unit 103, and the catheter insertion length measurement unit 104, respectively. The catheter tip-end rotation angle calculation unit 105 calculates the angle difference $(\theta_1-\theta_2)$ between the first rotation angle $\theta_1$ and the second rotation angle $\theta_2$ which have been acquired. Also, a surgeon sets the distance $L_{12}$ between the first hole 1010 and the second hole 1011 in the catheter tip-end rotation angle calculation unit 105 in advance before starting manipulation of the catheter 10.

Figure 10:
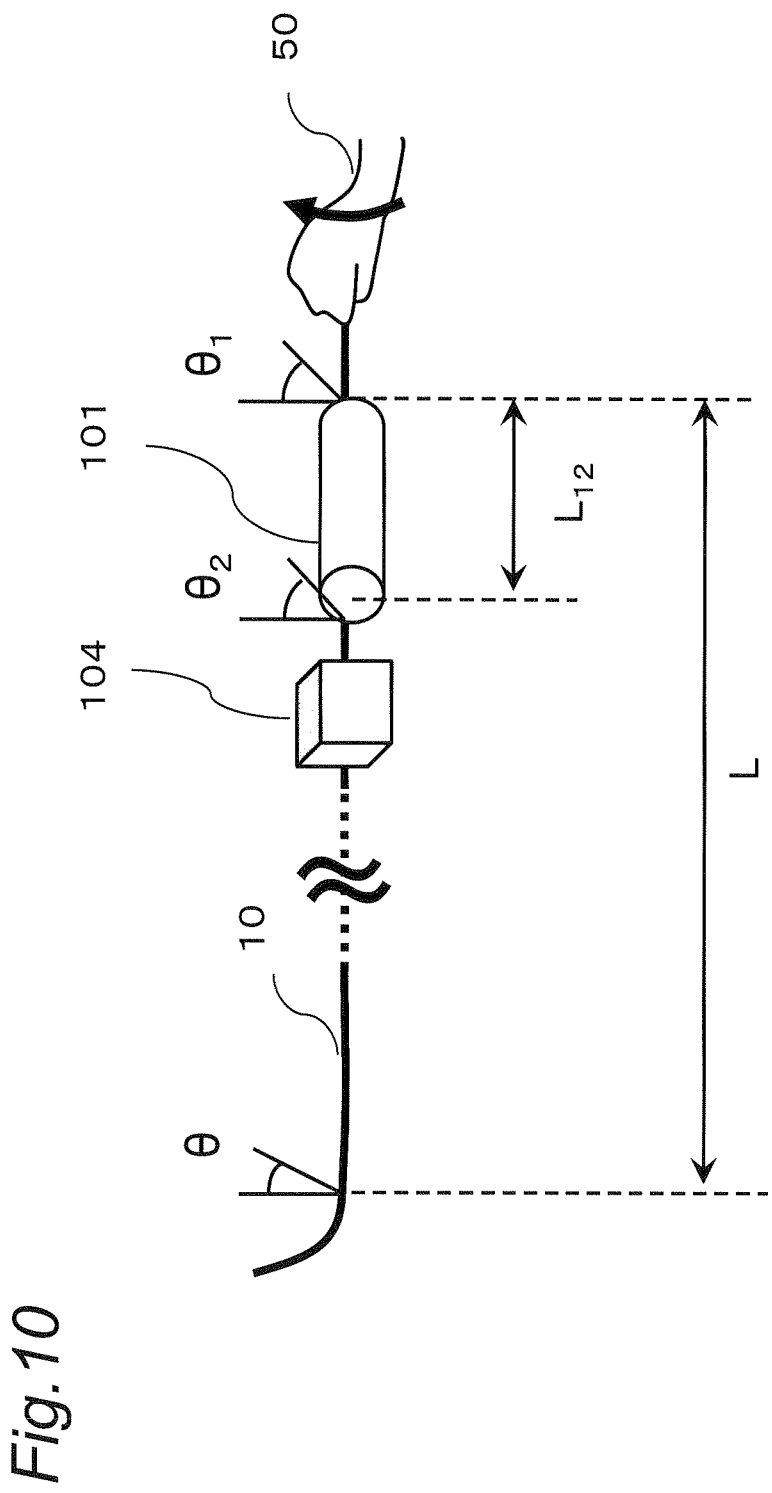
FIG. 10 is a view showing a relationship of a first rotation angle, a second rotation angle, a catheter insertion length, the length of the movement restriction unit, and the rotation angle of a tip end of the catheter according to the first embodiment.

FIG. 10 shows a relationship of parameters for a case where the first hole 1010 is on the surgeon side. In the following, a case will be described where the first hole 1010 is on the surgeon side, and where the catheter insertion length L is a length from the first hole 1010 to the tip end portion 15 of the catheter 10.

In the case where the catheter 10 is uniformly twisted, a relationship of Equation (3) is established among the parameters.

$$(\theta_1-\theta)=(\theta_1-\theta_2)\cdot L/L_{12} \quad \text{Equation (3)}$$

Equation (3) expresses that the relationship of a twist angle $(\theta_1-\theta)$ of the entire catheter 10 and a twist angle $(\theta_1-\theta_2)$ between the first hole 1010 and the second hole 1011 is proportional to the relationship of the catheter insertion length L and the distance $L_{12}$ between the first hole 1010 and the second hole 1011. Thus, the rotation angle $\theta$ of the tip end of the catheter may be calculated by Equation (4).

$$\theta=\theta_1-(0\theta_1-\theta_2)*L/L_{12} \quad \text{Equation (4)}$$

Additionally, description is given above assuming that the first hole 1010 is on the surgeon side, but a case where the first hole 1010 is on the patient side and the second hole 1011 is on the surgeon side is also conceivable. In this case, Equation (3) is changed to Equation (5).

$$(\theta_2-\theta)=(\theta_2-\theta_1)\cdot L/L_{12} \quad \text{Equation (5)}$$

Also, in this case, the rotation angle $\theta$ of the tip end of the catheter may be calculated by Equation (6).

$$\theta=\theta_2-(\theta_2-\theta_1)*L/L_{12} \quad \text{Equation (6)}$$

Moreover, in the case where the second hole 1011 is on the patient side, the rotation angle $\theta$ of the tip end of the catheter when the catheter insertion length L is the length from the second hole 1011 to the tip end portion 15 of the catheter 10 may be calculated by Equation (7).

$$\theta=\theta_1-(\theta_1-\theta_2)\cdot(L+L_{12})/L_{12} \quad \text{Equation (7)}$$

<Presenting Unit 106>

A presenting unit 106 presents, to a user, the rotation angle $\theta$ of the tip end of the catheter 10 calculated by the catheter tip-end rotation angle calculation unit 105.

The presenting unit 106 is not a necessary structural element of the catheter tip-end rotation angle measurement apparatus 100, but is helpful to a surgeon, who is a user, in catheter manipulation when the presenting unit 106 presents the rotation angle $\theta$ of the tip end of the catheter 10 calculated by the catheter tip-end rotation angle calculation unit 105 to the user.

Figure 11A:
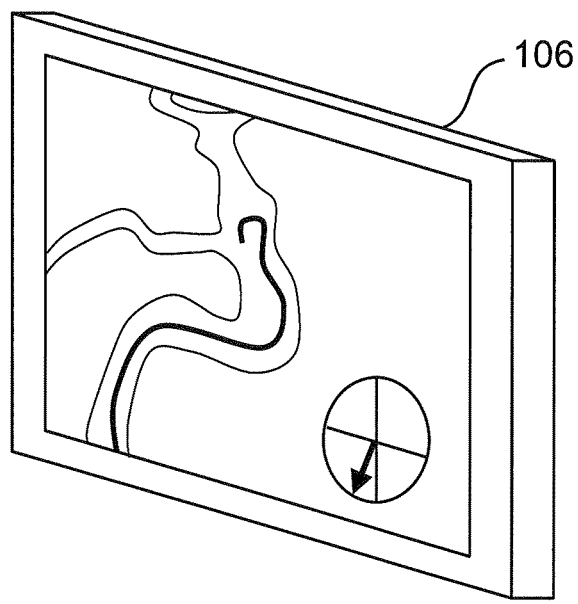
FIG. 11A is a view showing a state, according to the first embodiment, where an example of the rotation angle of the tip end of the catheter to be presented to a user is displayed on a display.

For example, the presenting unit 106 displays, on a display, the rotation angle $\theta$ of the tip end of the catheter 10 calculated by the catheter tip-end rotation angle calculation unit 105 in the form of a numerical value or the like. Three-dimensional representation using a CG or the like of the catheter 10 reflecting the rotation angle $\theta$ of the tip end of the catheter 10 is also possible. Moreover, the presenting unit 106 may display the rotation angle $\theta$ of the tip end of the catheter 10 by superimposing the same on an X-ray image displayed on a display which is monitored during catheter manipulation by a surgeon. FIG. 11A shows an example where the rotation angle $\theta$ of the tip end of the catheter 10 is displayed on the bottom right of the display by using an arrow.

<Operation>

Next, the operation of each structural element of the catheter tip-end rotation angle measurement apparatus 100 configured in the manner described above will be concretely described.

Figure 12:
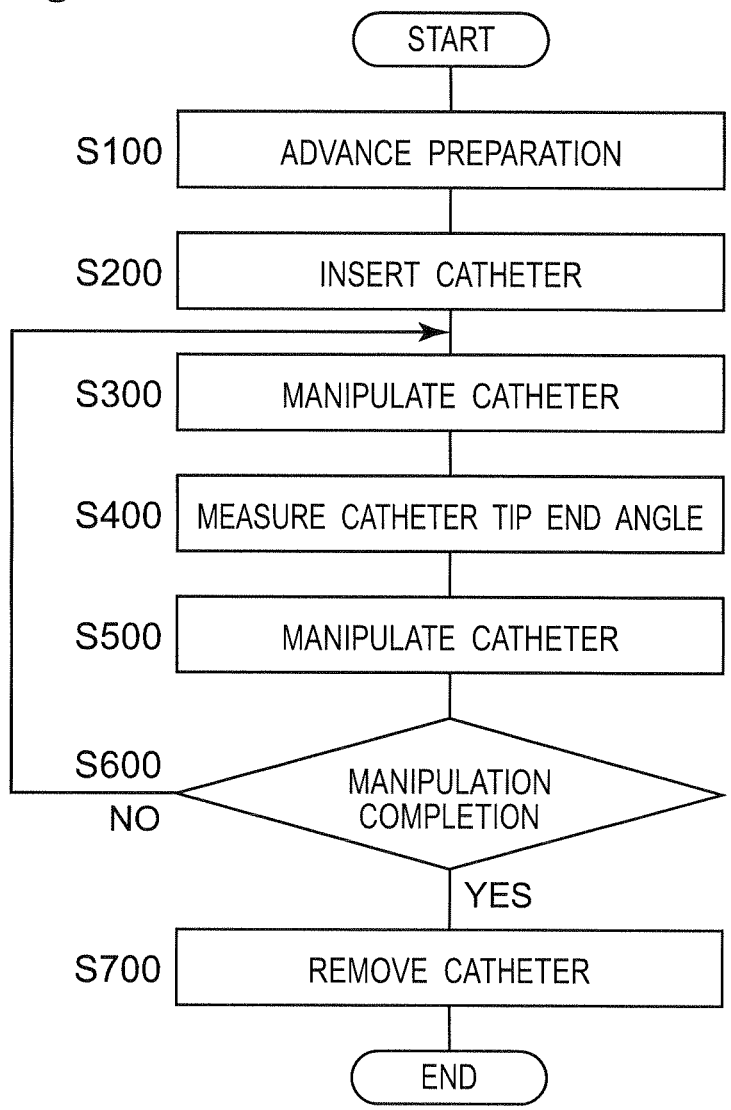
FIG. 12 is a flowchart showing an example of an operation of catheter treatment by a surgeon according to the first embodiment.

Before describing the operation of each structural element of the catheter tip-end rotation angle measurement apparatus 100, the overall flow of catheter treatment which is when the catheter tip-end rotation angle measurement apparatus 100 is used will be described. FIG. 12 shows the overall flow of a surgical treatment using a catheter.

<Step S100>

As an advance preparation for a surgical treatment, a surgeon sets initial values of the first rotation angle measurement unit 102, the second rotation angle measurement unit 103, and the catheter insertion length measurement unit 104 to zero. Also, the surgeon inputs the distance $L_{12}$ between the first hole 1010 and the second hole 1011 to the catheter tip-end rotation angle calculation unit 105. Then, the surgeon selects the catheter 10 suitable for the portion to be diagnosed or treated, passes the selected catheter 10 from the first hole 1010 of the movement restriction unit 101 to the second hole 1011 thereof, and further to the catheter insertion length measurement unit 104.

Additionally, with respect to "0" of the first rotation angle measurement unit 102 and the second rotation angle measurement unit 103, the direction that is orthogonal to the insertion direction of the catheter 10 and that is from the floor to the ceiling may be made zero, for example.

Moreover, the initial values of the first rotation angle measurement unit 102, the second rotation angle measurement unit 103, and the catheter insertion length measurement unit 104 are described to be set to zero, but they do not necessarily have to be zero. Each of the values may be measured based on a numerical value at the time of start of measurement and a numerical value during measurement.

<Step S200>

The surgeon inserts the catheter 10 into the patient.

<Step S300>

The surgeon manipulates the catheter 10 while monitoring the X-ray image of the catheter 10 shown on the display, and inserts the catheter 10 to the portion to be diagnosed or treated.

<Step S400>

In the case where the surgeon wishes to identify the direction of the tip end of the catheter 10, the surgeon performs input so as to start measurement of the rotation angle $\theta$ of the tip end of the catheter 10. As a device for receiving the input, a keyboard or a push-button may be cited, for example. When the input is received, the catheter tip-end rotation angle measurement apparatus 100 performs steps S410 to S450 described below, and presents the rotation angle of the tip end of the catheter 10 to the surgeon.

Additionally, measurement of the rotation angle of the tip end of the catheter 10 does not have to be started after an input, and measurement may be performed at predetermined time intervals.

<Step S500>

The surgeon continues the manipulation of the catheter 10 while referring to the rotation angle $\theta$ of the tip end of the catheter presented by the presenting unit 106 and the like.

<Step S600>

In the case where diagnosis or treatment is not completed, the surgeon performs step S300, and in the case where diagnosis or treatment is completed, the surgeon performs step S700.

<Step S700>

In the case where diagnosis or treatment is completed, the surgeon removes the catheter 10 from the patient, and ends the surgical treatment.

The operation described above is the overall catheter treatment. Next, an operation of the catheter tip-end rotation angle measurement apparatus 100 according to the first embodiment will be described.

The method of measuring the rotation angle $\theta$ of the tip end of the catheter 10 is merely for measuring the rotation angle θ of the tip end of the catheter 10. That is, this method does not include the catheter manipulation in step S500 which is performed by the surgeon based on the rotation angle θ of the tip end of the catheter measured in step S400. Accordingly, the method of measuring the rotation angle θ of the tip end of the catheter 10 is not a method of performing a surgical operation on a human body, and does not correspond to a method of performing a surgery on a human being.

Figure 13:
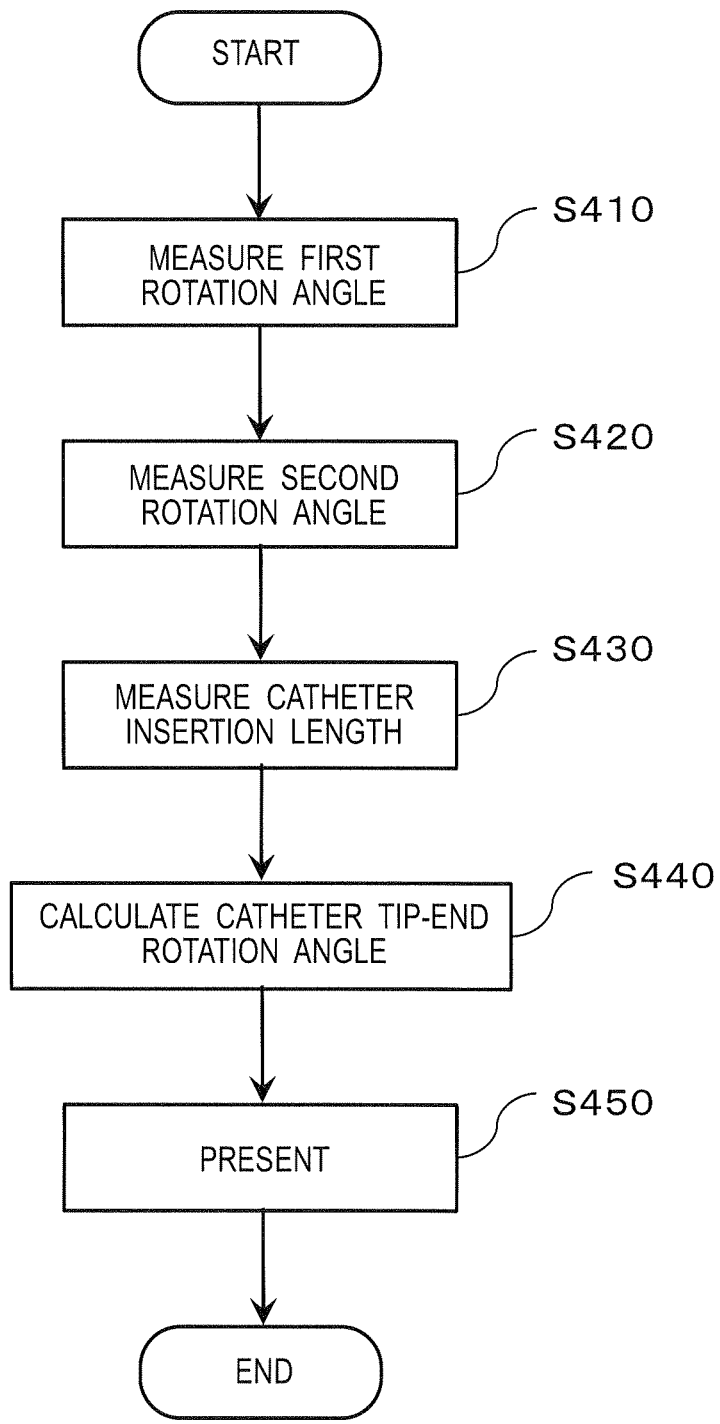
FIG. 13 is a flowchart showing an example of an operation of the catheter tip-end rotation angle measurement apparatus according to the first embodiment.

FIG. 13 shows a flow of the operation of the catheter tip-end rotation angle measurement apparatus 100 according to the first embodiment.

<Step S410>

The first rotation angle measurement unit 102 measures the first rotation angle, which is the rotation angle of the catheter 10 at the first hole 1010.

The concrete method of measuring the first rotation angle $\theta_1$ is as described above. Furthermore, the first rotation angle measurement unit 102 outputs the first rotation angle $\theta_1$ which has been measured, to the catheter tip-end rotation angle calculation unit 105.

<Step S420>

The second rotation angle measurement unit 103 measures the second rotation angle, which is the rotation angle of the catheter 10 at the second hole 1011.

The concrete method of measuring the second rotation angle $\theta_2$ is as described above. Furthermore, the second rotation angle measurement unit 103 outputs the second rotation angle $\theta_2$ which has been measured, to the catheter tip-end rotation angle calculation unit 105.

<Step S430>

The catheter insertion length measurement unit 104 measures the catheter insertion length, which is the length from the first hole 1010 to the tip end portion 15 of the catheter 10.

The concrete method of measuring the catheter insertion length L is as described above. Furthermore, the catheter insertion length measurement unit 104 outputs the catheter insertion length L which has been measured, to the catheter tip-end rotation angle calculation unit 105.

<Step S440>

The catheter tip-end rotation angle calculation unit 105 calculates the rotation angle θ of the tip end of the catheter by using the angle difference $(\theta_1-\theta_2)$ between the first rotation angle $\theta_1$ measured by the first rotation angle measurement unit 102 and the second rotation angle $\theta_2$ measured by the second rotation angle measurement unit 103, the catheter insertion length L measured by the catheter insertion length measurement unit 104, and the distance $L_{12}$ between the first hole 1010 and the second hole 1011.

First, the catheter tip-end rotation angle calculation unit 105 acquires each of the first rotation angle $\theta_1$ measured in step S410, the second rotation angle $\theta_2$ measured in step S420, and the catheter insertion length L measured in step S430.

Then, the catheter tip-end rotation angle calculation unit 105 calculates the angle difference $(\theta_1-\theta_2)$ between the first rotation angle $\theta_1$ and the second rotation angle $\theta_2$ from the first rotation angle $\theta_1$ and the second rotation angle $\theta_2$ which have been acquired.

Next, the catheter tip-end rotation angle calculation unit 105 calculates the rotation angle θ of the tip end of the catheter 10 by Equation (4) by using the angle difference $(\theta_1-\theta_2)$ between the first rotation angle $\theta_1$ and the second rotation angle $\theta_2$ which has been calculated, the catheter insertion length L which has been acquired, and the distance $L_{12}$ between the first hole 1010 and the second hole 1011 which has been set in step S100.

The catheter tip-end rotation angle calculation unit 105 outputs the rotation angle θ of the tip end of the catheter 10 which has been calculated, to the presenting unit 106.

<Step S450>

The presenting unit 106 acquires the rotation angle θ of the tip end of the catheter 10 which has been calculated in step S440, and presents the rotation angle θ of the tip end of the catheter 10 acquired, to the user.

The concrete method of presentation by the presenting unit 106 is as described above.

<Effect>

As described above, according to the catheter tip-end rotation angle measurement apparatus 100 of the first embodiment, in a case where the catheter 10 is uniformly twisted, the rotation angle of the tip end of the catheter 10 may be measured without mounting a rotation detection sensor or the like to the tip end of the catheter 10. Thus, since there is no need to mount the rotation detection sensor or the like to the tip end of the catheter 10, the possibility of damaging a blood vessel during manipulation of the catheter 10, which is a subtle, delicate manipulation, may be reduced. Also, with the rotation angle θ of the tip end of the catheter 10 which has been measured being presented to the user, the surgeon may accurately grasp the direction of the tip end of the catheter 10 based on the rotation angle θ of the tip end of the catheter 10 which has been measured. The surgeon is thereby enabled to easily align, at a branching portion of a blood vessel, the tip end of the catheter 10 with the branching direction of the target blood vessel or the like, and smooth catheter manipulation is enabled. Also, since smooth catheter manipulation may reduce the surgery time, the radiation time of X-rays radiated on a patient may be reduced. Thus, the dose of radiation to the patient by X-ray radiation may be lowered.

Figure 29:
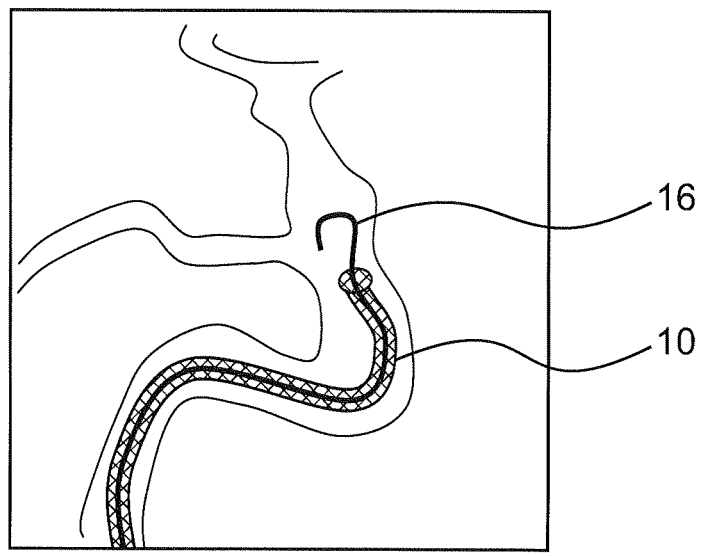
FIG. 29 is an explanatory view showing an example of a guide wire that is to be inserted before a catheter according to a modification example of the first embodiment.

Additionally, this first embodiment is also applied to a guide wire that is inserted before the catheter. FIG. 29 shows an example image of a case where a guide wire 16 is passed through the lumen of the catheter 10 inserted in a blood vessel, and where the guide wire 16 is moved forward in front of the catheter 10. Generally, in a blood vessel catheter treatment, the guide wire 16 precedes insertion of the catheter 10 so that the blood vessel wall is less likely to be damaged and so that the catheter 10 may be smoothly carried to the lesion area. Furthermore, the frictional resistance of the surface of the lumen of the catheter 10 is made small, or the surgeon injects a small amount of water into the lumen of the catheter 10 during treatment so as to facilitate passing of the guide wire. Thus, in a case where the guide wire 16 is twisted, a load is applied with respect to the rotation of the tip end of the guide wire 16, and the resulting twisting of the guide wire 16 is assumed to be uniformly caused in the lumen of the catheter 10.

Furthermore, the relationship described above may also be established between an outer catheter and an inner catheter. Here, the outer catheter is for facilitating guiding of the inner catheter and has a thickness of about 2 mm, and the inner catheter is for actually treating a lesion and, in many cases, the thickness thereof is 1 mm or less. By letting the inner catheter pass through the lumen of the outer catheter inserted into a blood vessel, the inner catheter may be smoothly carried to a lesion, and treatment of the lesion by the inner catheter, such as expansion of a narrowed blood vessel by a balloon, may be performed. Also in this case, in the case where the inner catheter is twisted, a load is applied with respect to the rotation of the tip end of the inner catheter, and the resulting twisting of the inner catheter is assumed to be uniformly caused in the lumen of the outer catheter.

Accordingly, the catheter tip-end rotation angle measurement apparatus 100 of this first embodiment may be effectively used especially with respect to a guide wire which is inserted before the catheter, or the inner catheter which is inserted before the outer catheter.

Second Embodiment

A catheter tip-end rotation angle measurement apparatus 200 according to a second embodiment is different from the catheter tip-end rotation angle measurement apparatus 100 of the first embodiment in that the catheter tip-end rotation angle measurement apparatus 200 detects the motion of the tip end portion 15 of the catheter 10, and in the case where movement is detected, the rotation angle θ of the tip end of the catheter 10 is calculated, and in the case where movement is not detected, the rotation angle θ of the tip end of the catheter 10 is not calculated. In the following, differences to the first embodiment will be mainly described.

Figure 14:
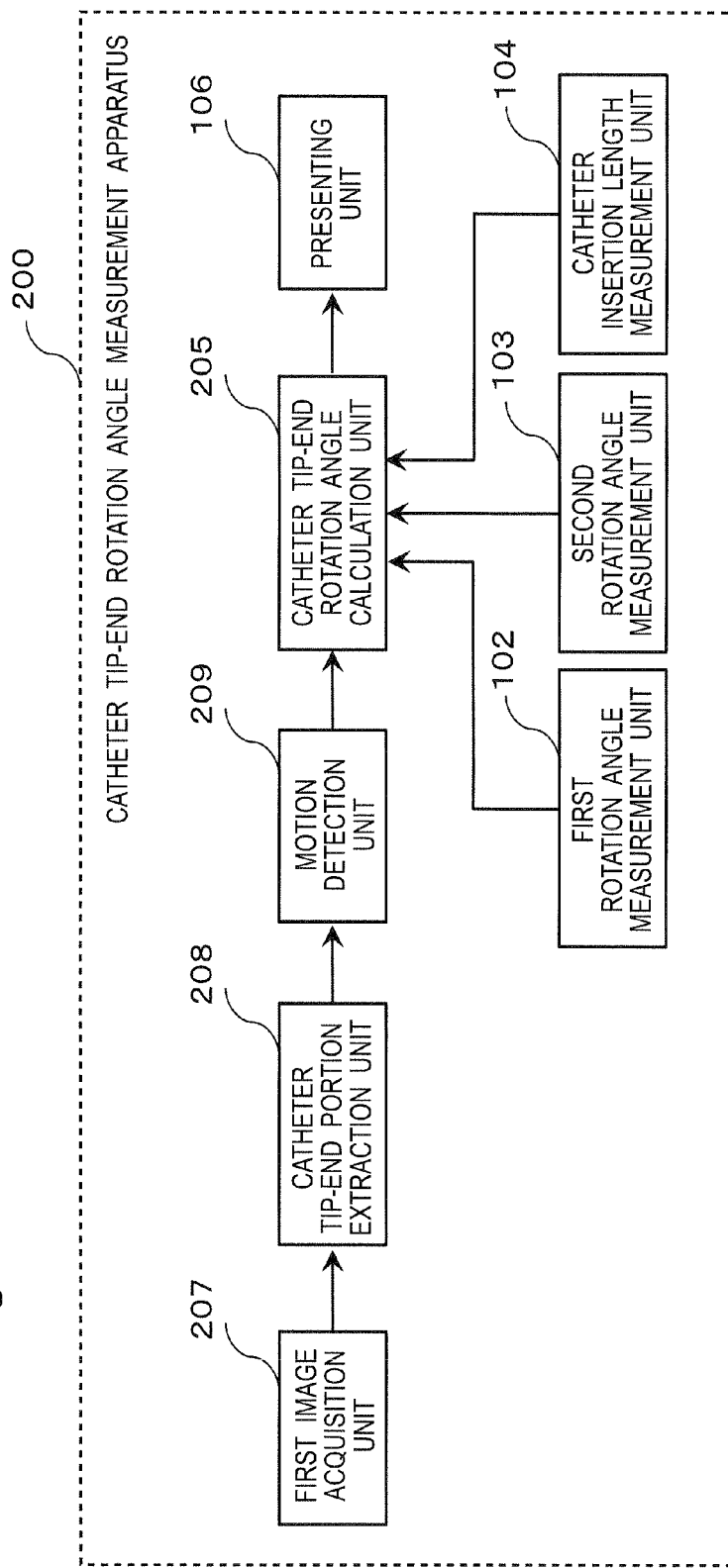
FIG. 14 is a block diagram showing a functional configuration of a catheter tip-end rotation angle measurement apparatus according to a second embodiment.

FIG. 14 shows a functional configuration of the catheter tip-end rotation angle measurement apparatus 200 according to the second embodiment. Additionally, in FIG. 14, structural elements the same as those in FIG. 1 are denoted by the same reference numerals, and description thereof will be omitted as appropriately.

As shown in FIG. 14, the catheter tip-end rotation angle measurement apparatus 200 includes the first rotation angle measurement unit 102, the second rotation angle measurement unit 103, the catheter insertion length measurement unit 104, a catheter tip-end rotation angle calculation unit 205, a presenting unit 106, a first image acquisition unit 207, a catheter tip-end portion extraction unit 208, and a motion detection unit 209. Although not shown in FIG. 14, the movement restriction unit 101 is included. In the following, each structural element of the catheter tip-end rotation angle measurement apparatus 200 will be described.

<Configuration>
<First Image Acquisition Unit 207>

The first image acquisition unit 207 acquires an X-ray image 30 captured by an X-ray image capturing device 20 for image-capturing a region including a tip end portion of the catheter 10 inserted into a body lumen.

Figure 15:
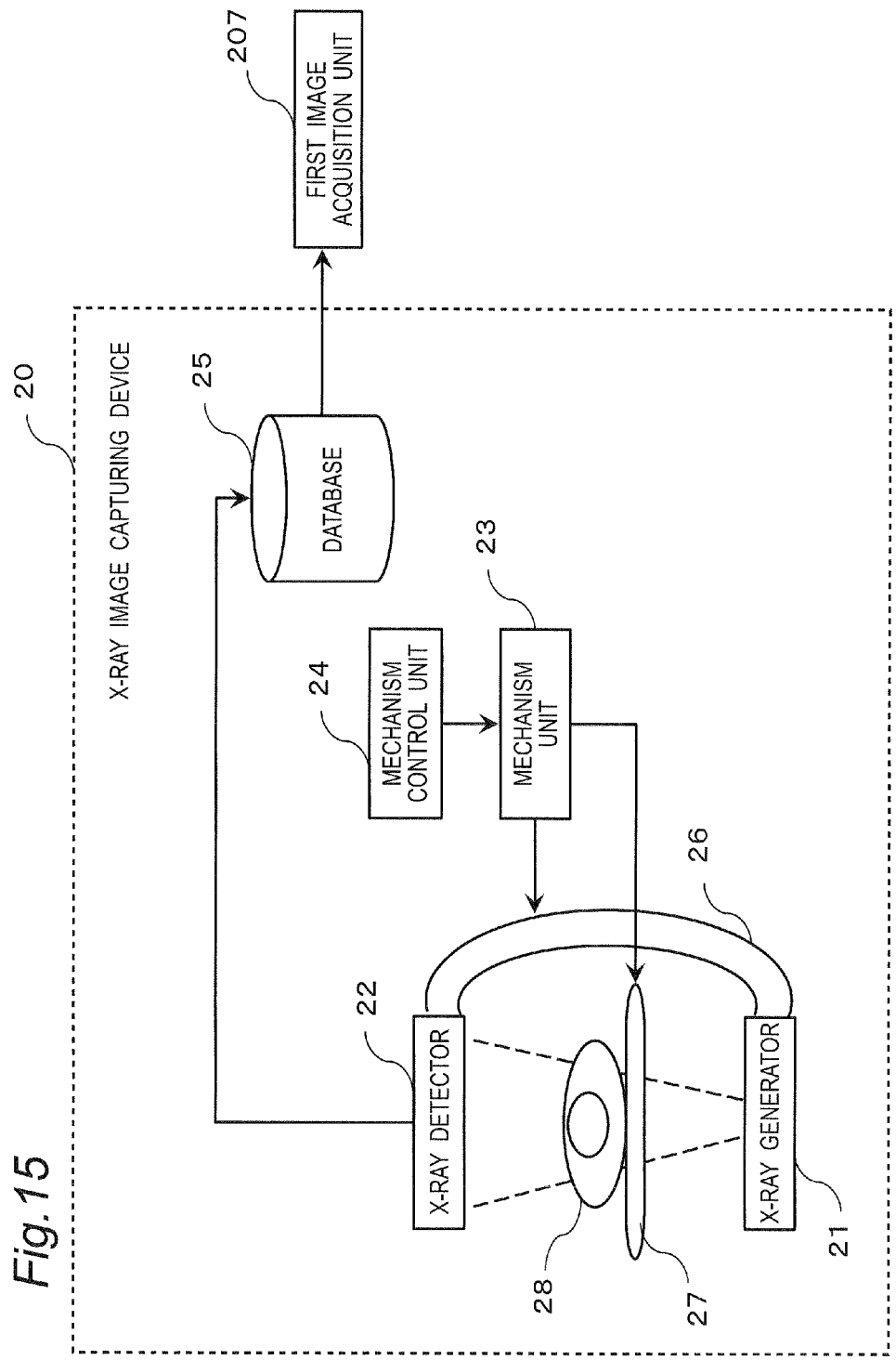
FIG. 15 is a schematic view showing a functional configuration of an X-ray image capturing device according to the second embodiment.

FIG. 15 shows configurations of the first image acquisition unit 207 and the X-ray image capturing device 20. Here, the X-ray image capturing device 20 is a device for acquiring an X-ray image captured by radiating X-rays to an image-capturing target portion of a patient or a blood vessel image captured at the time of injection of a contrast medium, and is called an X-ray blood vessel imaging device or an angiogram, for example.

The X-ray image capturing device 20 includes an X-ray generator 21, an X-ray detector 22, a mechanism unit 23, a mechanism control unit 24, an arm 26, and a database 25. The X-ray generator 21 includes an X-ray tube for generating X-rays by using high voltage, and an X-ray diaphragm for controlling a radiation field by blocking a part of the X-rays, and radiates X-rays on a patient 28 on a bed 27. The X-ray detector 22 is for receiving X-rays which have passed through the patient 28 and recording image information, and for outputting the recorded image information, and is configured as an FPD (Flat Panel Detector) which arranges an X-ray sensitive layer and which converts X-rays into digital data and outputs the data, for example. Furthermore, when X-rays are radiated, the X-ray detector 22 outputs image information indicating the X-ray image 30 obtained by the radiation to the database 25. The mechanism unit 23 moves the arm 26 and the bed 27 based on instructions from the mechanism control unit 24 which have received manipulation instructions from a surgeon. The first image acquisition unit 207 reads the X-ray image or X-ray video stored in the database 25, and outputs the same to the catheter tip-end portion extraction unit 208.

Figure 16:
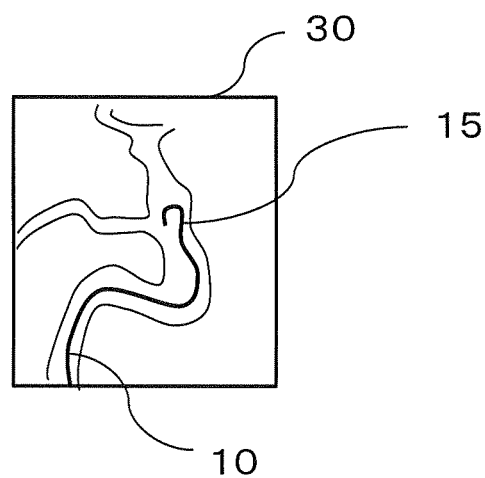
FIG. 16 is a view showing an example of an X-ray image captured by the X-ray image capturing device according to the second embodiment.

FIG. 16 shows an example of the X-ray image 30 of the catheter 10 acquired by the first image acquisition unit 207. The tip end portion 15 of the catheter 10 is a portion including the bent portion 15 shown in FIG. 9, and is a portion, from the tip end of the catheter 10, of about 1 to 2 cm in addition to a length La of the bent portion 15, for example. Additionally, the tip end portion 15 of the catheter may be the same portion as the bent portion 15.

<Catheter Tip-End Portion Extraction Unit 208>

The catheter tip-end portion extraction unit 208 extracts the tip end portion 15 of the catheter from the X-ray image 30 acquired by the first image acquisition unit 207.

Figure 17:
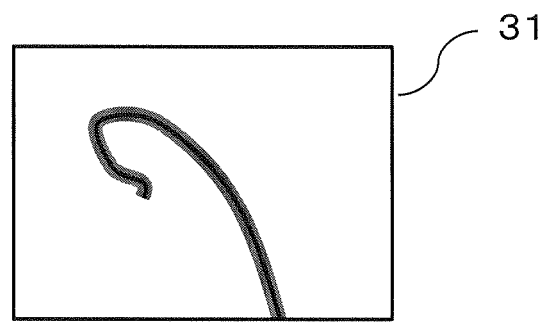
FIG. 17 is a view showing an example of a tip end of a catheter extracted by a catheter tip end extraction unit according to the second embodiment.

In the following, a concrete method of the catheter tip-end portion extraction unit 208 to extract the tip end portion 15 of the catheter will be described. The catheter tip-end portion extraction unit 208 compares the X-ray image 30 acquired and an X-ray image of a previous frame, and extracts only the parts where the brightness has changed to darker on a per-pixel basis. Accordingly, the tip end portion 15 of the catheter may be extracted only when there is a motion of the catheter 10. For example, the brightness of a pixel takes a value between "0" and "255", and when "0" is the darkest and "255" is the brightest, pixels whose values obtained by subtracting the pixels of the current frame of the X-ray image 30 from the pixels of the previous frame are "50" or more are assumed to be parts of the catheter 10 and are set to "0", and other pixels are assumed to be parts other than the catheter 10 and are set to "255". By such binarization, the tip end portion 15 of the catheter 10 may be extracted. FIG. 17 shows an image of the tip end portion 15 of the catheter 10 extracted by the catheter tip-end portion extraction unit 208.

Additionally, the catheter tip-end portion extraction unit 208 may perform comparison to a frame of a predetermined time before (for example, one second before).

Moreover, without being restricted to the method described above, the catheter tip-end portion extraction unit 208 may decide the degree of linearity of the catheter 10, identify a part where the value of the degree of linearity is low as the bent portion 15, and extract a predetermined region including the identified bent portion 15 as the tip end portion 15 of the catheter 10.

<Motion Detection Unit 209>

The motion detection unit 209 detects the motion of the tip end portion 15 of the catheter 10 extracted by the catheter tip-end portion extraction unit 208. The motion detection unit 209 may indirectly detect motion, such as insertion or rotation, of a base portion by detecting the motion of the tip end portion 15 of the catheter 10. The base portion here is a portion including the movement restriction unit 101 and the catheter insertion length measurement unit 104.

Figure 18:
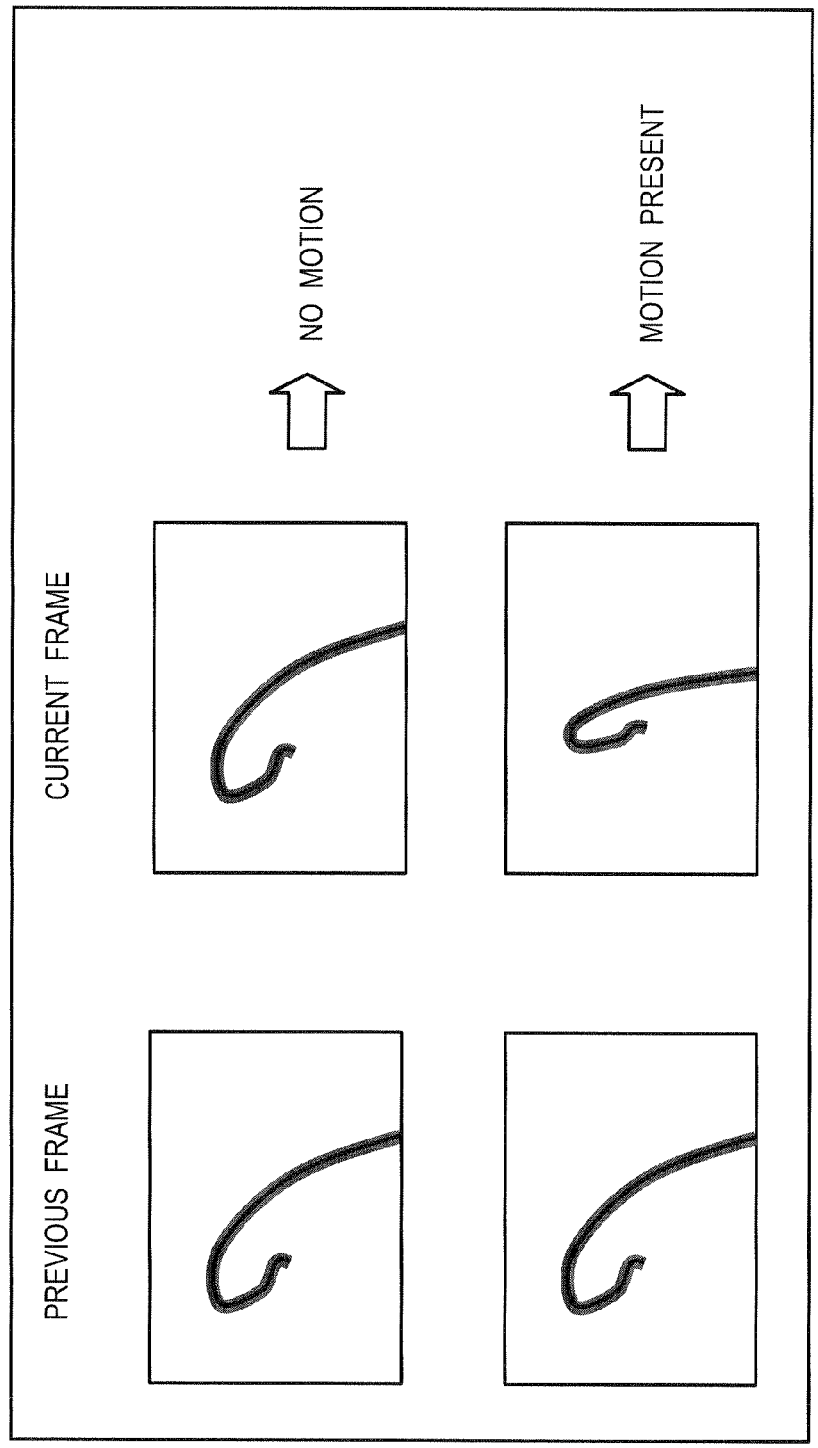
FIG. 18 is an explanatory view showing an example of an operation of a motion detection unit according to the second embodiment.

In the following, a concrete method of the motion detection unit 209 to detect the motion of the tip end portion 15 will be described. In extracting the tip end portion 15 of the catheter 10, the motion detection unit 209 extracts motion of the tip end portion 15 in a case where the number of pixels whose brightness has changed is a predetermined number of pixels or more. For example, the motion detection unit 209 extracts motion of the tip end portion 15 in a case where the brightness is "0" and the number of pixels is "10" or more. Furthermore, when the motion detection unit 209 extracts the tip end portion 15 of the catheter 10, if there is no movement of the tip end portion 15 of the catheter 10, all the pixels are extracted as the brightness "255", and motion of the tip end portion 15 is not detected. FIG. 18 shows presence/absence of motion of the tip end portion 15 of the catheter 10 detected by the motion detection unit 209 based on comparison of a previous frame and a current frame.

Moreover, without being restricted to the method described above, the motion detection unit 209 may compare, at predetermined intervals (for example, intervals of 1 ms), the tip end portions 15 whose contours have been extracted from the X-ray images 30, and motion may be detected in a case where there is a change of a predetermined value (for example, 0.03 mm) or more, and motion may not be detected in a case where there is no change of the predetermined value or more.

<Catheter Tip-End Rotation Angle Calculation Unit 205>

The catheter tip-end rotation angle calculation unit 205 calculates the rotation angle θ of the tip end of the catheter by using the angle difference $(\theta_1-\theta_2)$ between the first rotation angle $\theta_1$ measured by the first rotation angle measurement unit 102 and the second rotation angle $\theta_2$ measured by the second rotation angle measurement unit 103, the catheter insertion length L measured by the catheter insertion length measurement unit 104, and the distance $L_{12}$ between the first hole 1010 and the second hole 1011.

Also, the catheter tip-end rotation angle calculation unit 205 calculates the rotation angle θ of the tip end of the catheter 10 in a case where motion is detected by the motion detection unit 209, and does not calculate the rotation angle θ of the tip end of the catheter 10 in a case where motion is not detected by the motion detection unit 209.

Additionally, the concrete method of calculating the rotation angle θ of the tip end of the catheter 10 that is calculated by the catheter tip-end rotation angle calculation unit 205 is the same as the calculation method of the catheter tip-end rotation angle calculation unit 105 according to the first embodiment.

<Operation>

Figure 19:
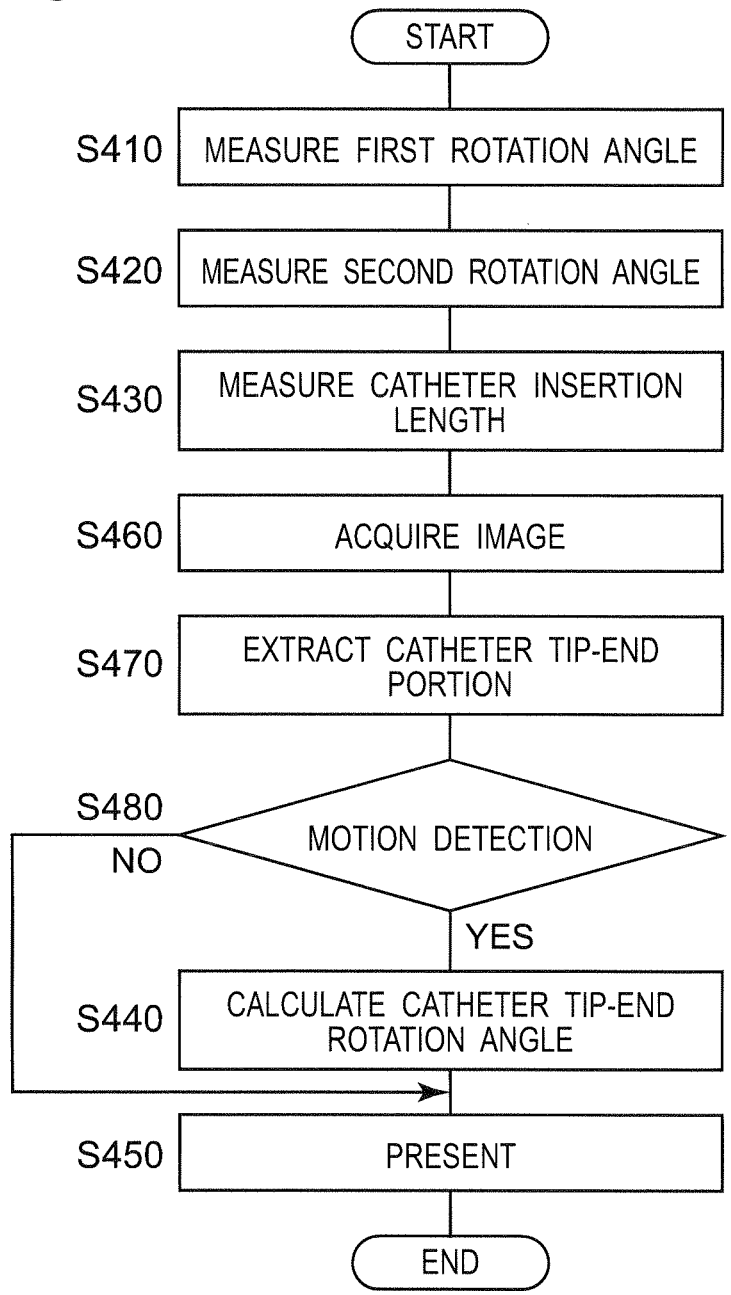
FIG. 19 is a flowchart showing an example of an operation of the catheter tip-end rotation angle measurement apparatus according to the second embodiment.

Next, the operation of each structural element of the catheter tip-end rotation angle measurement apparatus 200 configured in the above manner will be specifically described. FIG. 19 shows a flow of the operation of the catheter tip-end rotation angle measurement apparatus 200 according to the second embodiment. Additionally, in FIG. 19, steps the same as those in FIG. 13 are denoted by the same reference numerals, and description thereof will be omitted as appropriately.

<Step S460>

The first image acquisition unit 207 acquires an X-ray image 30 captured by the X-ray image capturing device 20 from the database 25.

The concrete method of image acquisition is as described above. Furthermore, the first image acquisition unit 207 outputs the X-ray image 30 acquired, to the catheter tip-end portion extraction unit 208.

<Step S470>

The catheter tip-end portion extraction unit 208 extracts the tip end portion 15 of the catheter 10 from the X-ray image 30 acquired by the first image acquisition unit 207.

First, the catheter tip-end portion extraction unit 208 acquires the X-ray image 30 acquired in step S460. Then, the catheter tip-end portion extraction unit 208 extracts the tip end portion 15 of the catheter 10 from the X-ray image 30 which has been acquired. The concrete method of extracting the tip end portion 15 is as described above. Next, the catheter tip-end portion extraction unit 208 outputs the tip end portion 15 which has been extracted, to the motion detection unit 209.

<Step S480>

The motion detection unit 209 detects motion of the tip end portion 15 of the catheter extracted by the catheter tip-end portion extraction unit 208.

First, the motion detection unit 209 acquires the tip end portion 15 extracted in step S470. Then, the motion detection unit 209 detects the motion of the tip end portion 15 which has been acquired. The concrete method of detecting motion of the tip end portion 15 is as described above. Next, the motion detection unit 209 performs step S440 in a case where motion of the tip end portion 15 is detected, and performs step S450 in a case where motion of the tip end portion 15 is not detected. That is, in the case where motion of the tip end portion 15 is not detected by the motion detection unit 209, the presenting unit 106 keeps presenting, to the user, the rotation angle θ of the tip end of the catheter 10 that is currently presented. Accordingly, in the case where there is no motion of the tip end portion 15, even if the first rotation angle $\theta_1$, the second rotation angle $\theta_2$, and the catheter insertion length L have changed, these changes are assumed to be small, and the amount of change of each parameter is assumed to be "0".

<Effect>

As described above, according to the catheter tip-end rotation angle measurement apparatus 200 of the second embodiment, when motion of the tip end portion 15 of the catheter 10 is detected, the rotation angle θ of the tip end of the catheter 10 is measured. Thus, the surgeon may grasp, in real time with his/her catheter manipulation, the rotation angle θ of the tip end of the catheter 10. The surgeon is thereby enabled to easily align, at a branching portion of a blood vessel, the tip end of the catheter 10 with the branching direction of the target blood vessel or the like, and smooth catheter manipulation is enabled. Also, since smooth catheter manipulation may reduce the surgery time, the radiation time of X-rays radiated on a patient may be reduced. Thus, the dose of radiation to the patient by X-ray radiation may be lowered.

Third Embodiment

A catheter tip-end rotation angle measurement apparatus 300 according to a third embodiment is different from the catheter tip-end rotation angle measurement apparatus 100 according to the first embodiment in that the catheter tip-end rotation angle measurement apparatus 300 is capable of accurately measuring the rotation angle of the tip end of a catheter 10 even in a case where a part of the catheter 10 is twisted. In the following, differences to the first embodiment will be mainly described.

Figure 20:
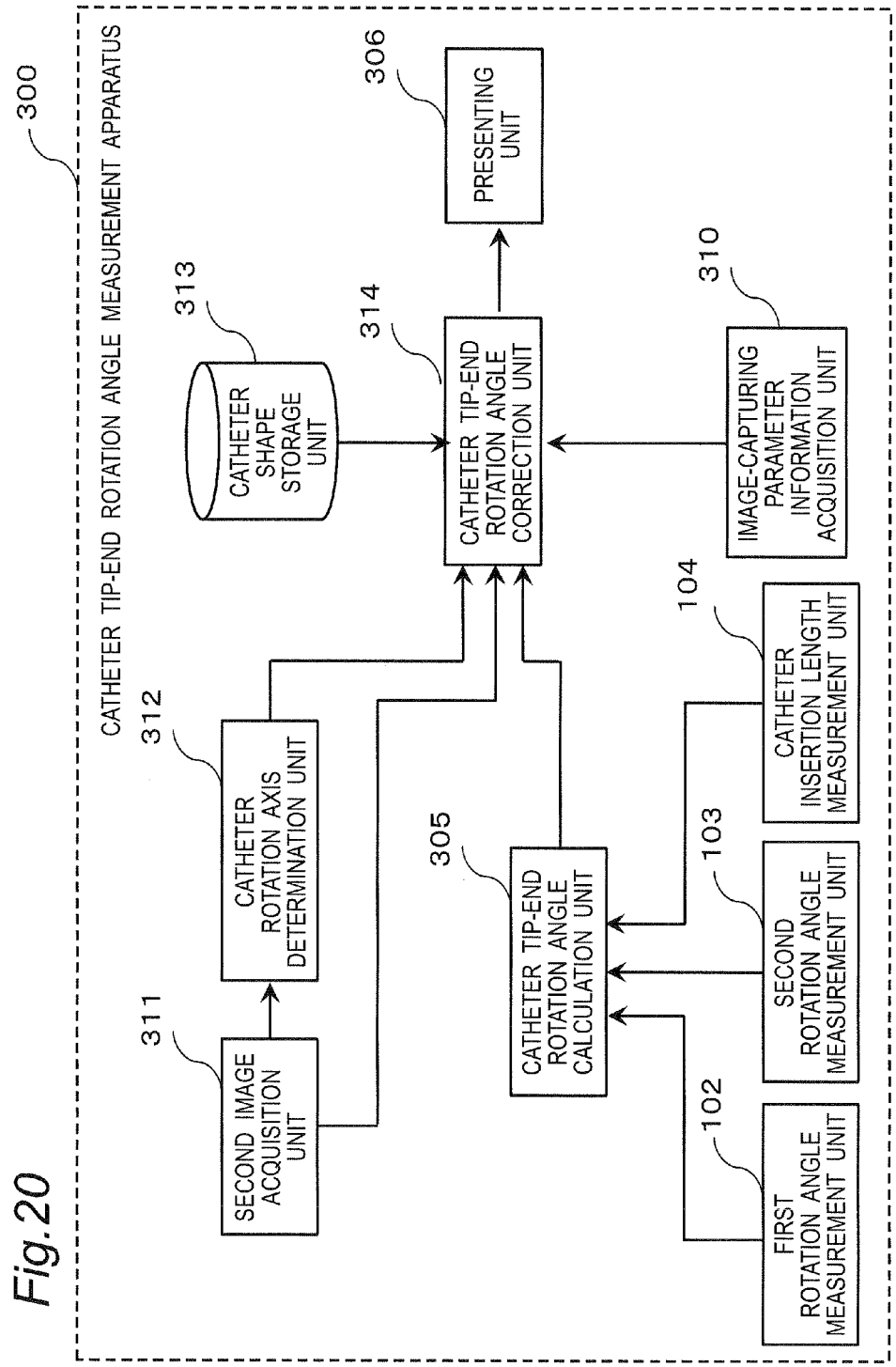
FIG. 20 is a block diagram showing a functional configuration of a catheter tip-end rotation angle measurement apparatus according to a third embodiment.

FIG. 20 shows a functional configuration of the catheter tip-end rotation angle measurement apparatus 300 according to the third embodiment. Additionally, in FIG. 20, structural elements the same as those in FIG. 1 are denoted by the same reference numerals, and description thereof will be omitted as appropriately.

As shown in FIG. 20, the catheter tip-end rotation angle measurement apparatus 300 includes the first rotation angle measurement unit 102, the second rotation angle measurement unit 103, the catheter insertion length measurement unit 104, a catheter tip-end rotation angle calculation unit 305, a presenting unit 306, an image-capturing parameter information acquisition unit 310, a second image acquisition unit 311, a catheter rotation axis determination unit 312, a catheter shape storage unit 313, and a catheter tip-end rotation angle correction unit 314. Also, the movement restriction unit 101, not shown, is included. In the following, each structural element of the catheter tip-end rotation angle measurement apparatus 300 will be described.

<Configuration>
<Image-Capturing Parameter Information Acquisition Unit 310>

The image-capturing parameter information acquisition unit 310 acquires image-capturing parameter information which is information about image-capturing conditions and orientation of each X-ray image capturing device 20 at the time of image-capturing.

The image-capturing parameter information includes a device parameter (an internal parameter) of the X-ray image capturing device 20, and a position/orientation parameter (an external parameter) of the X-ray image capturing device 20 at the time of image-capturing. More specifically, the internal parameter is a parameter regarding capturing by the X-ray image capturing device 20, and includes shutter speed, an aperture value, an exposure correction value, an ISO sensitivity value, a white balance setting value, a recording image size, recording image quality, and other parameters that affect image forming. Also, the external parameter is a parameter regarding the position or direction of the X-ray image capturing device 20 at the time of capturing, and for example, in the case where an origin and directions of X, Y, and Z axes in a space are determined, the position of the X-ray image capturing device 20 is expressed by (x, y, z).

The image-capturing parameter information acquisition unit 310 externally outputs the image-capturing parameter information which has been acquired, as a perspective projection matrix.

Here, the perspective projection matrix is described. When a point X in a three-dimensional space is projected onto a point m in a two-dimensional perspective image, this projection may be expressed by Equation (8) using homogeneous coordinates.

$$\lambda \begin{bmatrix} u \\ v \\ 1 \end{bmatrix} = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix} \begin{bmatrix} X \\ Y \\ Z \\ 1 \end{bmatrix} \quad \text{Equation (8)}$$

Perspective projection matrix $$P = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix}$$

Point in perspective image $m = [u, v, 1]^T$

Point in three-dimensional space $X = [X, Y, Z, 1]^T$

Here, the image point m in Equation (8) is a 3×1 vector and the three-dimensional point X is a 4×1 vector, and a matrix P of a 3×4 matrix is called a perspective projection matrix or a projection matrix. Here, λ is a real number indicating uncertainty in a constant factor. The projection matrix P indicates a geometric relationship such as a focal distance at the time of perspective image capturing, three-dimensional rotation and translation from a three-dimensional space coordinate system to a perspective image coordinate system, and the like.

<Second Image Acquisition Unit 311>

The second image acquisition unit 311 image-captures a region including the end tip portion 15 of the catheter 10 inserted into a body lumen, and acquires a plurality of X-ray images 30 captured by a plurality of X-ray image capturing devices 20 provided at different positions.

The second image acquisition unit 311 is configured in approximately the same way as the first image acquisition unit 207. The second image acquisition unit 311 acquires a plurality of X-ray images 30 captured by a plurality of X-ray image capturing devices 20 provided at different positions. The plurality of X-ray image capturing devices 20 provided at different positions are biplane-type X-ray image capturing devices each including two sets of X-ray generators 21 and X-ray detectors 22 with an image-capturing angle difference of 90 degrees and each being capable of capturing two X-ray images at the same time, for example. Also, "different positions" means cases excluding a case where the X-ray detectors 22 are installed at the same position and a case where the X-ray detectors 22 are installed at facing positions, and it is sufficient if the angle difference between the X-ray detectors 22 is 5 degrees or more.

<Catheter Rotation Axis Determination Unit 312>

The catheter rotation axis determination unit 312 extracts a part of the catheter 10 which is a straight line in each X-ray image from the plurality of X-ray images acquired by the second image acquisition unit 311, reconstructs the three-dimensional shape of the catheter 10 by using the part of the catheter 10 which is a straight line which has been extracted and the image-capturing parameter information at the time of capturing of each X-ray image acquired by the image-capturing parameter information acquisition unit 310, and determines the rotation axis with respect to the insertion direction of the catheter 10 based on the three-dimensional shape of the catheter 10 which has been reconstructed. Also, the catheter rotation axis determination unit 312 externally outputs the rotation axis which has been determined and the X-ray image acquired by the second image acquisition unit 311.

The catheter rotation axis determination unit 312 extracts a part of the catheter 10 which is a straight line in each X-ray image 30 from the plurality of X-ray images acquired by the second image acquisition unit 311. In the following, a concrete extraction method will be described assuming a case where two X-ray images 30 are acquired by the second image acquisition unit 311.

The catheter rotation axis determination unit 312 acquires two X-ray images 30 with an angle difference, from the second image acquisition unit 311. The catheter rotation axis determination unit 312 extracts a part of the catheter 10 which is a straight line with respect to each of the two X-ray images 30 which have been acquired. A part of the catheter 10 which is a straight line here is a part not including the bent portion 15 of the catheter 10, as shown in FIG. 9, that is, a straight line portion 14. The catheter rotation axis determination unit 312 decides the degree of linearity of the catheter 10, identifies a part with a predetermined degree of linearity or more as the straight line portion 14, and extracts a predetermined region including the straight line portion 14 which has been identified as a part of the catheter 10 which is a straight line.

Figure 21:
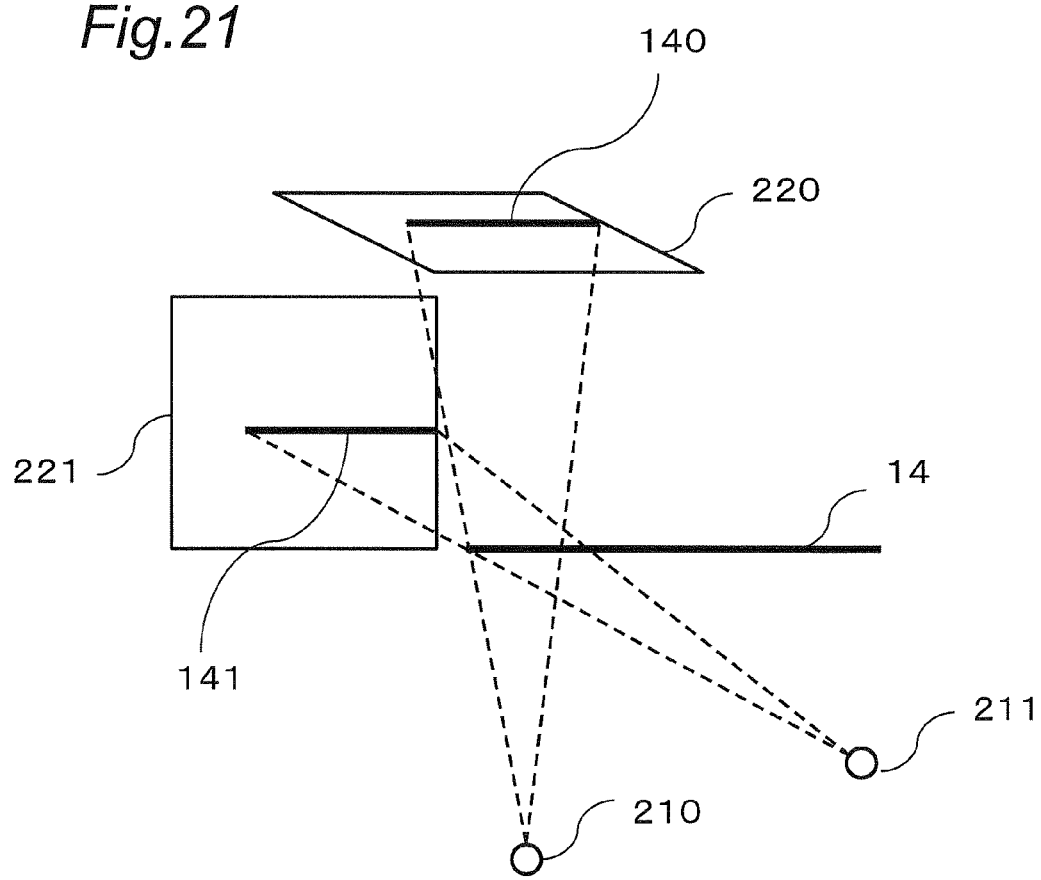
FIG. 21 is an explanatory view showing an example of a method of determining a rotation axis of a catheter according to the third embodiment.

FIG. 21 shows a schematic view regarding determination of the rotation axis of the catheter 10.

First, the catheter rotation axis determination unit 312 acquires, from two X-ray images 30, a straight line portion image 140 and a straight line portion image 141, which are images extracting the parts of the catheter 10 which are straight lines. Also, the catheter rotation axis determination unit 312 acquires, from the image-capturing parameter information acquisition unit 310, pieces of image-capturing parameter information of an X-ray generator 210 and an X-ray generator 211, and an X-ray detector 220 and an X-ray detector 221 at the time of acquisition of the straight line portion image 140 and the straight line portion image 141.

Next, the catheter rotation axis determination unit 312 performs reconstruction of a three-dimensional shape of the part of the catheter 10 which is a straight line by using the two straight line portion images 140 and 141 and two sets of pieces of image-capturing parameter information. The concrete method of reconstruction of a three-dimensional shape is as described below.

First, to extract corresponding points on the two images, a Fundamental matrix indicating the geometric relationship of the two images is calculated based on the image-capturing parameter information and by using Equation (9).

$$F=[P'C] \times P'P^- \quad \text{Equation (9)}$$

F: Fundamental matrix
P: Projection matrix of X-ray generator (reference numeral) and X-ray detector (reference numeral)
P': Projection matrix of X-ray generator (reference numeral) and X-ray detector (reference numeral)
C: Image-capturing viewpoint of X-ray tube (1) (Null space of P)

Figure 26:
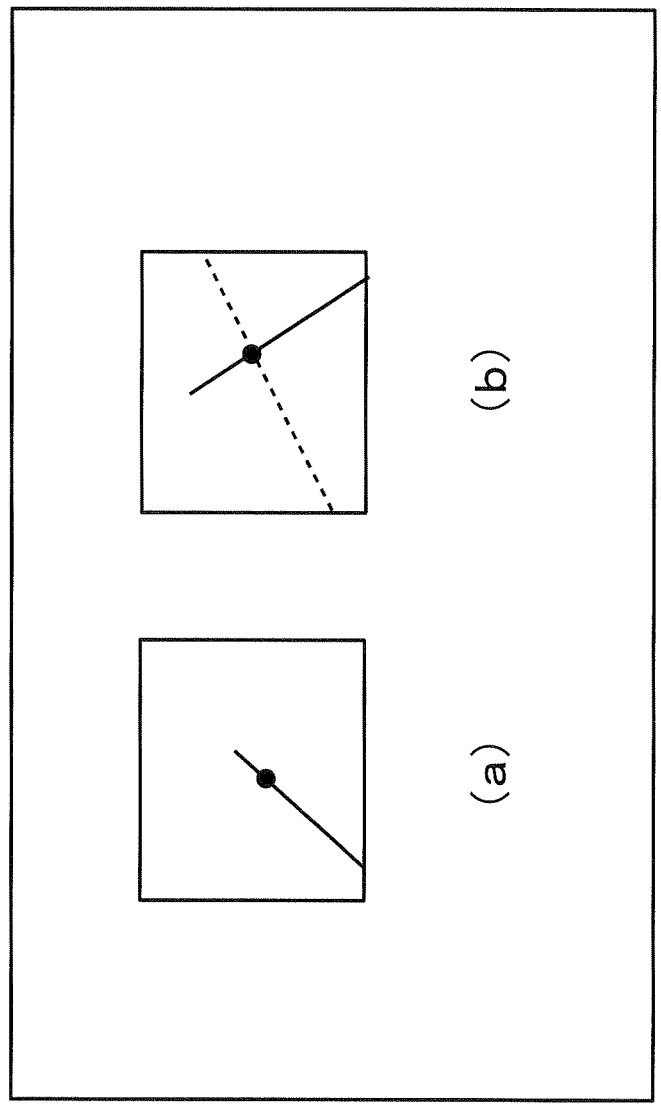
FIG. 26 is an explanatory view showing a way of calculating an epipolar line at a time of obtaining a rotation axis of the catheter according to the third embodiment.

Next, by using Equation (10), an epipolar line is calculated with respect to a point on the straight line in the straight line portion image 140 obtained by the X-ray generator 210 and the X-ray detector 220. FIG. 26 schematically shows the epipolar line. As shown in FIG. 26, (a) in the figure shows a point on the straight line in the straight line portion image 140, and the dotted line in (b) in the figure is the epipolar line with respect to the point on the straight line.

$$l'=Fm \quad \text{Equation (10)}$$

F: Fundamental matrix
l': Epipolar line of X-ray detector (reference numeral) corresponding to point m in perspective image of X-ray detector (reference numeral)
m: Point in perspective image of X-ray detector (reference numeral)

Here, the epipolar line indicates the existing range in the straight line portion image 140. Accordingly, by calculating the point of intersection of the epipolar line and the extracted straight line, the corresponding points of the straight line portion image 140 and the straight line portion image 141 may be calculated. A projection formula such as Equation (8) is established between the image-capturing parameter information (the projection matrix of each X-ray tube) and the corresponding points of the straight line portion image 140 and the straight line portion image 141, and thus, modification to Equation (11) may be performed if the projection formulae are put together with respect to the three-dimensional point X.

$$\begin{bmatrix} p_{31}u - p_{11} & p_{32}u - p_{12} & p_{33}u - p_{13} \\ p_{31}v - p_{21} & p_{32}v - p_{22} & p_{33}v - p_{23} \\ p'_{31}u' - p'_{11} & p'_{32}u' - p'_{12} & p'_{33}u' - p'_{13} \\ p'_{31}v' - p'_{21} & p'_{32}v' - p'_{22} & p'_{33}v' - p'_{23} \end{bmatrix} \quad \text{Equation (11)}$$

-continued $$\begin{bmatrix} X \\ Y \\ Z \end{bmatrix} = \begin{bmatrix} p_{14} - p_{34}u \\ p_{24} - p_{34}v \\ p'_{14} - p'_{34}u' \\ p'_{24} - p'_{34}v' \end{bmatrix}$$

$$MX = b$$

Accordingly, by using Equation (12) obtained by modifying Equation (11), the three-dimensional point may be reconstructed based on the image-capturing parameter information (each projection matrix) and the corresponding points of the straight line portion image 140 and the straight line portion image 141. Here, M is an abbreviation of the 4×3 matrix on the left-hand side of Equation (11), and b is an abbreviation of the 4×1 matrix on the right-hand side of Equation (11).

$$X = M^+ b \quad \text{Equation (12)}$$

$M^+$: Generalized inverse matrix of M

Figure 22:
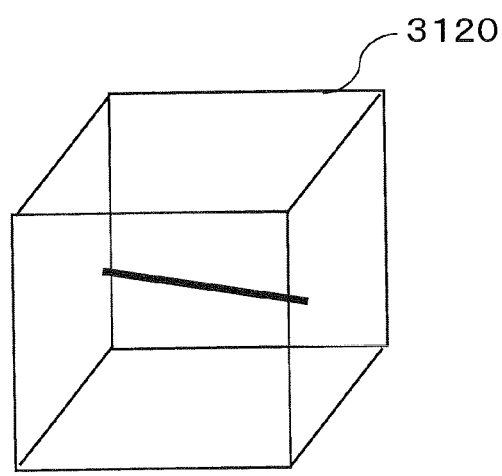
FIG. 22 is a view showing an example of a three-dimensional shape of a catheter reconstructed by a catheter rotation axis determination unit according to the third embodiment.

By performing this process on a plurality of points on the straight line extracted from the straight line portion image 140, a three-dimensional straight line may be calculated. FIG. 22 shows a three-dimensional straight line of the catheter 10 which has been reconstructed.

The catheter rotation axis determination unit 312 determines the rotation axis with respect to the insertion direction of the catheter 10 based on the three-dimensional shape of the catheter 10 which has been reconstructed by the method described above.

<Catheter Shape Storage Unit 313>

The catheter shape storage unit 313 stores, for a plurality of types of catheters 10, the shape of the tip end of the catheter 10 for each rotation angle of the tip end of the catheter 10.

There are many types of catheters 10 or guide wires to be inserted before catheters, and there are various shapes according to the usage. For example, there is a catheter called Judkins for the right coronary artery or the left coronary artery, and the tip end is bent in accordance with the anatomical location to facilitate insertion.

The catheter shape storage unit 313 stores in advance models for various corresponding three-dimensional shapes. Then, a surgeon or a radiology technician who handles radiology equipment sets the type of the catheter 10 or the guide wire in the catheter shape storage unit 313 in advance before insertion of the catheter 10 or the guide wire.

<Catheter Tip-End Rotation Angle Calculation Unit 305>

The catheter tip-end rotation angle calculation unit 305 calculates the rotation angle θ of the tip end of the catheter by using the angle difference $(\theta_1 - \theta_2)$ between the first rotation angle $\theta_1$ measured by the first rotation angle measurement unit 102 and the second rotation angle $\theta_2$ measured by the second rotation angle measurement unit 103, the catheter insertion length L measured by the catheter insertion length measurement unit 104, and the distance $L_{12}$ between the first hole 1010 and the second hole 1011. Also, the catheter tip-end rotation angle calculation unit 305 externally outputs the second rotation angle $\theta_2$ measured by the second rotation angle measurement unit 103, in addition to the rotation angle θ of the tip end of the catheter which has been calculated.

<Catheter Tip-End Rotation Angle Correction Unit 314>

Figure 23:
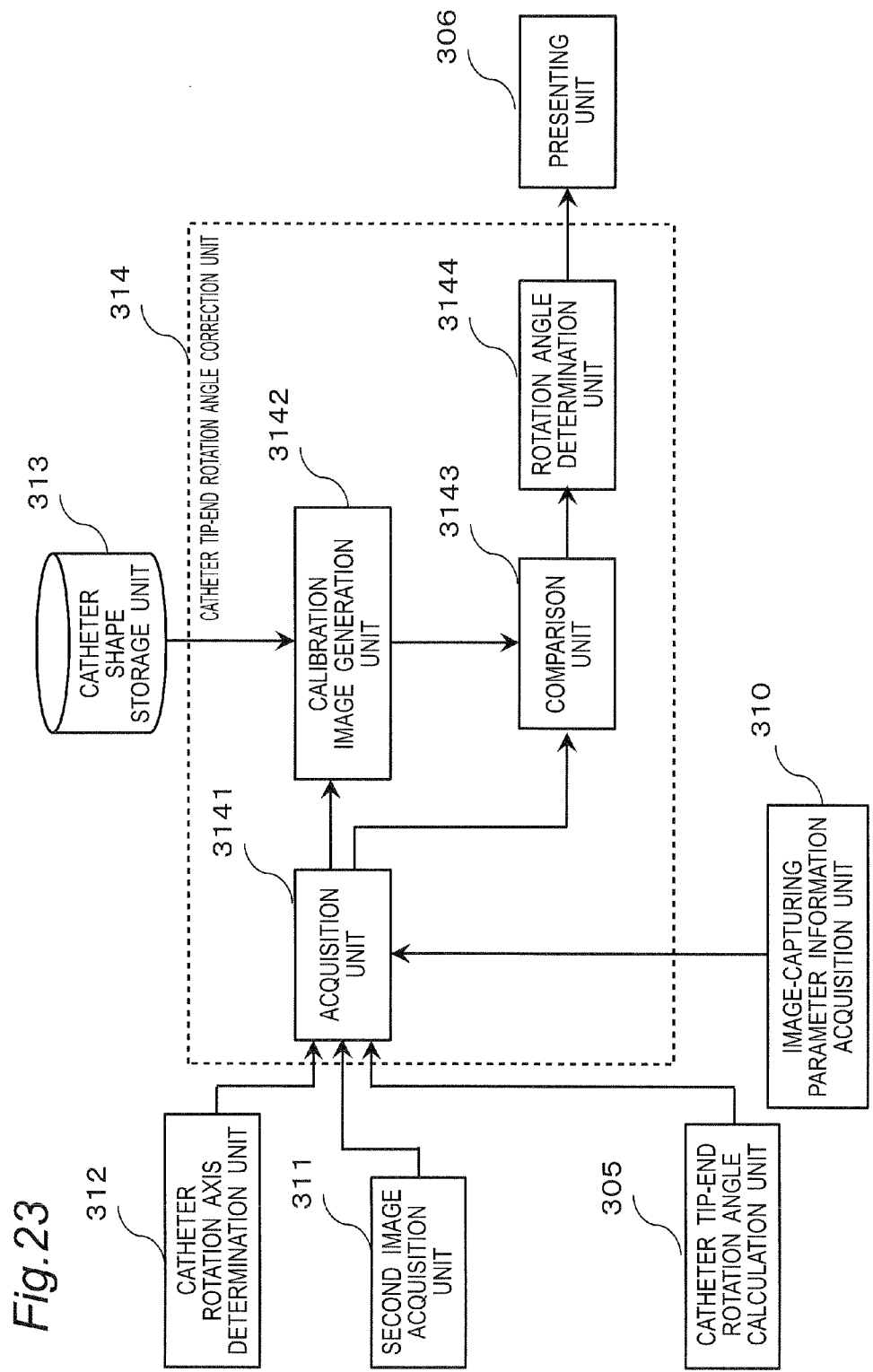
FIG. 23 is a block diagram showing a functional configuration of a catheter tip-end rotation angle correction unit according to the third embodiment.

FIG. 23 shows a functional configuration of the catheter tip-end rotation angle correction unit 314. As shown in FIG. 23, the catheter tip-end rotation angle correction unit 314 includes an acquisition unit 3141, a calibration image generation unit 3142, a comparison unit 3143, and a rotation angle determination unit 3144. In the following, each structural element of the catheter tip-end rotation angle correction unit 314 will be described.

<Acquisition Unit 3141>

The acquisition unit 3141 acquires a first X-ray image among a plurality of X-ray images from the second image acquisition unit 311, the rotation angle θ and the second rotation angle $θ_2$ of the catheter 10 from the catheter tip-end rotation angle calculation unit 305, a catheter rotation axis from the catheter rotation axis determination unit 312, and image-capturing parameter information at the time of capturing the first X-ray image from the image-capturing parameter information acquisition unit 310, respectively.

<Calibration Image Generation Unit 3142>

The calibration image generation unit 3142 acquires, from the catheter shape storage unit 313, a plurality of shapes of the tip end of the catheter 10 for each rotation angle from the rotation angle θ of the tip end of the catheter 10 to the second rotation angle $θ_2$ acquired by the acquisition unit 3141, and generates a plurality of calibration images each associating the shape of the tip end of the catheter 10 and a rotation angle θa acquired.

Figure 24:
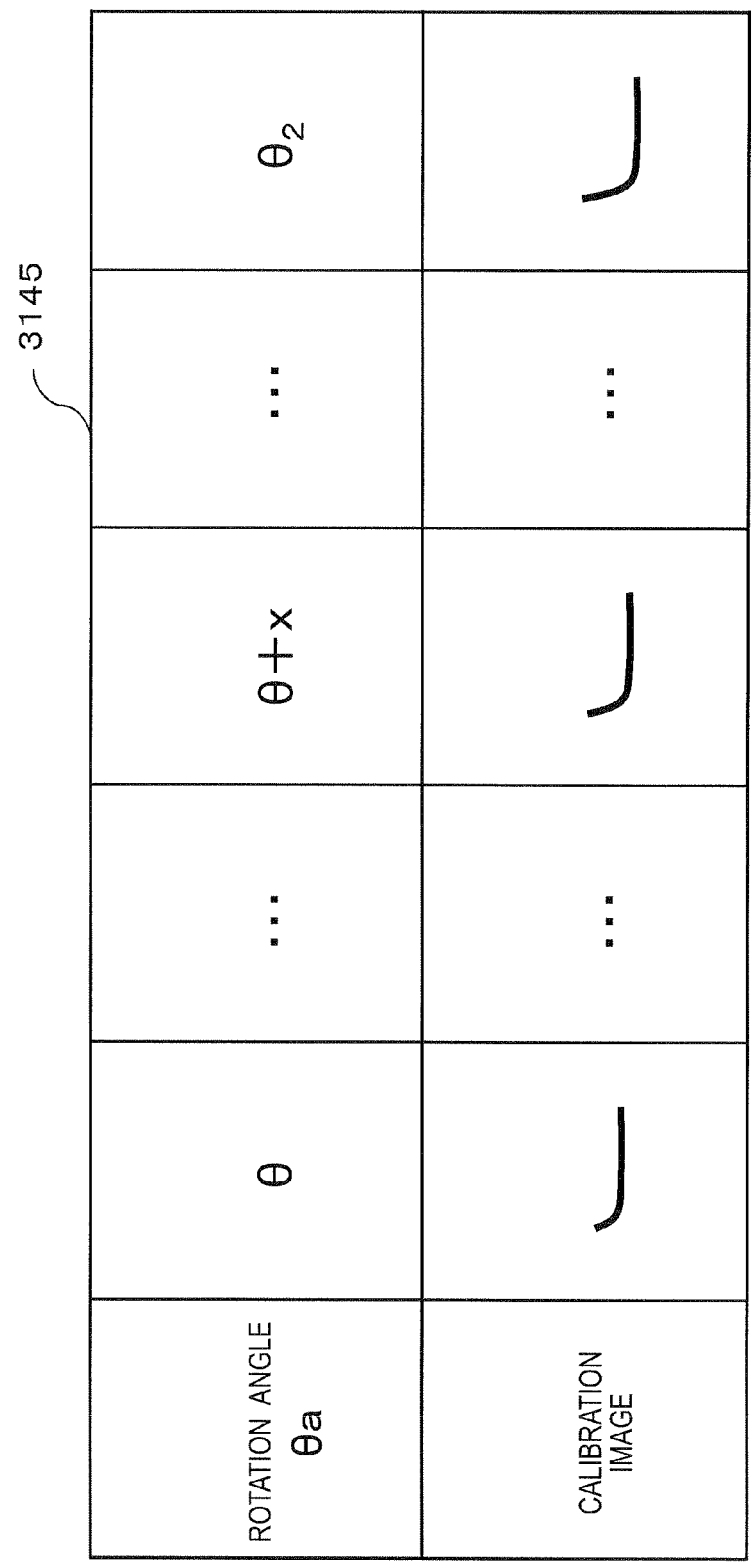
FIG. 24 is a view showing table showing a relationship between calibration images and rotation angles of a tip end of the catheter according to the third embodiment.

FIG. 24 shows example of the calibration images. The concrete method of the calibration image generation unit 3142 to generate a calibration image will be described.

First, the calibration image generation unit 3142 causes the rotation axis of a three-dimensional shape model acquired by the catheter shape storage unit 313 to coincide with the rotation axis acquired by the catheter rotation axis determination unit 312.

Then, by using one of the pieces of image-capturing parameter information for two directions acquired by the image-capturing parameter information acquisition unit 310, the calibration image generation unit 3142 generates, at predetermined angle intervals (for example, every one degree), images whose rotation angles θ of the tip end of the catheter 10 correspond to angles from the rotation angle θ to the second rotation angle $θ_2$ calculated by the catheter tip-end rotation angle calculation unit 305, among calibration images which are assumed in a case of image-capturing the three-dimensional shape model with the coincided rotation axis using the image-capturing parameter information. Here, the reason the generation range is from θ to $θ_2$ is that, in a case where a part or all of the twist is released and there is a partial twist, the actual rotation angle is present between the rotation angle θ of the tip end of the catheter 10 and the second rotation angle $θ_2$ that are calculated while assuming that there is a uniform twist.

<Comparison Unit 3143>

The comparison unit 3143 compares the first X-ray image acquired by the acquisition unit 3141 and a plurality of calibration images generated by the calibration image generation unit 3142, and determines the calibration image with the highest degree of similarity to the first X-ray image.

Figure 25:
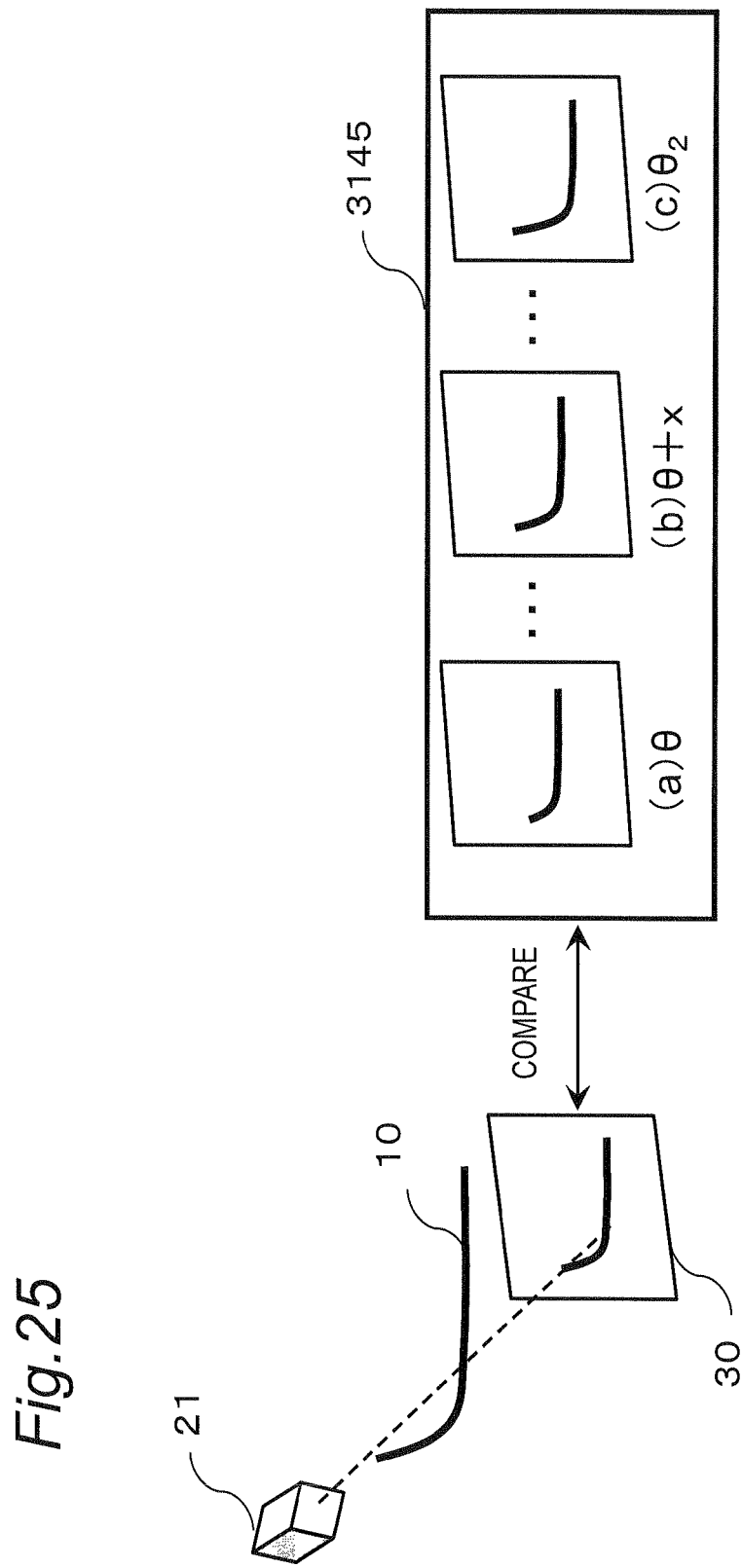
FIG. 25 is an explanatory view showing comparison of an X-ray image and calibration images according to the third embodiment.

FIG. 25 schematically shows comparison of an X-ray image and calibration images.

The concrete method of comparison by the comparison unit 3143 will be described. The comparison unit 3143 extracts a feature point such as an edge or a corner from the first X-ray image, and calculates a feature quantity from the peripheral region. Furthermore, the comparison unit 3143 similarly performs calculation of a feature quantity for a plurality of calibration images. The comparison unit 3143 compares the feature quantity of the first X-ray image and the feature quantity of each calibration image, and determines a calibration image whose degree of matching of feature quantity is the highest, as the calibration image with the highest degree of similarity to the first X-ray image.

Additionally, the method of the comparison unit 3143 to calculate the degree of similarity of images may be any method of calculating the degree of similarity of monochrome images.

<Rotation Angle Determination Unit 3144>

The rotation angle determination unit 3144 determines a rotation angle θa corresponding to the calibration image determined by the comparison unit 3143, as the rotation angle θ of the tip end of the catheter 10.

<Presenting Unit 306>

Figure 11B:
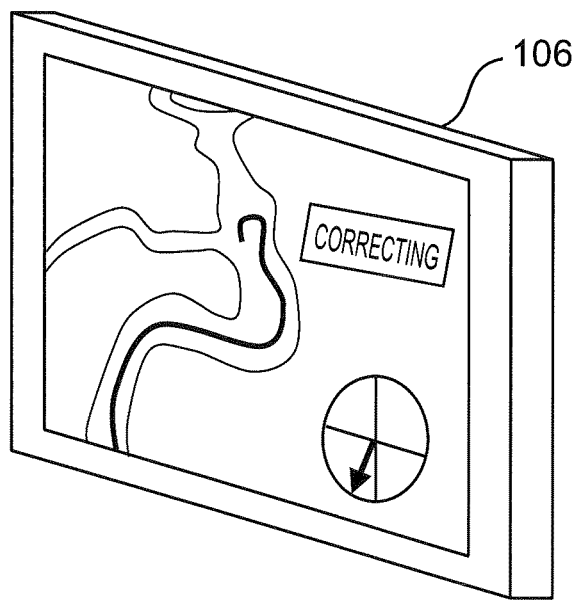
FIG. 11B is a view showing a state, according to the first embodiment, where an example of the rotation angle of the tip of the catheter to be presented to a user is displayed on a display together with a display of "correcting"

The presenting unit 306 presents the rotation angle θ of the tip end of the catheter 10 determined by the rotation angle determination unit 3144 to the user. At this time, as shown in FIG. 11B, "correcting" may be displayed to show the user, such as a doctor or a technician, that calibration (correction) is being performed.

<Operation>

Figure 27:
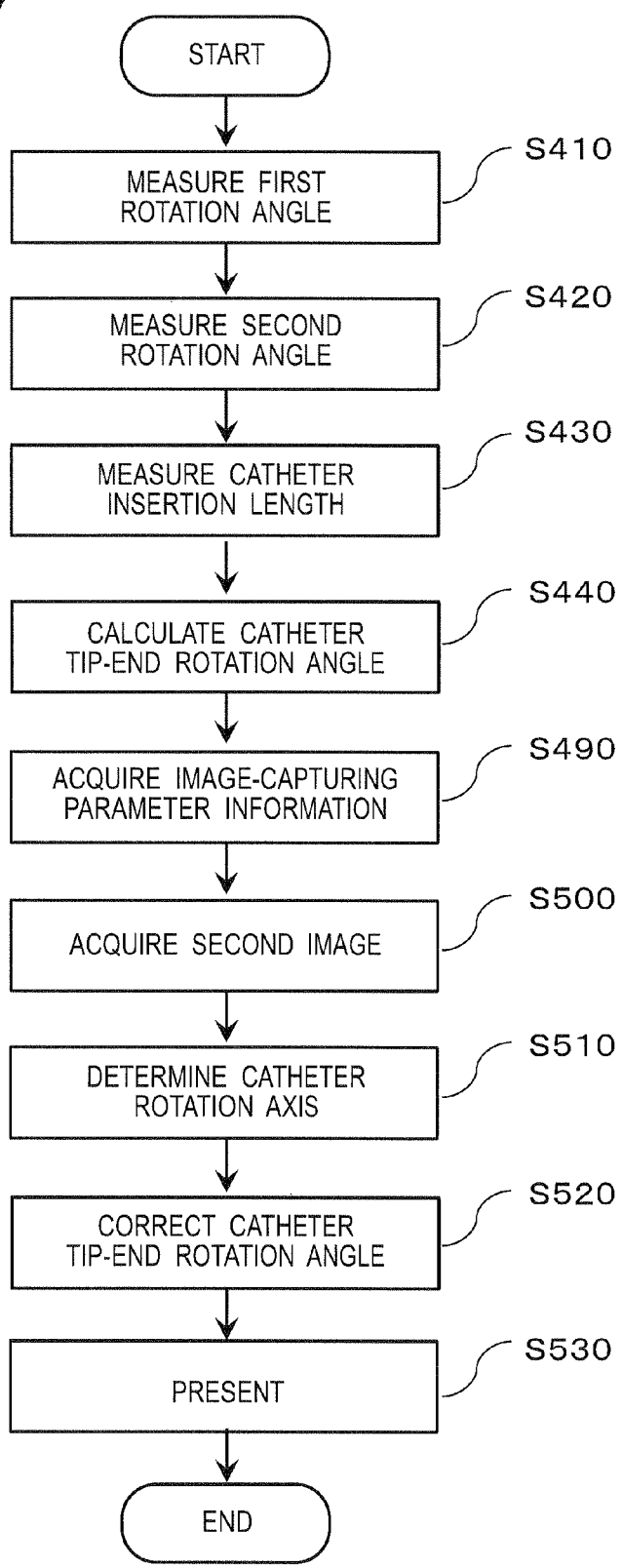
FIG. 27 is a flowchart showing an example of an operation of the catheter tip-end rotation angle measurement apparatus according to the third embodiment.

Next, the operation of each structural element of the catheter tip-end rotation angle measurement apparatus 300 configured in the manner described above will be concretely described. FIG. 27 shows a flow of the operation of the catheter tip-end rotation angle measurement apparatus 300 according to the third embodiment. Additionally, in FIG. 27, steps the same as those in FIG. 13 are denoted by the same reference numerals, and description thereof will be omitted as appropriately.

<Step S490>

The image-capturing parameter information acquisition unit 310 acquires the image-capturing parameter information, which is information about the image-capturing conditions and orientation of each X-ray image capturing device 20 at the time of capturing. Also, the image-capturing parameter information acquisition unit 310 outputs the image-capturing parameter information which has been acquired, to the catheter tip-end rotation angle correction unit 314.

<Step S500>

The second image acquisition unit 311 image-captures a region including the end tip portion 15 of the catheter 10 inserted into a body lumen, and acquires a plurality of X-ray images 30 captured by the plurality of X-ray image capturing devices 20 provided at different positions. Also, the second image acquisition unit 311 outputs the plurality of X-ray images 30 which have been acquired, to the catheter rotation axis determination unit 312.

<Step S510>

The catheter rotation axis determination unit 312 extracts a part of the catheter 10 which is a straight line in each X-ray image from the plurality of X-ray images acquired by the second image acquisition unit 311, reconstructs the three-dimensional shape of the catheter 10 by using the parts of the catheter 10 which are straight lines which have been extracted and the image-capturing parameter information at the time of capturing of each X-ray image acquired by the image-capturing parameter information acquisition unit 310, and determines the rotation axis with respect to the insertion direction of the catheter 10 based on the three-dimensional shape of the catheter 10 which has been reconstructed. Also, the catheter rotation axis determination unit 312 externally outputs the rotation axis which has been determined and the X-ray image acquired by the second image acquisition unit 311. Furthermore, the catheter rotation axis determination unit 312 outputs the rotation axis which has been determined and the X-ray image, to the catheter tip-end rotation angle correction unit 314.

<Step S520>

The catheter tip-end rotation angle correction unit 314 corrects the rotation angle of the tip end of the catheter 10. Also, the catheter tip-end rotation angle correction unit 314 outputs the result of correction to the presenting unit 306.

Concrete description of the operation of the catheter tip-end rotation angle correction unit 314 will be given below.

<Step S530>

The presenting unit 306 presents the rotation angle θ of the tip end of the catheter 10 determined by the rotation angle determination unit 3144, to the user.

The operation described above is the operation of the catheter tip-end rotation angle measurement apparatus 300 according to the third embodiment.

Next, the operation of the catheter tip-end rotation angle correction unit 314, which is a characteristic structural element of the catheter tip-end rotation angle measurement apparatus 300, will be described in detail.

Figure 28:
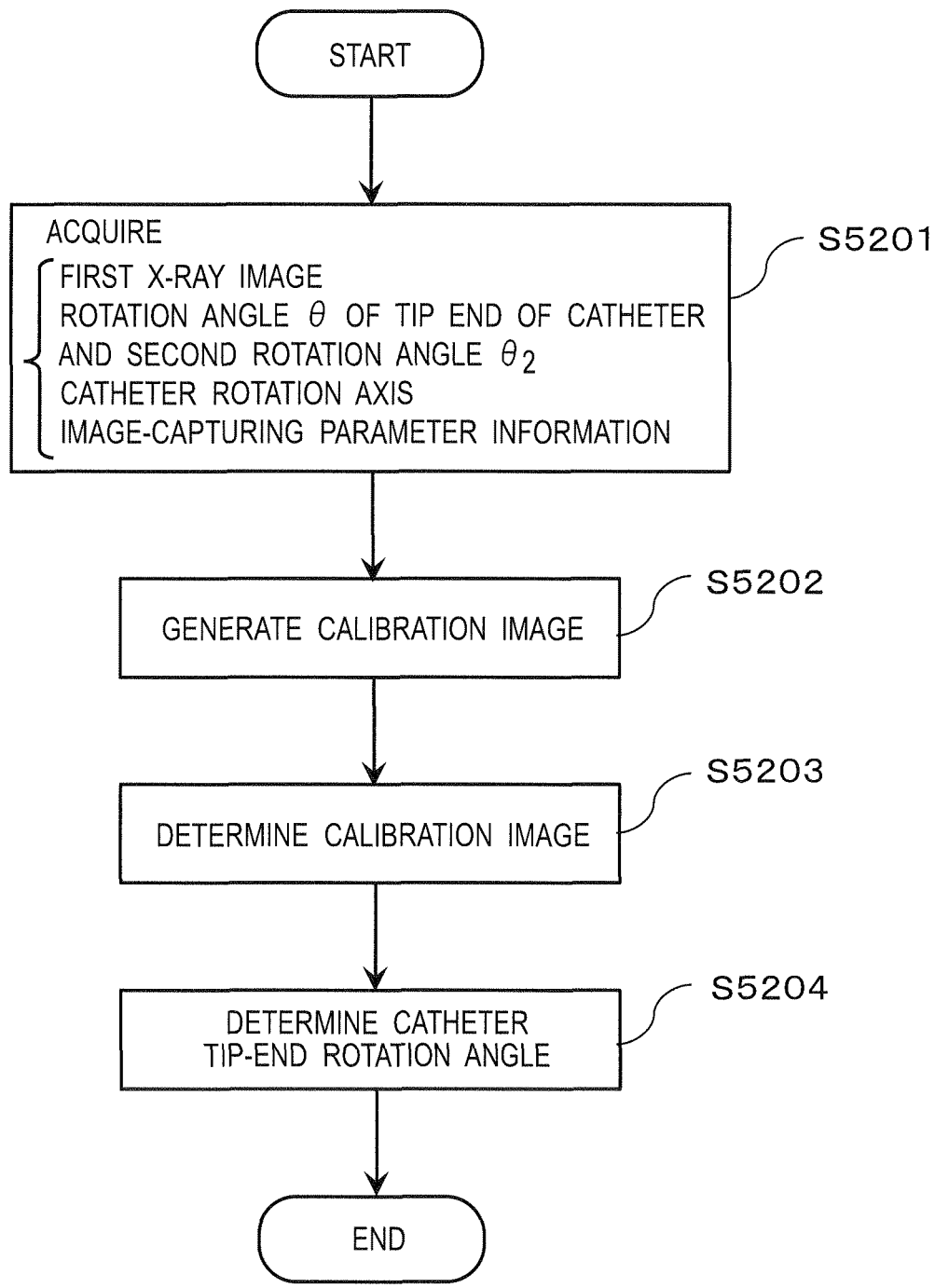
FIG. 28 is a flowchart showing an example of an operation of the catheter tip-end rotation angle correction unit according to the third embodiment.

FIG. 28 shows a flow of the operation of the catheter tip-end rotation angle correction unit 314.

<Step S5201>

The acquisition unit 3141 acquires a first X-ray image among a plurality of X-ray images from the second image acquisition unit 311, the rotation angle θ of the tip end of the catheter 10 and the second rotation angle $\theta_2$ from the catheter tip-end rotation angle calculation unit 305, a catheter rotation axis from the catheter rotation axis determination unit 312, and image-capturing parameter information at the time of capturing the first X-ray image from the image-capturing parameter information acquisition unit 310, respectively. Also, the acquisition unit 3141 outputs each piece of information or the like which has been acquired, to the calibration image generation unit 3142 and the comparison unit 3143.

The timing of acquisition of each piece of information or the like by the acquisition unit 3141 is a predetermined time interval. Additionally, the acquisition unit 3141 may acquire the catheter insertion length L from the catheter insertion length measurement unit 104, and may perform acquisition in a case where there is a change in the catheter insertion length L.

<Step S5202>

The calibration image generation unit 3142 acquires, from the catheter shape storage unit 313, a plurality of shapes of the tip end of the catheter 10 for each rotation angle from the rotation angle θ of the tip end of the catheter 10 to the second rotation angle $\theta_2$ acquired by the acquisition unit 3141, and generates a plurality of calibration images each associating the shape of the tip end of the catheter 10 acquired and a rotation angle θa. Also, the calibration image generation unit 3142 outputs the plurality of calibration images which have been generated, to the comparison unit 3143.

<Step S5203>

The comparison unit 3143 compares the first X-ray image acquired by the acquisition unit 3141 and the plurality of calibration images generated by the calibration image generation unit 3142, and determines the calibration image with the highest degree of similarity to the first X-ray image. Also, the comparison unit 3143 outputs the calibration image which has been determined, to the rotation angle determination unit 3144.

<Step S5204>

The rotation angle determination unit 3144 determines a rotation angle θa corresponding to the calibration image determined by the comparison unit 3143, as the rotation angle θ of the tip end of the catheter 10. Also, the rotation angle determination unit 3144 outputs the rotation angle θ of the tip end of the catheter 10 which has been determined, to the presenting unit 306.

<Effect>

As described above, according to the catheter tip-end rotation angle measurement apparatus 300 of the third embodiment, the rotation angle of the tip end of the catheter 10 may be accurately measured even in a case where a part of the catheter 10 is twisted. Accordingly, a surgeon may grasp the rotation angle θ of the tip end of the catheter 10 even in a case where a part of the catheter 10 is twisted. The surgeon is thereby enabled to easily align, at a branching portion of a blood vessel, the tip end of the catheter with the branching direction of the target blood vessel or the like, and smooth catheter manipulation is enabled. Also, since smooth catheter manipulation may reduce the surgery time, the radiation time of X-rays radiated on a patient may be reduced. Thus, the dose of radiation to the patient by X-ray radiation may be lowered.

First Modification Example

For example, in the case of using at least two catheters 10 with different shapes, such as catheters 10 with a hook-shaped tip end and a straight tip end, calculation of the tip-end rotation angle described above has to be performed for the hook-shaped tip-end catheter 10, but calculation of the tip-end rotation angle described above is not necessary for the straight tip-end catheter 10, and the calculation may be stopped. An example of automatic decision of whether to stop calculation to be performed according to the shape of the tip end corresponding to the tip-end rotation angle is described below as a first modification example. Additionally, the same can be said for a case where guide wires 16 are used instead, or together with, the catheters 10 and where two types of guide wires, i.e. a guide wire 16 whose tip end is straight and a guide wire 16 whose tip end is hook-shaped are used.

Figure 30:
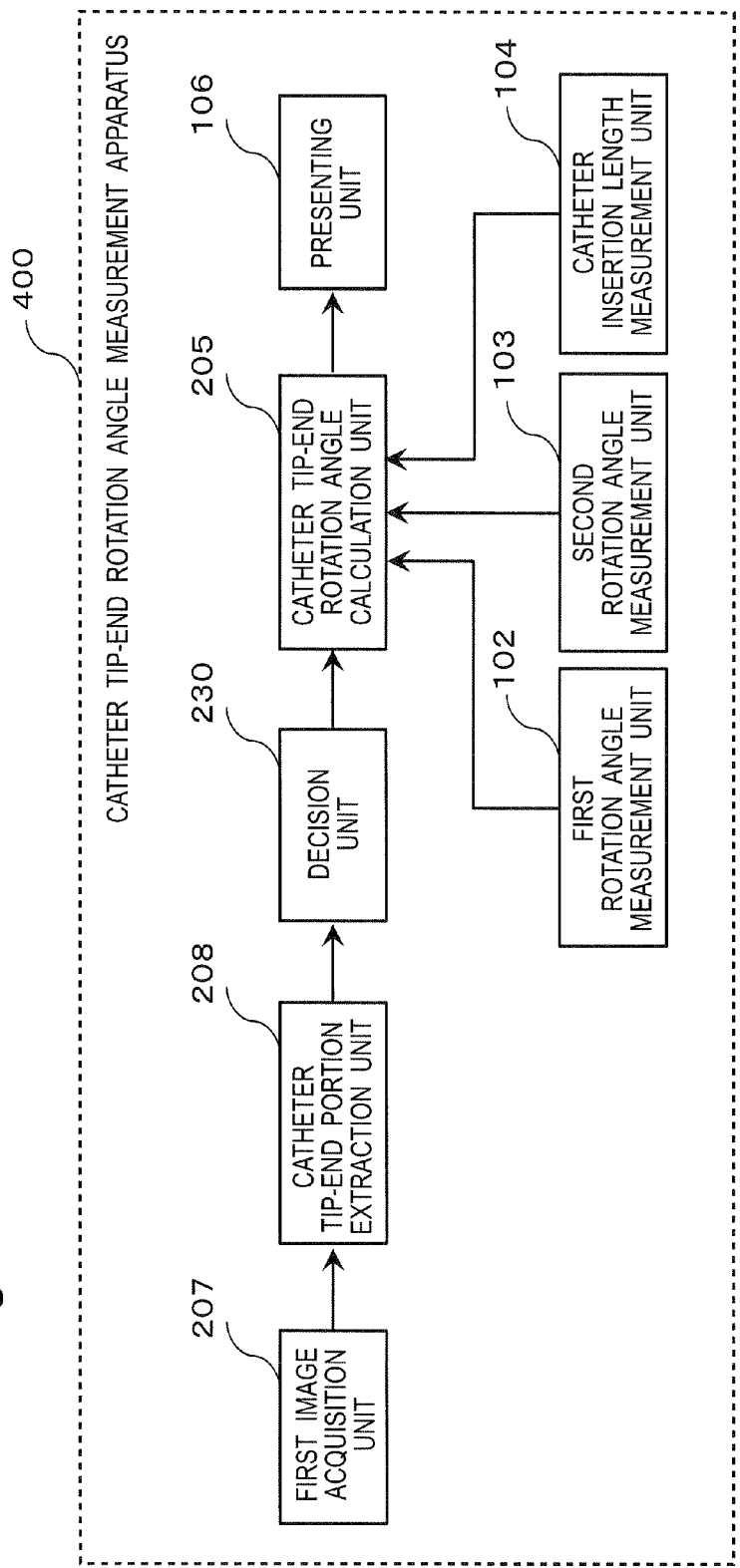
FIG. 30 is a block diagram of a catheter tip-end rotation angle measurement apparatus according to a first modification example for performing automatic decision for stopping calculation of a tip-end rotation angle.

As shown in FIG. 30, a catheter tip-end rotation angle measurement apparatus 400 includes the first rotation angle measurement unit 102, the second rotation angle measurement unit 103, the catheter insertion length measurement unit 104, the catheter tip-end rotation angle calculation unit 205, the presenting unit 106, the first image acquisition unit 207, the catheter tip-end portion extraction unit 208, and a decision unit 230. Moreover, although not shown in FIG. 30, the movement restriction unit 101 is also provided. Other than the first image acquisition unit 207, the catheter tip-end portion extraction unit 208, and the decision unit 230 are same as those in the first embodiment and the like, and thus, detailed description thereof is omitted and only the different elements will be described below.

The first image acquisition unit 207 acquires an X-ray image captured by the X-ray image capturing device 20 for image-capturing a region including a tip end portion of the catheter 10 inserted into a body lumen.

The catheter tip-end portion extraction unit 208 extracts the tip end portion of the catheter 10 from the X-ray image acquired by the first image acquisition unit 207.

The decision unit 230 performs straight line image decision of whether the tip end portion of the catheter 10 extracted by the catheter tip-end portion extraction unit 208 is a straight line image in the X-ray image. Also, in the case where the tip end portion of the catheter 10 is decided to be a straight line image, the decision unit 230 performs density change decision of whether there is a change in density at the tip end portion at a predetermined threshold or more. In the case where a straight line image and no change in density for the tip end portion are decided as a result of decision by the decision unit 230, the decision unit 230 performs decision for stopping calculation of the catheter tip-end rotation angle.

Figure 31A:
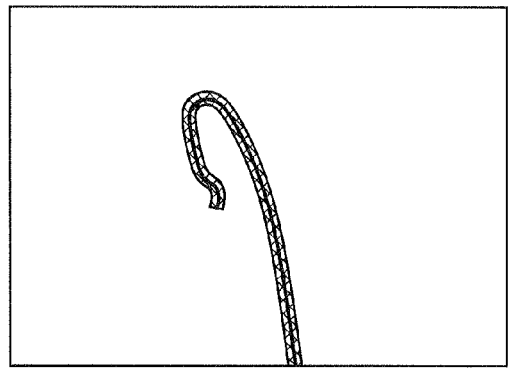
FIG. 31A is a view showing a captured X-ray image example of the state of a tip end of a catheter (or a guide wire)
Figure 31B:
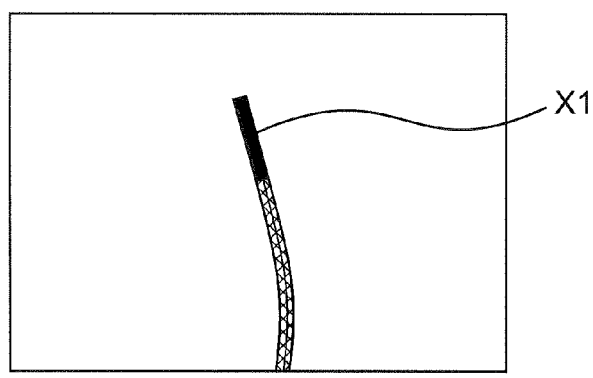
FIG. 31B is a view showing a captured X-ray image example of the state of a tip end of a catheter (or a guide wire)
Figure 31C:
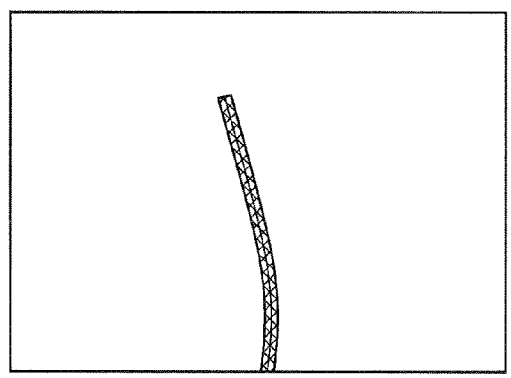
FIG. 31C is a view showing a captured X-ray image example of the state of a tip end of a catheter (or a guide wire)

FIGS. 31A to 31C each shows an example X-ray image captured showing the state of the tip end of the catheter 10 (or the guide wire). FIG. 31A shows a case where a straight line image is not decided at the time of straight line image decision by the decision unit 230 (that is, a case where the shape of the tip end is a hook, for example). FIG. 31B shows a case where a straight line image is decided at the time of straight line image decision by the decision unit 230, and where a change in density is decided at the time of tip-end-portion density change decision by the decision unit 230 (a case where the hook-shaped tip end portion is overlapped and is densely projected). FIG. 31C shows a case where a straight line image is decided at the time of straight line image decision by the decision unit 230, and where no change in density is decided at the time of tip-end-portion density change decision by the decision unit 230 (a case where the shape of the tip end is straight). These images will be described in detail in the description of the flow given below.

Figure 32:
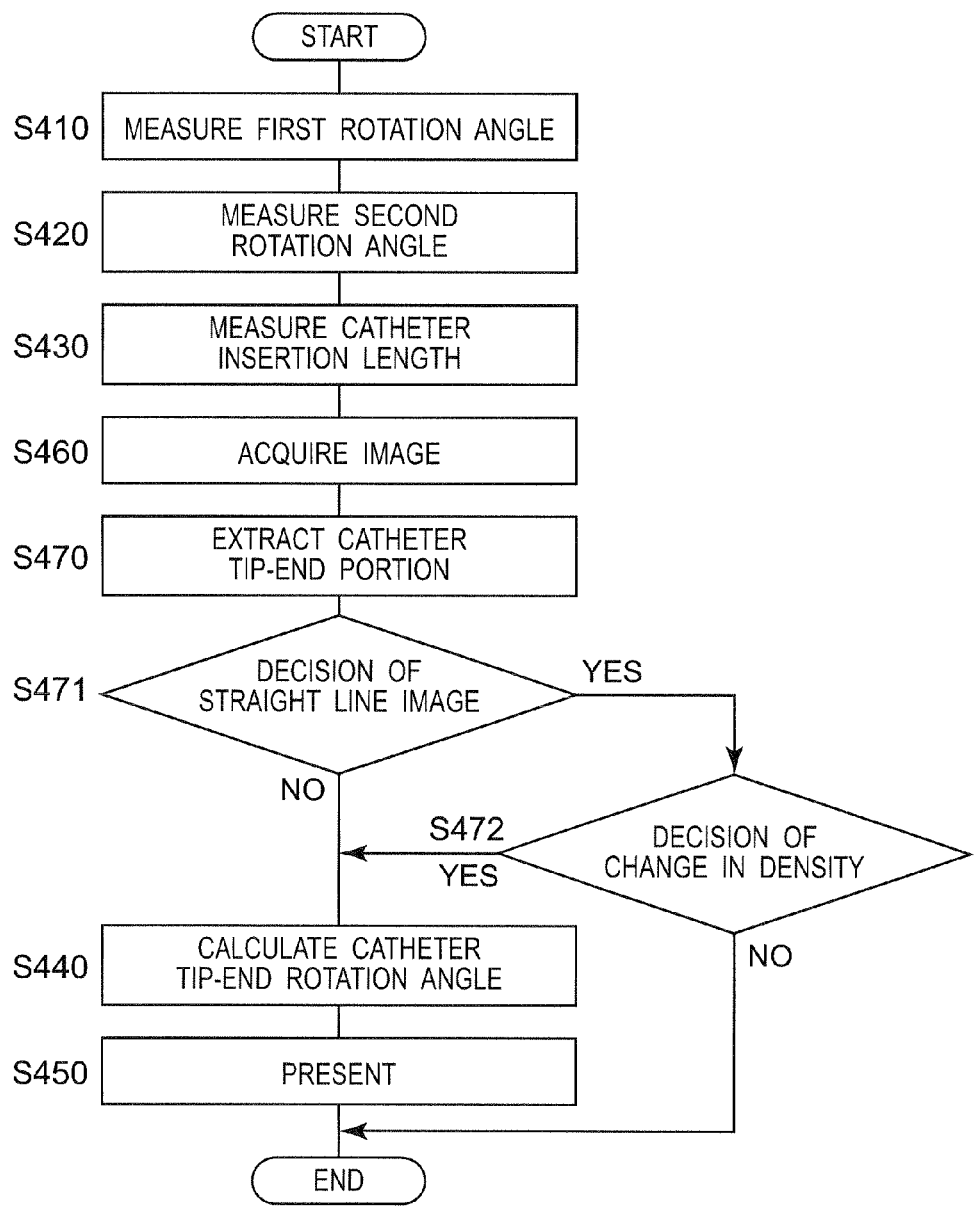
FIG. 32 is a flowchart of an operation of the catheter tip-end rotation angle measurement apparatus according to the first modification example.

The operation of such a catheter tip-end rotation angle measurement apparatus 400 will be shown in FIG. 32. Additionally, steps S410, S420, S430 and S450 in FIG. 32 are the same as those in the preceding embodiments, and thus, description thereof is omitted, and only the different portions will be described below.

As in the second embodiment, the first image acquisition unit 207 acquires an X-ray image 30 captured by the X-ray image capturing device 20 for image-capturing a region including the tip end portion of the catheter 10 inserted into a body lumen (step S460 in FIG. 32).

Then, the catheter tip-end portion extraction unit 208 extracts the tip end portion 15 of the catheter from the X-ray image 30 acquired by the first image acquisition unit 207 (step S470 in FIG. 32). At this time, first, whether the tip end portion of the catheter 10 is a straight line image in the X-ray image 30 or not is decided by the decision unit 230 (step S471 in FIG. 32). If the tip end portion of the catheter 10 is decided by the decision unit 230 to be not a straight line image (see FIG. 31A) (in the case of NO in step S471 in FIG. 32), the shape of the tip end portion of the catheter 10 is a hook and the decision unit 230 decides that calculation of the tip-end rotation angle is necessary (or the decision unit 230 performs no decision), and the catheter tip-end rotation angle calculation unit 205 performs calculation of the catheter tip-end rotation angle (step S440 in FIG. 32). On the other hand, when the tip end portion of the catheter 10 is a straight line image in the X-ray image 30 (in the case of YES in step S471 in FIG. 32), the decision unit 230 performs decision regarding a change in density of whether there is a change in density at the tip end portion that is equal to or greater than a predetermined threshold (step S472 in FIG. 32). The reason that such a process is performed is as below. If the tip end portion of the catheter 10 is a straight line image in the X-ray image 30, two cases, i.e. a case where the tip end portion of the catheter 10 is hook-shaped but is image-captured in an overlapping manner depending on the rotation angle, and a case where the shape of the tip end portion of the catheter 10 is a straight line, are conceivable.

In the case of the former, although a straight line image is seen, when the tip end portion is irradiated with X-rays, the X-rays are attenuated two times at a part of the tip end portion and a dark part is generated (see X1 in FIG. 31B). That is, the tip end is hook-shaped if there is a part with a high attenuation rate and there is a part where the shade is equal to or greater than the threshold. On the other hand, if there is no such shade part, the tip end has a straight line shape (see FIG. 31C). Accordingly, when it is decided by the decision unit 230 that the tip end portion of the catheter 10 is a straight line image, decision of a change in density for deciding whether there is a change in density at a predetermined threshold or more at the tip end portion is further performed by the decision unit 230.

In the case where a straight line image and a change in density at the tip end portion are decided by the decision unit 230 as a result of decision by the decision unit 230 (in the case of YES in step S472 in FIG. 32), the shape of the tip end portion of the catheter 10 is a hook. Accordingly, the decision unit 230 decides that calculation of the tip-end rotation angle is necessary, and the catheter tip-end rotation angle calculation unit 205 performs calculation of the catheter tip-end rotation angle (step S440 in FIG. 32).

On the other hand, in the case where a straight line image is decided by the decision unit 230 but no change in density at the tip end portion is decided as a result of decision by the decision unit 230 (in the case of NO in step S472 in FIG. 32), the shape of the tip end portion of the catheter 10 is straight. Accordingly, the decision unit 230 decides that calculation of the tip-end rotation angle is not necessary, and the catheter tip-end rotation angle calculation unit 205 stops calculation of the catheter tip-end rotation angle (the flow is ended without step S440 in FIG. 32 being performed).

According to such a modification example, unnecessary calculation process may be automatically omitted in a case where the shape of the tip end portion of the catheter 10 is straight and calculation of the tip-end rotation angle is unnecessary.

Second Modification Example

Figure 33:
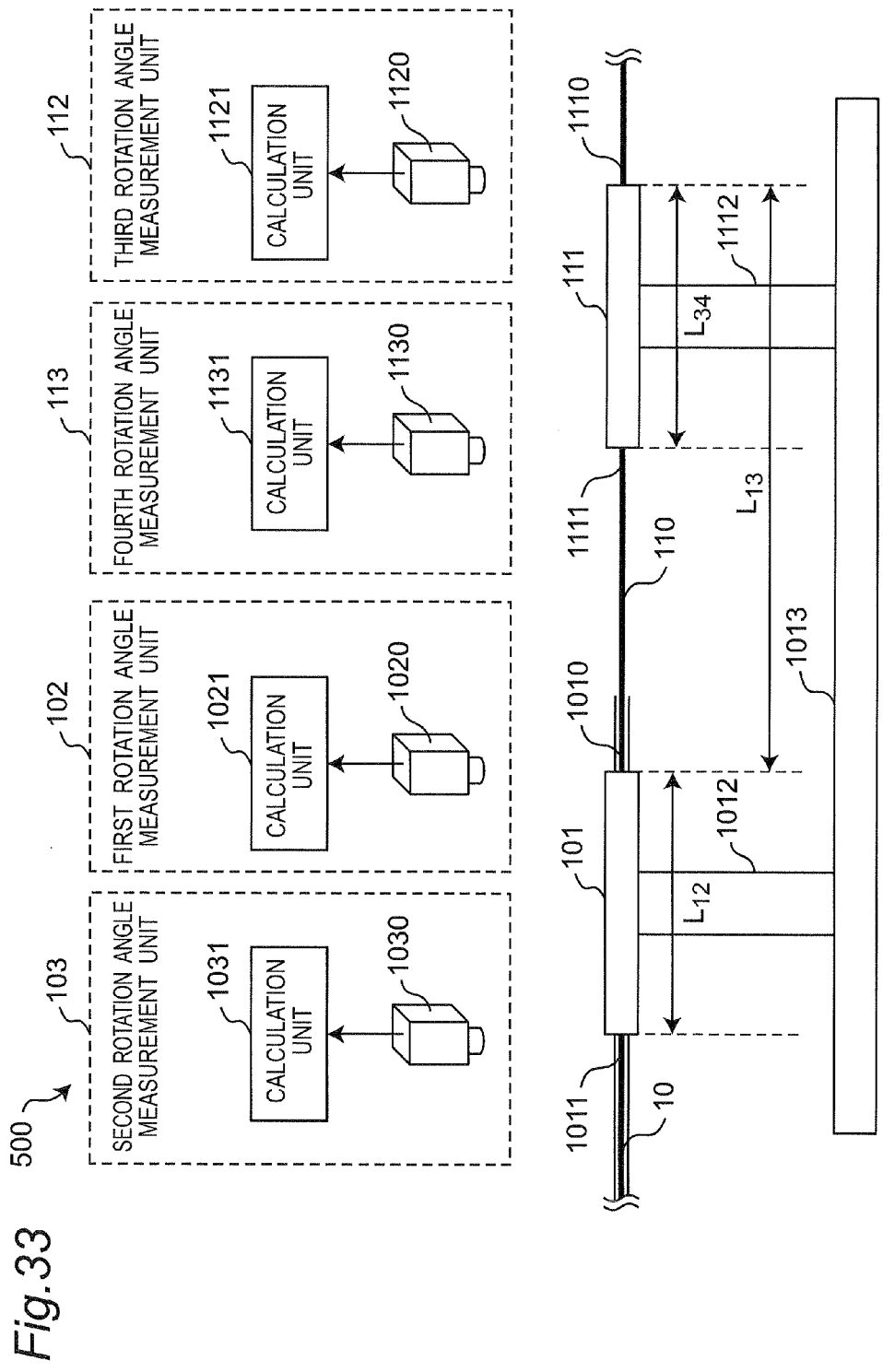
FIG. 33 is a block diagram of a catheter tip-end rotation angle measurement apparatus according to a second modification example.

An example of calculating the tip-end rotation angles of both the guide wire 16 and the catheter 10 will be described below as a second modification example. The catheter tip-end rotation angle measurement apparatus 100 for calculating the tip-end rotation angle of the catheter 10 further includes a device for calculating the tip-end rotation angle of the guide wire 16. That is, as shown in FIG. 33, a catheter tip-end rotation angle measurement apparatus 500 includes the first rotation angle measurement unit 102, the second rotation angle measurement unit 103, a third rotation angle measurement unit 112, a fourth rotation angle measurement unit 113, a guide wire insertion length measurement unit 114, a guide-wire tip-end rotation angle calculation unit 115, and a target switching unit 116. Moreover, the movement restriction unit 111 for a guide wire is also included. In FIG. 33, the reference numeral 10 is a catheter, and the reference numeral 110 is a guide wire. Generally, the guide wire 110 is longer than the catheter 10.

Figure 34:
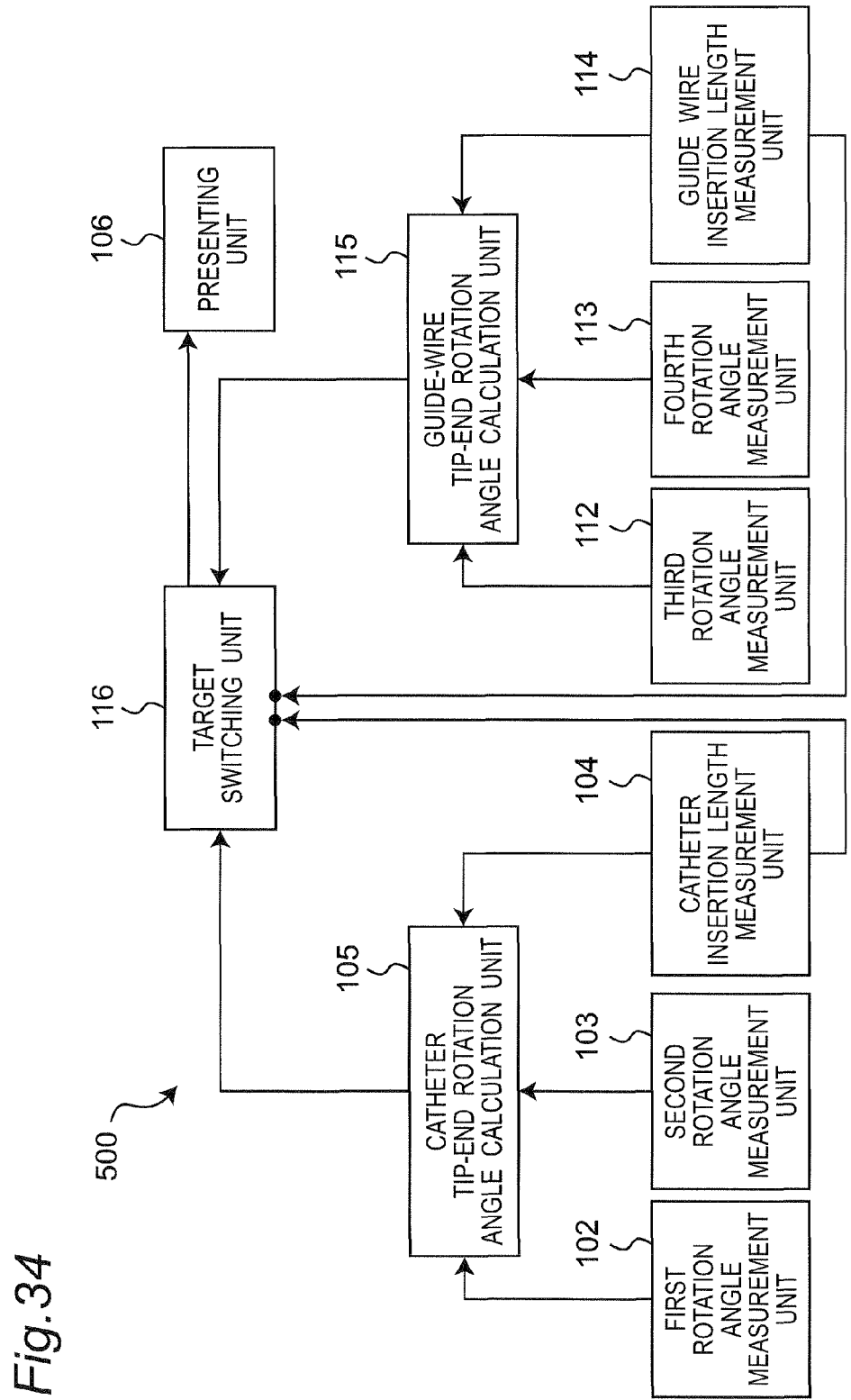
FIG. 34 is a block diagram of the catheter tip-end rotation angle measurement apparatus according to the second modification example.

FIG. 34 shows a block diagram of a catheter tip-end rotation angle measurement apparatus 500. The catheter tip-end rotation angle measurement apparatus 500 separately calculates a catheter tip-end rotation angle and a guide-wire tip-end rotation angle.

Like the first rotation angle measurement unit 102, the third rotation angle measurement unit 112 measures a third rotation angle $\theta_3$ of the guide wire 110, which is the rotation angle of the guide wire 110 at a third hole 1110. Like the first rotation angle measurement unit 102, the third rotation angle measurement unit 112 is configured from an image-capturing unit 1120 (corresponding to the image-capturing unit 1020), and a calculation unit 1121 (corresponding to the calculation unit 1021).

Like the second rotation angle measurement unit 103, the fourth rotation angle measurement unit 113 measures a fourth rotation angle $\theta_4$ of the guide wire 110, which is the rotation angle of the guide wire 110 at a fourth hole 1111. Like the second rotation angle measurement unit 103, the fourth rotation angle measurement unit 113 is configured from an image-capturing unit 1130 (corresponding to the image-capturing unit 1030), and a calculation unit 1131 (corresponding to the calculation unit 1031).

Like the catheter insertion length measurement unit 104, the guide wire insertion length measurement unit 114 measures a guide wire insertion length $L_g$, which is the length from the third hole 1110 or the fourth hole 1111 to the tip end portion of the guide wire 110.

Like the catheter tip-end rotation angle calculation unit 105, the guide-wire tip-end rotation angle calculation unit 115 calculates a rotation angle θ of the tip end of the guide wire by using an angle difference $(\theta_3-\theta_4)$ between the third rotation angle $\theta_3$ measured by the third rotation angle measurement unit 112 and the fourth rotation angle $\theta_4$ measured by the fourth rotation angle measurement unit 113, the guide wire insertion length $L_g$ measured by the guide wire insertion length measurement unit 114, and a distance $L_{34}$ between the third hole 1110 and the fourth hole 1111.

Like the movement restriction unit 101, the movement restriction unit 111 for a guide wire has a tube shape which is penetrated from the third hole 1110 (corresponding to the first hole 1010) to the fourth hole 1111 (corresponding to the second hole 1011), and movement of the guide wire 110 is restricted to the insertion direction by the guide wire 110 passing through from the third hole 1110 to the fourth hole 1111.

The target switching unit 116 performs a target switching process at a timing where one of the catheter insertion length (L or $L_c$) and the guide wire insertion length ($L_g$) changes. Specifically, in the case where $L_c>L_g-L_{13}$ (where $L_{13}$ is the distance between the movement restriction units (101, 111) of the catheter 10 and the guide wire 110 (the distance between the first hole 1010 and the third hole 1110). This distance is set in advance) is true, the catheter tip-end rotation angle is selected, and in the case where $L_c \leq L_g-L_{13}$, the guide wire tip-end rotation angle is selected, and switching regarding transmission information (the target to be presented and its tip-end rotation angle) to the presenting unit 106 is performed.

Figure 35:
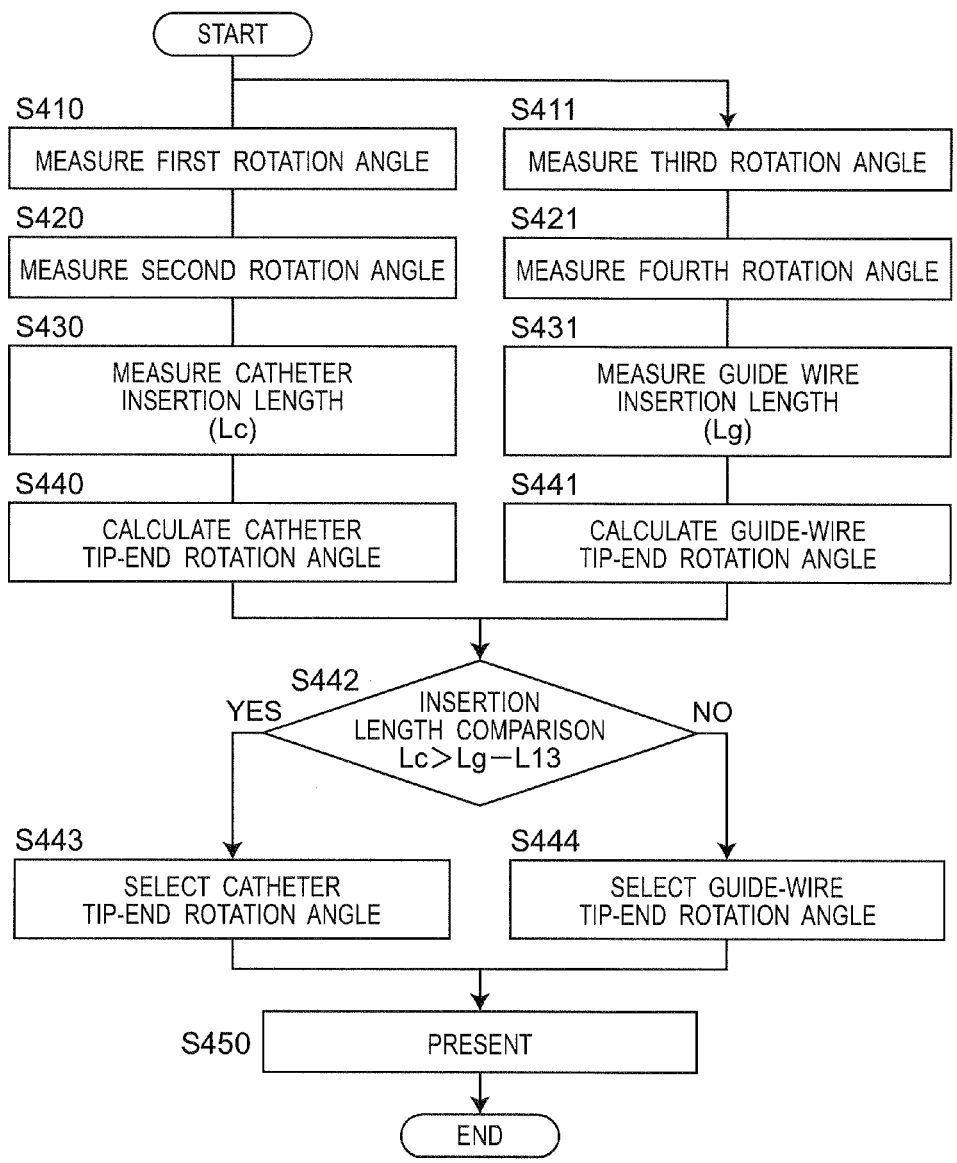
FIG. 35 is a flowchart of an operation of the catheter tip-end rotation angle measurement apparatus according to the second modification example.
Figure 36:
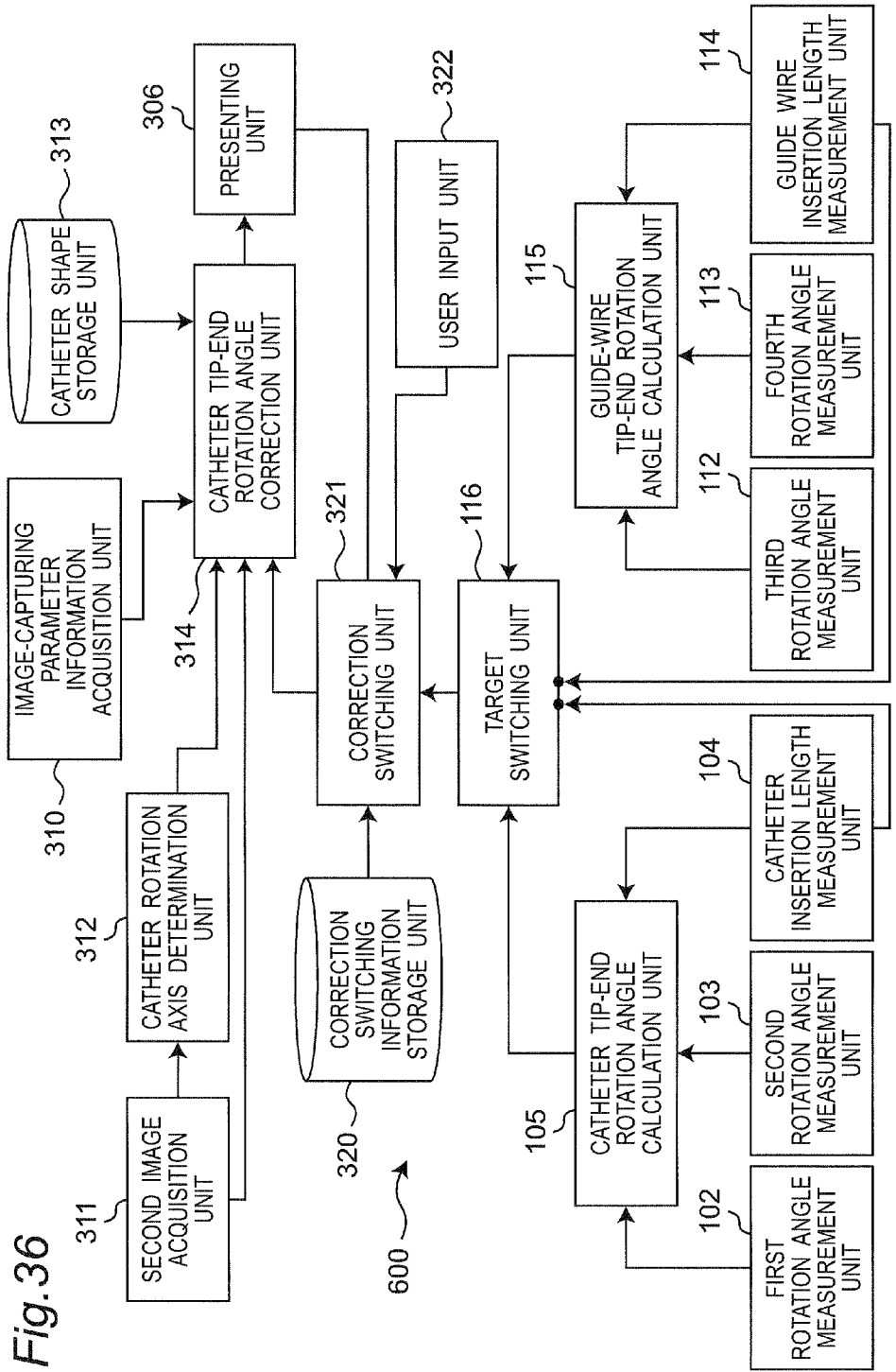
FIG. 36 is a block diagram of a catheter tip-end rotation angle measurement apparatus according to a third modification example.

FIG. 35 shows a flow chart of the operation of the catheter tip-end rotation angle measurement apparatus 500.

First, in step S410, the first rotation angle measurement unit 102 measures the first rotation angle $\theta_1$, which is the rotation angle of the catheter 10 at the first hole 1010.

Then, in step S420, the second rotation angle measurement unit 103 measures the second rotation angle $\theta_2$, which is the rotation angle of the catheter 10 at the second hole 1011.

Next, in step S430, the catheter insertion length measurement unit 104 measures the catheter insertion length, which is the length from the first hole 1010 to the tip end portion 15 of the catheter 10.

Next, in step S440, the catheter tip-end rotation angle calculation unit 105 calculates a rotation angle $\theta_c$ of the tip end of the catheter by using the angle difference $(\theta_1-\theta_2)$ between the first rotation angle $\theta_1$ measured by the first rotation angle measurement unit 102 and the second rotation angle $\theta_2$ measured by the second rotation angle measurement unit 103, the catheter insertion length $L_g$ measured by the catheter insertion length measurement unit 104, and the distance $L_{12}$ between the first hole 1010 and the second hole 1011.

Steps S411 to S441 are performed simultaneously or separately from these steps S410 to S440.

That is, in step S411, the third rotation angle measurement unit 112 measures the third rotation angle $\theta_3$, which is the rotation angle of the guide wire 110 at the third hole 1110.

Then, in step S421, the fourth rotation angle measurement unit 113 measures the fourth rotation angle $\theta_4$, which is the rotation angle of the guide wire 110 at the fourth hole 1111.

Next, in step S431, the guide wire insertion length measurement unit 114 measures the guide wire insertion length $L_g$ which is the length from the third hole 1110 to the tip end portion of the guide wire 110.

Next, in step S441, the guide-wire tip-end rotation angle calculation unit 115 calculates a rotation angle 08 of the tip end of the guide wire 110 by using an angle difference $(\theta_3-\theta_4)$ between the third rotation angle $\theta_3$ measured by the third rotation angle measurement unit 112 and the fourth rotation angle $\theta_4$ measured by the fourth rotation angle measurement unit 113, the guide wire insertion length $L_g$ measured by the guide wire insertion length measurement unit 114, and the distance $L_{34}$ between the third hole 1110 and the fourth hole 1111.

Next, in step S442, the target switching unit 116 acquires the catheter insertion length $L_c$ measured in step S430 from the catheter insertion length measurement unit 104, and also, acquires the guide wire insertion length $L_g$ measured in step S431 from the guide wire insertion length measurement unit 114. Furthermore, the target switching unit 116 acquires the rotation angle $\theta_c$ of the tip end of the catheter 10 calculated in step S440 from the catheter tip-end rotation angle calculation unit 105, and also, acquires the rotation angle $\theta_g$ of the tip end of the guide wire 110 calculated in step S441 from the guide-wire tip-end rotation angle calculation unit 115. Then, the target switching unit 116 decides whether $L_c>L_g-L_{13}$ is established or not.

In the case where $L_c>L_g-L_{13}$ is established (in the case of YES in step S441), the catheter tip-end rotation angle is selected, and the process proceeds to step S450.

In the case where $L_c>L_g-L_{13}$ is not established (in the case of NO in step S441), the guide wire tip-end rotation angle is selected, and the process proceeds to step S450.

Then, in step S450, the presenting unit 106 acquires the tip-end rotation angle selected in step S443 or S444 from the target switching unit 116, and presents the tip-end rotation angle which has been acquired, to the user.

According to this second modification example, also in a case where both the catheter 10 and the guide wire 110 are being used instead of only the catheter 10, the tip-end rotation angle of the catheter 10 and the tip-end rotation angle of the guide wire 110 may be separately measured with high accuracy. Thus, for example, since, until the portion to be diagnosed or treated is neared, only the guide wire 110 is used, the tip-end rotation angle of the guide wire 110 may be measured by the catheter tip-end rotation angle measurement apparatus with higher accuracy, and since, when the portion to be diagnosed or treated is neared, the insertion of the guide wire 110 is stopped and the catheter 10 is inserted instead in alignment with the guide wire 110, the tip-end rotation angle of the catheter 10 may be measured by the catheter tip-end rotation angle measurement apparatus with higher accuracy.

Third Modification Example

An example where switching between the tip-end rotation angle calculation according to the first embodiment and the tip-end rotation angle calculation according to the third embodiment that takes calibration into account is enabled will be described below as a third modification example.

A catheter tip-end rotation angle measurement apparatus 600 according to the third modification example incorporates a correction switching information storage unit 320 as a database and a correction switching unit 321 into a device combining the catheter tip-end rotation angle measurement apparatus 500 according to the second modification example and the catheter tip-end rotation angle measurement apparatus 300 according to the third embodiment in FIG. 20, for example.

The correction switching information storage unit 320 stores information necessary for correction switching (correction switching information). For example, the correction switching information storage unit 320 stores information necessary for correction switching, such as type information of whether it is a catheter or a guide wire, a predetermined threshold for decision of an insertion length difference, an insertion length to a lesion area or a portion to be diagnosed or a portion to be treated (for example, the brain or the heart), and the like.

The correction switching unit 321 switches between correction and no correction based on the correction switching information stored in the correction switching information storage unit 320 and the information from the target switching unit 116, and outputs the result to the catheter tip-end rotation angle correction unit 314 and the presenting unit 306. That is, for example, the correction switching unit 321 acquires the value of the tip-end rotation angle, the type (catheter or guide wire) and the corresponding insertion length from the target switching unit 116, acquires the correction switching information from the correction switching information storage unit 320, and performs correction switching based on these pieces of information. For example, in the case where the type regarding the tip-end rotation angle is the guide wire and the difference between the insertion lengths is less than a predetermined threshold, the correction switching unit 321 outputs the value of the tip-end rotation angle and the type to the presenting unit 306 without performing tip-end rotation angle correction. In other cases, the catheter tip-end rotation angle correction process is performed by the catheter tip-end rotation angle correction unit 314.

According to such a configuration, if, for example, the correction switching unit 321 decides that the catheter 10 is being used and the tip-end rotation angle of the catheter 10 is to be calculated, that correction is to be performed is output to the catheter tip-end rotation angle correction unit 314 and the presenting unit 306 so that calculation of the tip-end rotation angle that takes calibration into account will be performed.

As another example, in the case where the tip-end rotation angle of the guide wire 110 is to be calculated, if the correction switching unit 321 decides that the difference of the insertion lengths reaches or exceeds a predetermined threshold, output to the catheter tip-end rotation angle correction unit 314 and the presenting unit 306 is performed such that calculation of the tip-end rotation angle that takes calibration (correction) into account is performed, and if the correction switching unit 321 decides that the predetermined threshold is not reached, output thereto is performed such that calculation of the tip-end rotation angle without calibration (correction) is performed.

Alternatively, as still another example, the insertion length to the brain or to the heart is stored in advance in the correction switching information storage unit 320, and when the correction switching unit 321 estimates that the catheter reaches a place of a complicated blood vessel system such as the brain or the heart by deciding that the insertion length is reached, output to the catheter tip-end rotation angle correction unit 314 and the presenting unit 306 is performed such that calculation of the tip-end rotation angle that takes calibration (correction) into account is performed.

The insertion length to a lesion area is stored in advance in the correction switching information storage unit 320, and when the correction switching unit 321 estimates that the lesion area is reached by deciding that the insertion length is reached, output to the catheter tip-end rotation angle correction unit 314 and the presenting unit 306 is performed such that calculation of the tip-end rotation angle that takes calibration (correction) into account is performed.

According to this third modification example, by performing the correction process only when necessary, without performing the correction at all times, a highly accurate tip-end rotation angle measurement operation may be performed effectively and swiftly.

Additionally, in the case of switching the correction based on an input from a user who uses the catheter tip-end rotation angle measurement apparatus, such as a technician or a doctor, the correction operation may be switched at an arbitrary timing by inputting correction switching information from a user input unit 322 to the correction switching unit 321.

Though the present disclosure has been described above based on the above first to third embodiments, the present disclosure should not be limited to the above-described first to third embodiments.

By properly combining the arbitrary embodiment (s) or modification(s) of the aforementioned various embodiments and modifications, the effects possessed by the embodiment (s) or modification(s) can be produced.

The catheter tip-end rotation angle measurement apparatus, the catheter tip-end rotation angle measurement method, and the catheter tip-end rotation angle measurement program according to the present invention include a function of measuring the rotation angle of a tip end of a catheter, and are effective for catheter contrast study and treatment. Moreover, usage to educate trainees on the catheter operation is also possible.

Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure as defined by the appended claims unless they depart therefrom.

What is claimed is:

1. A catheter tip-end rotation angle calculation apparatus comprising:
  a movement restriction unit, of a tube shape, that is configured to be penetrated from a first hole to a second hole, and restrict movement of a catheter to a catheter insertion direction by causing the catheter to pass through from the first hole to the second hole;

a first rotation angle measurement unit that measures a first rotation angle that is a rotation angle of the catheter at the first hole;

a second rotation angle measurement unit that measures a second rotation angle that is a rotation angle of the catheter at the second hole;

a catheter insertion length measurement unit that measures a catheter insertion length that is a length from the first hole or the second hole to a tip end portion of the catheter; and a catheter tip-end rotation angle calculation unit that calculates that is a rotation angle of a tip end of the catheter by $\theta=\theta_1-(\theta_1-\theta_2)\cdot L/L_{12}$, where the first rotation angle is $\theta_1$, the second rotation angle is $\theta_2$, the catheter insertion length is L, and a distance between the first hole and the second hole is $L_{12}$.

2. The catheter tip-end rotation angle calculation apparatus according to claim 1, wherein the movement restriction unit is a first movement restriction unit; and the catheter tip-end rotation angle calculation apparatus further comprises:

a second movement restriction unit, of a tube shape, that is configured to be penetrated from a third hole to a fourth hole, and restrict movement of a guide wire to a guide wire insertion direction by causing the guide wire to pass through from the third hole to the fourth hole;

a third rotation angle measurement unit that measures a third rotation angle that is a rotation angle of the guide wire at the third hole;

a fourth rotation angle measurement unit that measures a fourth rotation angle that is a rotation angle of the guide wire at the fourth hole;

a guide wire insertion length measurement unit that measures a guide wire insertion length that is a length from the third hole or the fourth hole to a tip end portion of the guide wire; and a guide wire tip-end rotation angle calculation unit that calculates $\theta_g$ that is a rotation angle of a tip end of the guide wire by $\theta_g=\theta_3-(\theta_3-\theta_4)\cdot L_g/L_{34}$, where the third rotation angle is $\theta_3$, the fourth rotation angle is $\theta_4$, the guide wire insertion length is $L_g$, and a distance between the third hole and the fourth hole is $L_{34}$.

3. The catheter tip-end rotation angle calculation apparatus according to claim 1, comprising:

an X-ray image capturing device that image-captures a region including the tip end portion of the catheter when the catheter is inserted into a body lumen;

a catheter tip-end portion extraction unit that extracts the region including the tip end portion of the catheter from an image captured by the X-ray image capturing device; and a decision unit that decides, based on information extracted by the catheter tip-end portion extraction unit, whether to calculate the rotation angle of the tip end of the catheter by the catheter tip-end rotation angle calculation unit or not.

4. The catheter tip-end rotation angle calculation apparatus according to claim 3, wherein the decision unit performs straight line image decision of deciding, based on an image of the tip end portion of the catheter extracted from the image captured by the X-ray image capturing device, whether the tip end portion of the catheter is a straight line image or not, and in a case where the tip end portion of the catheter is decided to be a straight line image, the decision unit performs decision regarding a change in density of whether there is a change in density at the tip end portion of the catheter that is at a predetermined threshold or more, and if there is a change in density at the predetermined threshold or more, the tip end portion of the catheter is decided to be unstraight and tip-end rotation angle calculation is decided to be necessary, and if there is no change in density that is at the predetermined threshold or more, the tip end portion of the catheter is decided to be straight and tip-end rotation angle calculation is decided to be unnecessary.

5. The catheter tip-end rotation angle calculation apparatus according to claim 1, further comprising:

a presenting unit that presents the rotation angle of the tip end of the catheter calculated by the catheter tip-end rotation angle calculation unit to a user.

6. The catheter tip-end rotation angle calculation apparatus according to claim 5, further comprising:

an image-capturing parameter information acquisition unit that acquires image-capturing parameter information that is information about an image-capturing condition and an orientation of each of a plurality of X-ray image capturing devices at a time of image-capturing;

an image acquisition unit that acquires a plurality of X-ray images including the tip end portion of the catheter captured by the plurality of X-ray image capturing devices provided at different positions;

a catheter rotation axis determination unit that extracts a part of the catheter that is straight in each X-ray image based on the plurality of X-ray images acquired by the image acquisition unit, reconstructs a three-dimensional shape of the catheter by using the extracted part of the catheter that is straight and the image-capturing parameter information at a time of image-capturing of the each X-ray image acquired by the image-capturing parameter information acquisition unit, and determines a catheter rotation axis that is a rotation axis with respect to the catheter insertion direction of the catheter based on the reconstructed three-dimensional shape of the catheter;

a catheter shape storage unit that stores, for a plurality of types of catheters, shapes of tip ends of the catheters for each rotation angle of the tip ends of the catheters; and a catheter tip-end rotation angle correction unit, wherein the catheter tip-end rotation angle correction unit includes:

an acquisition unit that acquires a first X-ray image from the plurality of X-ray images from the image acquisition unit, the rotation angle at the tip end of the catheter and the second rotation angle from the catheter tip-end rotation angle calculation unit, the catheter rotation axis from the catheter rotation axis determination unit, and image-capturing parameter information at a time of capturing the first X-ray image from the image-capturing parameter information acquisition unit;

a calibration image generation unit that acquires from the catheter shape storage unit, for respective rotation angles from the rotation angle of the tip end of the catheter to the second rotation angle acquired by the acquisition unit, a plurality of shapes of the tip end of the catheter, and generates a plurality of calibration images where the acquired plurality of shapes of the tip end of the catheter and the rotation angles are associated;

a comparison unit that compares the first X-ray image acquired from the acquisition unit and the plurality of calibration images generated by the calibration image generation unit, and determines a calibration image with a highest degree of similarity to the first X-ray image; and a rotation angle determination unit that determines the rotation angle corresponding to the calibration image with the highest degree of similarity to the first X-ray image determined by the comparison unit, as the rotation angle of the tip end of the catheter, and wherein the presenting unit presents the rotation angle of the tip end of the catheter determined by the rotation angle determination unit to the user.

7. The catheter tip-end rotation angle calculation apparatus according to claim 6, further comprising:

a correction switching unit that switches between whether or not to perform correction by the catheter tip-end rotation angle correction unit, according to a lesion area where the tip end portion of the catheter in a body lumen is to reach.

8. The catheter tip-end rotation angle calculation apparatus according to claim 6, further comprising:

a correction switching unit that switches between whether or not to perform correction by the catheter tip-end rotation angle correction unit, according to an insertion length of the catheter inserted into a body lumen.

9. The catheter tip-end rotation angle calculation apparatus according to claim 6, further comprising:

a correction switching unit that switches between whether or not to perform correction by the catheter tip-end rotation angle correction unit, according to an image of the tip end portion of the catheter inserted into a body lumen.

10. The catheter tip-end rotation angle calculation apparatus according to claim 1, further comprising:

an image acquisition unit that acquires an X-ray image captured by an X-ray image capturing device that image-captures a region including the tip end portion of the catheter when the catheter is inserted into a body lumen;

a catheter tip-end portion extraction unit that extracts the tip end portion of the catheter from the X-ray image acquired by the image acquisition unit; and a motion detection unit that detects motion of the tip end portion of the catheter extracted by the catheter tip-end portion extraction unit, wherein the catheter tip-end rotation angle calculation unit calculates the rotation angle of the tip end of the catheter in a case where the motion detection unit detects motion, and does not calculate the rotation angle of the tip end of the catheter in a case where the motion detection unit does not detect motion.

11. The catheter tip-end rotation angle calculation apparatus according to claim 1, wherein the catheter is a first catheter, the movement restriction unit is a first movement restriction unit, the catheter insertion length measurement unit is a first catheter insertion length measurement unit, the catheter tip-end rotation angle calculation unit is a first catheter tip-end rotation angle calculation unit, the catheter insertion direction is a first catheter insertion direction, and the catheter tip-end rotation angle calculation apparatus further comprises:

a second movement restriction unit, of a tube shape, that is penetrated from a third hole to a fourth hole, that restricts movement of a second catheter to a second catheter insertion direction by causing the second catheter to pass through from the third hole to the fourth hole;

a third rotation angle measurement unit that measures a third rotation angle that is a rotation angle of the second catheter at the third hole;

a fourth rotation angle measurement unit that measures a fourth rotation angle that is a rotation angle of the second catheter at the fourth hole;

a second catheter insertion length measurement unit that measures a second catheter insertion length that is a length from the third hole or the fourth hole to a tip end portion of the second catheter; and a second catheter tip-end rotation angle calculation unit that calculates $\theta_s$ that is a rotation angle of a tip end of the second catheter by $\theta_s=\theta_3-(\theta_3-\theta_4)\cdot L_s/L_{34}$, where the third rotation angle is $\theta_3$, the fourth rotation angle is $\theta_4$, the second catheter insertion length is $L_s$, and a distance between the third hole and the fourth hole is $L_{34}$.

12. The catheter tip-end rotation angle calculation apparatus according to claim 11, wherein the second catheter is an inner catheter, and the first catheter is an outer catheter for facilitating guiding of the inner catheter.

13. A catheter tip-end rotation angle calculation apparatus for calculating a rotation angle of a tip end of a catheter inserted into a body lumen, by using a movement restriction unit, of a tube shape, that is configured to be penetrated from a first hole to a second hole, and restrict movement of the catheter to an insertion direction by causing the catheter to pass through from the first hole to the second hole, the catheter tip-end rotation angle calculation apparatus comprising:

a catheter tip-end rotation angle calculation unit that acquires a first rotation angle that is a rotation angle of the catheter at the first hole measured by a first rotation angle measurement unit, a second rotation angle that is a rotation angle of the catheter at the second hole measured by a second rotation angle measurement unit, and a catheter insertion length that is a length from the first hole or the second hole to a tip end portion of the catheter measured by a catheter insertion length measurement unit, and that calculates $\theta$ that is a rotation angle of a tip end of the catheter by $\theta=\theta_1-(\theta_1-\theta_2)\cdot L/L_{12}$, where the first rotation angle is $\theta_1$, the second rotation angle is $\theta_2$, the catheter insertion length is $L$, and a distance between the first hole and the second hole is $L_{12}$.

14. A catheter tip-end rotation angle calculation method of calculating a rotation angle of a tip end of a catheter inserted into a body lumen, by using a movement restriction unit, of a tube shape, that is penetrated from a first hole to a second hole, and restricts movement of the catheter to an insertion direction by causing the catheter to pass through from the first hole to the second hole, the method comprising:

measuring a first rotation angle that is a rotation angle of the catheter at the first hole;

measuring a second rotation angle that is a rotation angle of the catheter at the second hole;

measuring a catheter insertion length that is a length from the first hole or the second hole to a tip end portion of the catheter; and calculating $\theta$ that is a rotation angle of a tip end of the catheter by $\theta=\theta_1-(\theta_1-\theta_7)\cdot L/L_{12}$, where the first rotation angle is $\theta_1$, the second rotation angle is $\theta_2$, the catheter insertion length is $L$, and a distance between the first hole and the second hole is $L_{12}$.

15. A non-transitory computer-readable recording medium including a catheter tip-end rotation angle calculation program for causing a computer to perform the catheter tip-end rotation angle calculation method according to claim 14.

16. A catheter tip-end rotation angle calculation method of calculating a rotation angle of a tip end of a catheter inserted into a body lumen, by using a movement restriction unit, of a tube shape, that is penetrated from a first hole to a second hole, and restricts movement of the catheter to an insertion direction by causing the catheter to pass through from the first hole to the second hole, the method comprising:

acquiring a first rotation angle that is a rotation angle of the catheter at the first hole measured by a first rotation angle measurement unit, a second rotation angle that is a rotation angle of the catheter at the second hole measured by a second rotation angle measurement unit, and a catheter insertion length that is a length from the first hole or the second hole to a tip end portion of the catheter measured by a catheter insertion length measurement unit, and calculating $\theta$ that is a rotation angle of a tip end of the catheter by $\theta=\theta_1-(\theta_1-\theta_2) \cdot L/L_{12}$, where the first rotation angle is $\theta_1$, the second rotation angle is $\theta_2$, the catheter insertion length is L, and a distance between the first hole and the second hole is $L_{12}$.

17. A non-transitory computer-readable recording medium including a catheter tip-end rotation angle calculation program for causing a computer to perform the catheter tip-end rotation angle calculation method according to claim 16.

* * * * *